(12) United States Patent
Kwong et al.

(10) Patent No.: US 9,673,406 B2
(45) Date of Patent: Jun. 6, 2017

(54) METAL COMPLEXES WITH BORON-NITROGEN HETEROCYCLE CONTAINING LIGANDS

(71) Applicant: Universal Display Corporation, Ewing, NJ (US)

(72) Inventors: Raymond Kwong, Plainsboro, NJ (US); Bin Ma, Plainsboro, NJ (US); Jui-Yi Tsai, Newtown, PA (US); Scott Beers, Flemington, NJ (US); Ed Barron, Hamilton, NJ (US); Gregg Kottas, Yardley, PA (US); Alexey Dyatkin, Ambler, PA (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 847 days.

(21) Appl. No.: 14/052,159

(22) Filed: Oct. 11, 2013

(65) Prior Publication Data

US 2014/0039192 A1 Feb. 6, 2014

Related U.S. Application Data

(63) Continuation-in-part of application No. 12/781,493, filed on May 17, 2010, now Pat. No. 8,586,203.

(60) Provisional application No. 61/179,933, filed on May 20, 2009.

(51) Int. Cl.
| | |
|---|---|
| *C07F 15/00* | (2006.01) |
| *C09K 11/06* | (2006.01) |
| *H01L 51/00* | (2006.01) |
| *H05B 33/10* | (2006.01) |
| *H01L 51/54* | (2006.01) |
| *H01L 51/50* | (2006.01) |

(52) U.S. Cl.
CPC ...... *H01L 51/0085* (2013.01); *C07F 15/0033* (2013.01); *C09K 11/06* (2013.01); *H05B 33/10* (2013.01); *C09K 2211/104* (2013.01); *C09K 2211/1007* (2013.01); *C09K 2211/1011* (2013.01); *C09K 2211/1029* (2013.01); *C09K 2211/1044* (2013.01); *C09K 2211/185* (2013.01); *H01L 51/5016* (2013.01)

(58) Field of Classification Search
None
See application file for complete search history.

(56) References Cited

U.S. PATENT DOCUMENTS

| | | | |
|---|---|---|---|
| 4,769,292 A | 9/1988 | Tang et al. | |
| 5,061,569 A | 10/1991 | VanSlyke et al. | |
| 5,247,190 A | 9/1993 | Friend et al. | |
| 5,703,436 A | 12/1997 | Forrest et al. | |
| 5,707,745 A | 1/1998 | Forrest et al. | |
| 5,834,893 A | 11/1998 | Bulovic et al. | |
| 5,844,363 A | 12/1998 | Gu et al. | |
| 6,013,982 A | 1/2000 | Thompson et al. | |
| 6,083,936 A | 7/2000 | Groziak | |
| 6,087,196 A | 7/2000 | Sturm et al. | |
| 6,091,195 A | 7/2000 | Forrest et al. | |
| 6,097,147 A | 8/2000 | Baldo et al. | |
| 6,294,398 B1 | 9/2001 | Kim et al. | |
| 6,303,238 B1 | 10/2001 | Thompson et al. | |
| 6,337,102 B1 | 1/2002 | Forrest et al. | |
| 6,468,819 B1 | 10/2002 | Kim et al. | |
| 6,528,187 B1 | 3/2003 | Okada | |
| 6,687,266 B1 | 2/2004 | Ma et al. | |
| 6,835,469 B2 | 12/2004 | Kwong et al. | |
| 6,835,473 B2 | 12/2004 | Matsuura et al. | |
| 6,921,915 B2 | 7/2005 | Takiguchi et al. | |
| 7,087,321 B2 | 8/2006 | Kwong et al. | |
| 7,090,928 B2 | 8/2006 | Thompson et al. | |
| 7,154,114 B2 | 12/2006 | Brooks et al. | |
| 7,250,226 B2 | 7/2007 | Tokito et al. | |
| 7,279,704 B2 | 10/2007 | Walters et al. | |
| 7,332,232 B2 | 2/2008 | Ma et al. | |
| 7,338,722 B2 | 3/2008 | Thompson et al. | |
| 7,393,599 B2 | 7/2008 | Thompson et al. | |
| 7,396,598 B2 | 7/2008 | Takeuchi et al. | |
| 7,431,968 B1 | 10/2008 | Shtein et al. | |
| 7,445,855 B2 | 11/2008 | Mackenzie et al. | |
| 7,534,505 B2 | 5/2009 | Lin et al. | |
| 2002/0034656 A1 | 3/2002 | Thompson et al. | |
| 2002/0134984 A1 | 9/2002 | Igarashi | |
| 2002/0158242 A1 | 10/2002 | Son et al. | |
| 2003/0138657 A1 | 7/2003 | Li et al. | |
| 2003/0152802 A1 | 8/2003 | Tsuboyama et al. | |
| 2003/0157366 A1 | 8/2003 | Matsuura et al. | |
| 2003/0162053 A1 | 8/2003 | Marks et al. | |
| 2003/0175553 A1 | 9/2003 | Thompson et al. | |

(Continued)

FOREIGN PATENT DOCUMENTS

| | | |
|---|---|---|
| CA | 2484685 | 11/2003 |
| CN | 101171320 | 4/2008 |

(Continued)

OTHER PUBLICATIONS

Dewar, Michael J.S., et al., "New Heteroaromatic Compounds, XXXIII, 5,1,3,4-Boratriazaroles," Journal of the American Chemical Society, 1971, 93(13), pp. 3298-3299.

(Continued)

*Primary Examiner* — Marie R. Yamnitzky
(74) *Attorney, Agent, or Firm* — Duane Morris LLP

(57) ABSTRACT

Novel organic compounds comprising a boron-nitrogen heterocycle are provided. In particular, the compound contains an azaborine. The compounds may be used in organic light emitting devices to provide devices having improved photophysical and electronic properties.

2 Claims, 4 Drawing Sheets

(56) References Cited

U.S. PATENT DOCUMENTS

| | | |
|---|---|---|
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0072970 A1 | 4/2005 | Saito |
| 2005/0112407 A1 | 5/2005 | Ogasawara et al. |
| 2005/0123789 A1 | 6/2005 | Vargas et al. |
| 2005/0153164 A1 | 7/2005 | Che et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0190359 A1 | 8/2007 | Knowles et al. |
| 2007/0196687 A1 | 8/2007 | Oshiyama et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Prakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2011/0284799 A1 | 11/2011 | Stoessel et al. |
| 2012/0004407 A1 | 1/2012 | Stoessel et al. |
| 2015/0322091 A1 | 11/2015 | Stoessel et al. |

FOREIGN PATENT DOCUMENTS

| | | |
|---|---|---|
| EP | 0650955 | 5/1995 |
| EP | 1725079 | 11/2006 |
| EP | 2034538 | 3/2009 |
| JP | 2003234192 | 8/2003 |
| JP | 200511610 | 1/2005 |
| JP | 2007123392 | 5/2007 |
| JP | 2007254297 | 10/2007 |
| JP | 2008074939 | 4/2008 |
| KR | 1020060003630 | 1/2006 |
| WO | 01/39234 | 5/2001 |
| WO | 02/02714 | 1/2002 |
| WO | 02/15645 | 2/2002 |
| WO | 03040257 | 5/2003 |
| WO | 03060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009021126 | 2/2009 |
| WO | 2009050290 | 4/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |
| WO | 2010135519 | 11/2010 |

OTHER PUBLICATIONS

Schmid, Günter, et al., "Synthesis, Properties, and Structural Investigations of 1,3,2-Diazaborolidines and 2,3-Dihydro-1H-1,3,2-diazaboroles," Inorganic Chemistry, 1990, vol, 29, No. 22, pp. 4421-4429.

Gragg, B.R., et al., "Boron-Nitrogen Compounds, LXXI, Preparation and Properties of (2-Pyridylamino)Diethylborane," Journal of Organometallic Chemistry, 1978, vol. 149, pp. 271-277.

Gragg, B.R., et al., "Boron-Nitrogen Compounds, LXI, Studies on (2-Pyridylamino)Diphenylborane and Some Related Species," Journal of Organometallic Chemistry, 1976, vol. 117, pp. 1-11.

Baldo et al.,"Highly Efficient Phosphorescent Emission from Organic Electroluminescent Devices," Nature, vol. 395, 151-154, (1998).

Baldo et al.,"Very high-efficiency green organic light-emitting devices based on electrophosphorescence," Appl. Phys. Lett., vol. 75, No. 1, 4-6 (1999).

Gronowitz S et al: "Heteroaromatic boron compounds, XX. On the preparation of the 6,7-borazarobenzo[b]thiophene system. The preparation of some 3-(2-nitro-3-thienyl) acrylic esters and related compounds. A selective hydrogenation of a vinyl group in the presence of an aromatic nitro group" Chemica Scripta, vol. 15, No. 3, 1980, pp. 145-151, XP009135611.

Gronowitz S et al: "Heteroaromatic boron compounds, XVIII. The preparation of the 4,5-borazarobenzo[I,2-b;4,3-b']dithiophene system" Chemica Scripta, vol. 15, No. 1, 1980, pp. 23-26, XP009135610.

Fang et al., "Syntheses of Ring-Fused B—N Heteroaromatic Compounds", Organometallics (2006), 25(2), 513-518.

Fang et al., "A Bis(1,2-Azaborolyl)yttrium Alkyl Complex: Synthesis, Structure, and Polymerization Study", Organometallics (2008), 27(13), 2892-2895.

Chen et al. "A Boron Analogue of Furan. The Synthesis and Coordination Chemistry of 2-Substituted-1,2- Oxaborolides" Organometaliics (2004), 23(21), 5088-5091.

Ashe et al. "Synthesis and Coordination Chemistry of 3a,7a-Azaborindenyl, a New Isoelectronic Analogue of the Indenyl Ligand" Organometallics (2002), 21(22), 4578-4580.

Ashe et al., "Synthesis of 1,2-Dihydro-1,2-azaborines and Their Conversion to Tricarbonyl Chromium and Molybdenum Complexes" Organometallics (2001), 20(25), 5413-5418.

Marwitz et al. "A hybrid organic/inorganic benzene" Angewandte Chemie, International Edition (2009), 48(5), 973-977.

Abbey et al. "Crystal Clear Structural Evidence for Electron Delocalization in 1,2-Dihydro-1,2-azaborines" Journal of the American Chemical Society (2008) 130(23), 7250-7252.

Ashe et al., "A synthesis of aromatic five- and six-membered B—N heterocycles via ring closing metathesis", Org. Lett. 2, pp. 2089-2091 (2000).

(56) References Cited

OTHER PUBLICATIONS

Kranz et al., "N-methyl-B-mesityldibenzo-1,4-azaborinine: the first experimental structure of a 1,4-azaborinine derivative", J. Chem. Soc., Chem. Commun., pp. 1247-1248 (1992).
Agou et al., "Development of a general route to periphery-functionalized azaborines and ladder-type azaborines by using common intermediates", Chem. Commun. pp. 3204-3206 (2007).
Davies et al., "New heteroaromatic compounds. XXVI. Synthesis of borazarenes", J. Am. Chem. Soc. 89, 6294-6297 (1967).
Pan et al., "1,2-azaboratabenzene: a heterocyclic ligand with an adjustable basicity at Nitrogen", Organometallics 23, 5626-5629 (2004).
Pan et al., "Switchable haptotropic migrations of tricarbonylchromium complexes of 1,2-dihydro-2-phenyl-1,2-azaborine", Organometallics 25, pp. 197-202 (2006).
Fiedler et al., "Electronic structure of pi conjugated redox systems with borane/boraraalkene end groups", Inorg. Chem. 35, 3039-3043 (1996).
White D.G., "2-phenyl-2, 1-borazarene and derivatives of 1,2-azaboracycloalkanes" J. Am. Chem. Soc. 85, pp. 3634-3636 (1963).
Blomberg et al., "Synthesis of beta-strand mimetic based on a pyridine scaffold", Tetrahedron 62, pp. 10937-10944 (2006).
Segawa et al., "Synthesis of PBO Princer Iridium Complexes: A Supporting Boryl Ligand", J. Am. Chem. Soc. 2009, 131, pp. 9291-9203.
Singleton et al., "Allylboration of alkenes with allyldihaloboranes", J. Am. Chem. Soc., 1996, 118(41) pp. 9986-9987.
Search Report issued Mar. 17, 2015 for corresponding Taiwan Patent Application No. 103134474.
Adachi, Chihaya et al., "Organic Electroluminescent Device Having a Hole Conductor as an Emitting Layer," Appl. Phys. Lett., 55(15): 1489-1491 (1989).
Adachi, Chihaya et al., "Nearly 100% Internal Phosphorescence Efficiency in an Organic Light Emitting Device," J. Appl. Phys., 90(10): 5048-5051 (2001).
Adachi, Chihaya et al., "High-Efficiency Red Electrophosphorescence Devices," Appl. Phys. Lett., 78(11)1622-1624 (2001).
Aonuma, Masaki et al., "Material Design of Hole Transport Materials Capable of Thick-Film Formation in Organic Light Emitting Diodes," Appl. Phys. Lett., 90, Apr. 30, 2007, 183503-1-183503-3.
Gao, Zhiqiang et al., "Bright-Blue Electroluminescence From a Silyl-Substituted ter-(phenylene-vinylene) derivative," Appl. Phys. Lett., 74(6): 865-867 (1999).
Guo, Tzung-Fang et al., "Highly Efficient Electrophosphorescent Polymer Light-Emitting Devices," Organic Electronics, 1: 15-20 (2000).
Hamada, Yuji et al., "High Luminance in Organic Electroluminescent Devices with Bis(10-hydroxybenzo[h]quinolinato) beryllium as an Emitter," Chem. Lett., 905-906 (1993).
Holmes, R.J. et al., "Blue Organic Electrophosphorescence Using Exothermic Host-Guest Energy Transfer," Appl. Phys. Lett., 82(15):2422-2424 (2003).
Hu, Nan-Xing et al., "Novel High Tg Hole-Transport Molecules Based on Indolo[3,2-b]carbazoles for Organic Light-Emitting Devices," Synthetic Metals, 111-112:421-424 (2000).
Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).
Huang, Wei-Sheng et al., "Highly Phosphorescent Bis-Cyclometalated Iridium Complexes Containing Benzoimidazole-Based Ligands," Chem. Mater., 16(12):2480-2488 (2004).
Hung, L.S. et al., "Anode Modification in Organic Light-Emitting Diodes by Low-Frequency Plasma Polymerization of CHF3," Appl. Phys. Lett., 78(5):673-675 (2001).
Ikai, Masamichi et al., "Highly Efficient Phosphorescence From Organic Light-Emitting Devices with an Exciton-Block Layer," Appl. Phys. Lett., 79(2):156-158 (2001).

Ikeda, Hisao et al., "P-185 Low-Drive-Voltage OLEDs with a Buffer Layer Having Molybdenum Oxide," SID Symposium Digest, 37:923-926 (2006).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).
Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Kido, Junji et al.,"1,2,4-Triazole Derivative as an Electron Transport Layer in Organic Electroluminescent Devices," Jpn. J. Appl. Phys., 32:L917-L920 (1993).
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).
Kwong, Raymond C. et al., "High Operational Stability of Electrophosphorescent Devices," Appl. Phys. Lett., 81(1)162-164 (2002).
Lamansky, Sergey et al., "Synthesis and Characterization of Phosphorescent Cyclometalated Iridium Complexes," Inorg. Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).
Lo, Shih-Chun et al., "Blue Phosphorescence from Iridium(III) Complexes at Room Temperature," Chem. Mater., 18(21)5119-5129 (2006).
Ma, Yuguang et al., "Triplet Luminescent Dinuclear-Gold(I) Complex-Based Light-Emitting Diodes with Low Turn-On voltage," Appl. Phys. Lett., 74(10)1361-1363 (1999).
Mi, Bao-Xiu et al., "Thermally Stable Hole-Transporting Material for Organic Light-Emitting Diode an Isoindole Derivative," Chem. Mater., 15(16)3148-3151 (2003).
Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).
Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and Shirota,Yasuhiko, "5,5'-Bis(dimesitylboryl)-2,2'-bithiophene and 5,5"-Bis(dimesitylboryl)-2,2'5',2"-terthiophene as a Novel Family of Electron-Transporting Amorphous Molecular Materials," J. Am. Chem. Soc., 120 (37):9714-9715 (1998).
Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based on Silole Derivatives and Their Exciplexes," Organic Electronics, 4:113-121 (2003).
Paulose, Betty Marie Jennifer S. et al., "First Examples of Alkenyl Pyridines as Organic Ligands for Phosphorescent Iridium Complexes," Adv. Mater., 16(22):2003-2007 (2004).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am. Chem. Soc., 122(8):1832-1833 (2000).
Salbeck, J. et al., "Low Molecular Organic Glasses for Blue Electroluminescence," Synthetic Metals, 91: 209-215 (1997).
Shirota, Yasuhiko et al., "Starburst Molecules Based on pi-Electron Systems as Materials for Organic Electroluminescent Devices," Journal of Luminescence, 72-74:985-991 (1997).
Sotoyama, Wataru et al., "Efficient Organic Light-Emitting Diodes with Phosphorescent Platinum Complexes Containing N^C^N -Coordinating Tridentate Ligand," Appl. Phys. Lett., 86:153505-1-153505-3 (2005).

(56) References Cited

OTHER PUBLICATIONS

Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
T. Östergård et al., "Langmuir-Blodgett Light-Emitting Diodes of Poly(3-Hexylthiophene) Electro-Optical characteristics Related to Structure," Synthetic Metals, 88:171-177 (1997).
Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).
Tang, C.W. and VanSlyke, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II Phosphorescent Emitters," Adv. Mater., 17(8)1059-1064 (2005).
Van Slyke, S. A. et al., "Organic Electroluminescent Devices with Improved Stability," Appl. Phys. Lett., 69(15)2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al.,"A Novel Class of Phosphorescent Gold(III) Alkynyl-Based Organic Light-Emitting Devices with Tunable Colour," Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).
Dewar, M.J.S. et al., New Heteroaromatic Compounds. XXXIII. 5,1,3,4-Boratriazaroles2, Journal of the American Society, 1971, 3298-3299, 93(13).

Schmid, G. et al., Synthesis, Properties, and Structural Investigations of 1,3,2-Diazaborolidines and 2,3-Dihydro-1H-1,3,2-diazaborles, Inorganic Chemistry, 1990, 4421-4429, 29(22).
Gragg, B.R., et al., LXXI, Preparation and Properties of (2-Pyridylamino) Diethylborane, Journal of Organometallic Chemistry, 1978, 149(3), 271-277.
Gragg, B.R., et al., LXI, Studies of (2-Pyridylamino) Diphenylborane and Some Related Species, Journal of Organometallic Chemistry, 1976, 117(1), 1-11.
Dorokhov, V.A., et al., Boron Chelate Complexes with Some Enaminones and Diketones Containing the Pyridine Fragment and their Mutual Transformations in Solutions, Russian Chemical Bulletin, 1996, 45(3), 671-675.
Dueruest, Yasar et al., Potentiometric Study of Acid-Base Equilibria of 3,5-Disubstituted 1,2,4,5-Oxadiazaboroles in Nonaqueous Media, Journal of Chemical & Engineering Data, 2007, 52(3), 718-720.
Dueruest, Yasar et al., Synthesis of New Thiophene, Furan and Pyridine Substituted 1,2,4,5-Oxadiazaboroles, Polyhedron, 2008, 27(3), 999-1007.
Friese, Bernd et al., On the Constitution of the 1,5-Diphenylcarbazonato—Diphenylboron Chelate—A Chemical Approach, Monatshefte Fuer Chemie, 1978, 109(3), 711-718.
Dewar, M.J.S., et al., New Heteroaromatic Compounds—XXXIV—Tetrahedron, 1972, 28(4), 959-961.
Weber, Lothar et al., Reaction of 1,3-Dialkyl-4,5-dimethylimidazol-2-ylidenes with 2-Bromo-2,3dihydro-1H-1,3,2-diazaboroles (Alkyl = iPr and tBu), Chemische Berichte/Recueil, 1997, 130(6), 705-710.
Hohaus, Eberhard, Boron Chelates and Boron Metal Chelates, IV: Spectroscopic Investigation of Salicylaldehyde Azomethine Diphenylboron Chelates, Monatshefte Fuer Chemie, 1980, 863-875.

X1 = C or N

X2 and X3 = C, N or B

Compound 1  Compound 6  Compound 7

Compound 12  Compound 25  Compound 28

METAL COMPLEXES WITH BORON-NITROGEN HETEROCYCLE CONTAINING LIGANDS

CROSS-REFERENCE TO RELATED APPLICATIONS

This application is a continuation-in-part application of U.S. patent application Ser. No. 12/781,493, filed May 17, 2010, now U.S. Pat. No. 8,586,203, which claims priority to U.S. Provisional Application Ser. No. 61/179,933, filed May 20, 2009, the disclosures of which are herein expressly incorporated by reference in their entirety.

PARTIES TO A JOINT RESEARCH AGREEMENT

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to novel organic materials that may be advantageously used in organic light emitting devices (OLEDs). More particularly, the present invention relates to novel compounds comprising a boron-nitrogen heterocycle and devices containing such compounds.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the structure:

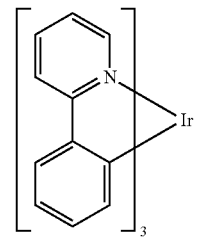

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

A novel class of organic materials are provided. The materials are compounds with boron-nitrogen heterocycle containing ligands. The materials may be advantageously used in OLEDs. In particular, the materials may be used as an emitting dopant in such devices.

Compounds comprising a boron-nitrogen heterocycle are provided, such compounds comprising a ligand L having the structure:

FORMULA I

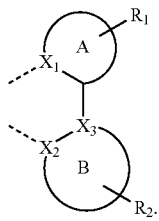

A and B may represent a 5-membered or 6-membered carbocycle or heterocycle. B is a boron-nitrogen heterocycle. $X_1$ is selected from the group consisting of carbon and nitrogen. Preferably, $X_1$ is nitrogen. Preferably, A is:

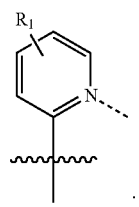

In particular, $R_1$ may be hydrogen.

In one aspect, A is selected from the group consisting of:

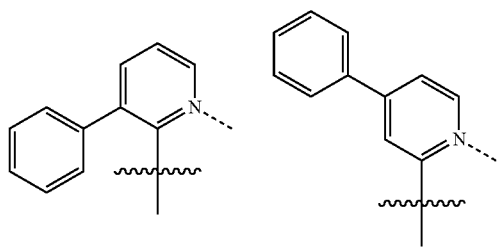

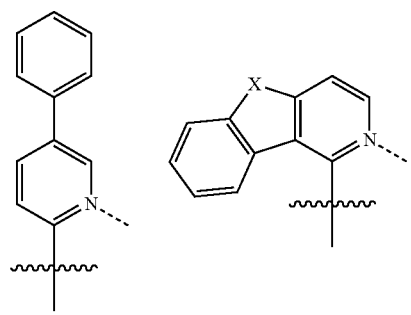

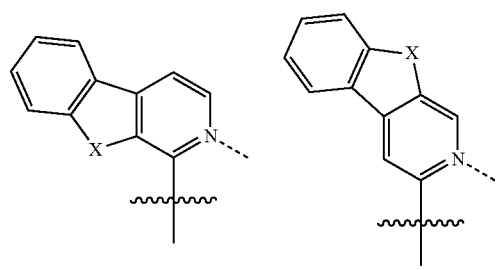

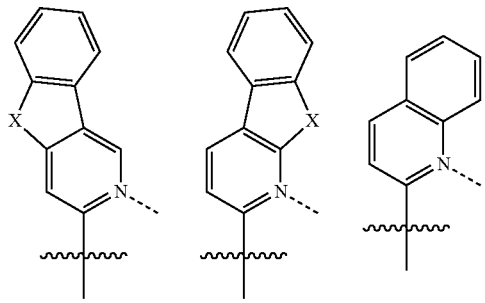

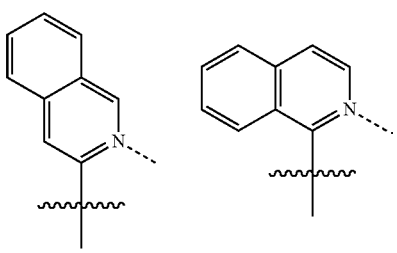

X is selected from the group consisting of S, NZ, O, Se, BZ, CZZ', and C=O. Z and Z' are independently selected from the group consisting of hydrogen, alkyl, and aryl.

In another aspect, A is selected from the group consisting of:

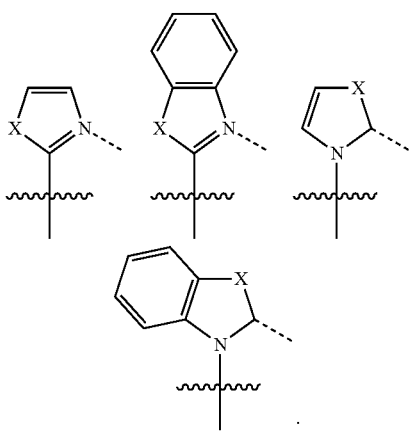

X is selected from the group consisting of S, NZ, O, Se, BZ, CZZ', and C=O. Z and Z' are independently selected from the group consisting of hydrogen, alkyl, and aryl.

$X_2$ and $X_3$ are independently selected from the group consisting of carbon, nitrogen, and boron.

$R_1$ and $R_2$ represent mono, di, tri, or tetra substitutions. $R_1$ and $R_2$ are independently selected from the group consisting of hydrogen, alkyl, alkoxy, amino, alkenyl, alkynyl, arylkyl, aryl, and heteroaryl.

The ligand L is coordinated to a metal M having an atomic number greater than 40. Preferably, the metal M is Ir.

In one aspect, the compound provided comprise a ligand L having the structure:

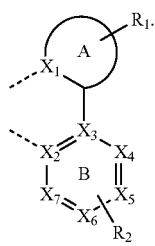

FORMULA II $X_4$, $X_5$, $X_6$, and $X_7$ are independently selected from the group consisting of carbon, nitrogen, and boron.

In another aspect, the compound provided comprise a ligand L having the structure:

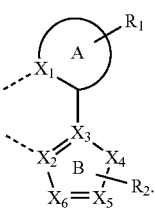

FORMULA III $X_4$, $X_5$, and $X_6$ are independently selected from the group consisting of carbon, nitrogen, and boron.

In yet another aspect, particular compound comprising a ligand L are provided wherein the ligand L is selected from the group consisting of Compound 1-Compound 67. $R_3$, $R_4$, $R_5$, and $R_6$ are independently selected from the group consisting of hydrogen, alkyl, alkoxy, amino, alkenyl, alkynyl, arylkyl, aryl, and heteroaryl.

Preferably, the compound have a ligand L selected from the group consisting of Compound 1, Compound 6, Compound 7, Compound 12, Compound 25, and Compound 28. More preferably, the ligand is Compound 25.

$R_2$ may be hydrogen. $R_3$ may be selected from the group consisting of alkyl, alkoxy, amino, alkenyl, alkynyl, arylkyl, aryl, and heteroaryl.

In one aspect, compounds are provided wherein the ligand L is included in a homoleptic compound. In another aspect, compounds are provided wherein the ligand L is included in a heteroleptic compound.

In particular, compounds having the formula $M^n(L)_a(L')_b(L'')_c$ are provided. n is the oxidation state of the metal M. a is 1, 2, or 3. b is 0, 1, or 2. c is 0, 1, or 2. a+b+c is n. L' and L'' are independently selected from the group consisting of:

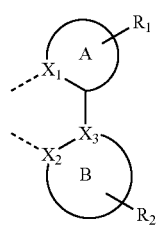

FORMULA I

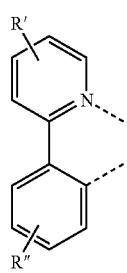

FORMULA IV

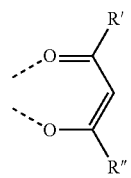

FORMULA V

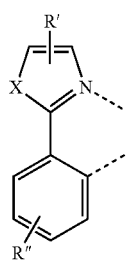

FORMULA VI

-continued

FORMULA VII

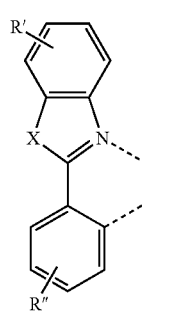

FORMULA VIII

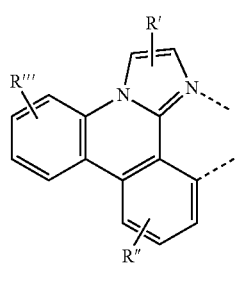

FORMULA IX

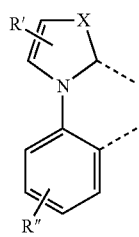

FORMULA X

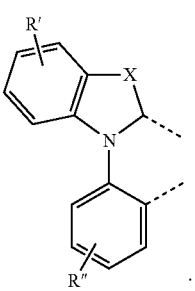

R', R" and R'" are independently selected from the group consisting of hydrogen, alkyl, alkoxy, amino, alkenyl, alkynyl, arylkyl, aryl, and heteroaryl. X is selected from the group consisting of S, NZ, O, Se, BZ, CZZ', and C=O. Z and Z' are independently selected from the group consisting of hydrogen, alkyl, and aryl.

Preferably, L' and L" have FORMULA IV and are independently selected from the group consisting of Compound 68-Compound 83.

Particular boron-nitrogen heterocycle containing compounds are provided, wherein the compound is selected from the group consisting of Compound 84G-Compound 167G. Specific example of boron nitrogen heterocycle containing compounds are provided, including compounds selected from the group consisting of Compound 84-Compound 167. Preferably the compound is Compound 88 or Compound 89.

An organic light emitting device is also provided. The device may include an anode, a cathode, and an organic layer disposed between the anode and the cathode. The organic layer comprises a compound comprising a ligand L having the structure of FORMULA I, as described above.

A consumer product comprising a device is also provided. The device further comprises an anode, a cathode, and an organic layer disposed between the anode and the cathode. The organic layer comprises a compound comprising a ligand L having the formula of FORMULA I, as described above.

In one aspect, the organic layer is an emissive layer and the compound comprising the ligand L having FORMULA I is an emitting dopant. The organic layer may further comprise a host containing a benzene, carbazole, dibenzofuran, dibenzothiophene, dibenzoselenophene, naphthalene, triphenylene, or biphenyl moiety.

Selections for the rings, metal, and substituents described as preferred for compounds comprising a ligand L having FORMULA I are also preferred for use in a device that contains a compound comprising a ligand L having FORMULA I or a consumer product comprising a device that contains a compound comprising a ligand L having FORMULA I. These selections include those for rings A and B, the metal M, the substituents $X_1$-$X_3$, the substituents $R_1$-$R_6$, R', R", R'", and the combination and/or incorporation of ligands L' and L" into an organometallic complex.

Additional compounds comprising a boron-nitrogen heterocycle are provided, such compounds having the formula:

FORMULA XI

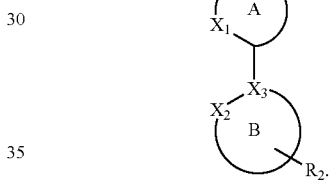

A and B may represent a 5-membered or 6-membered carbocycle or heterocycle. $X_1$ is N or NR. $X_2$ and $X_3$ are independently selected from the group consisting of carbon, nitrogen, and boron. B is a boron-nitrogen heterocycle. R, $R_1$ and $R_2$ represent mono, di, tri, or tetra substitutions. R, $R_1$ and $R_2$ are independently selected from the group consisting of hydrogen, alkyl, alkoxy, amino, alkenyl, alkynyl, arylkyl, aryl, and heteroaryl.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
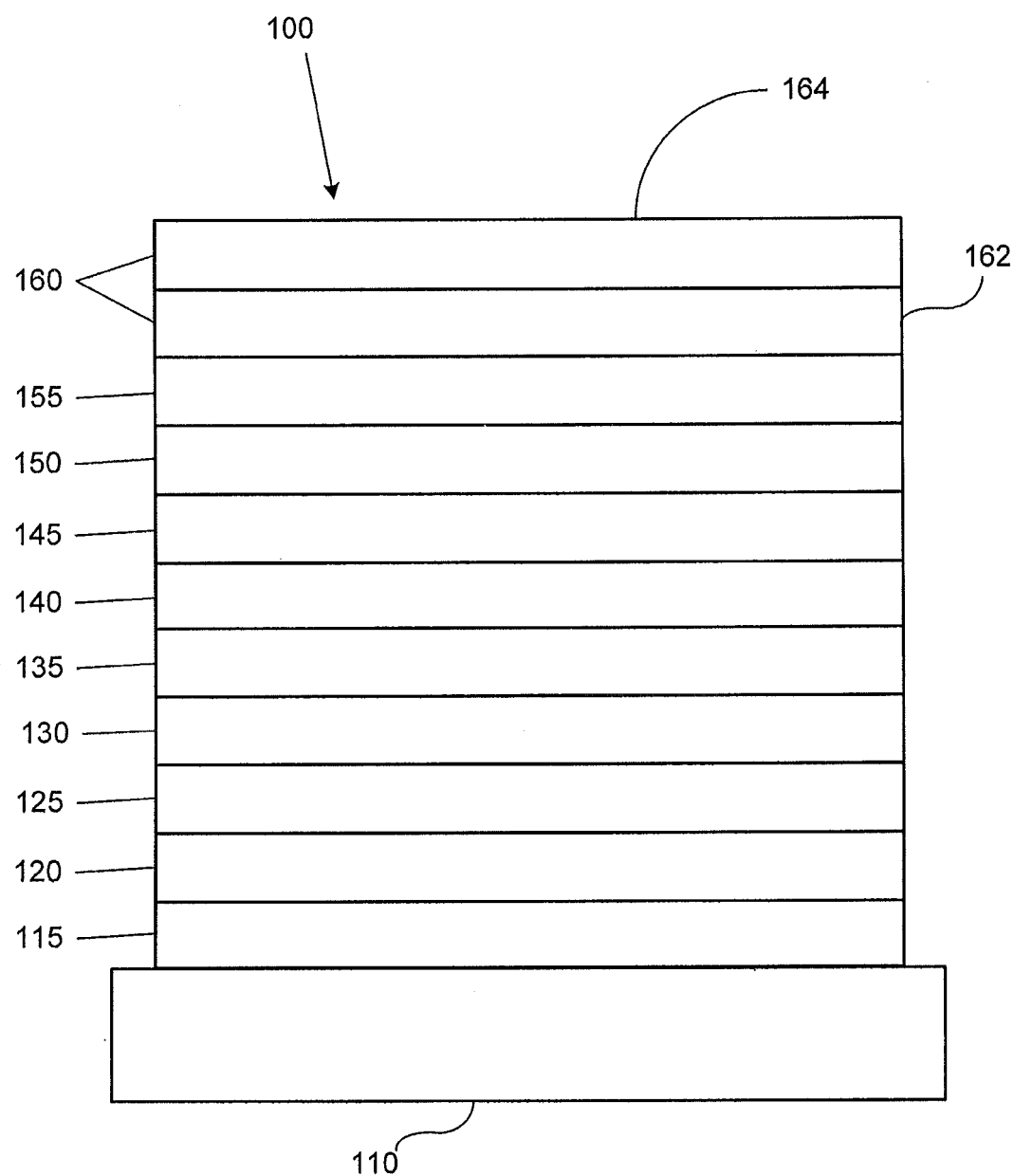
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F.sub.4-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
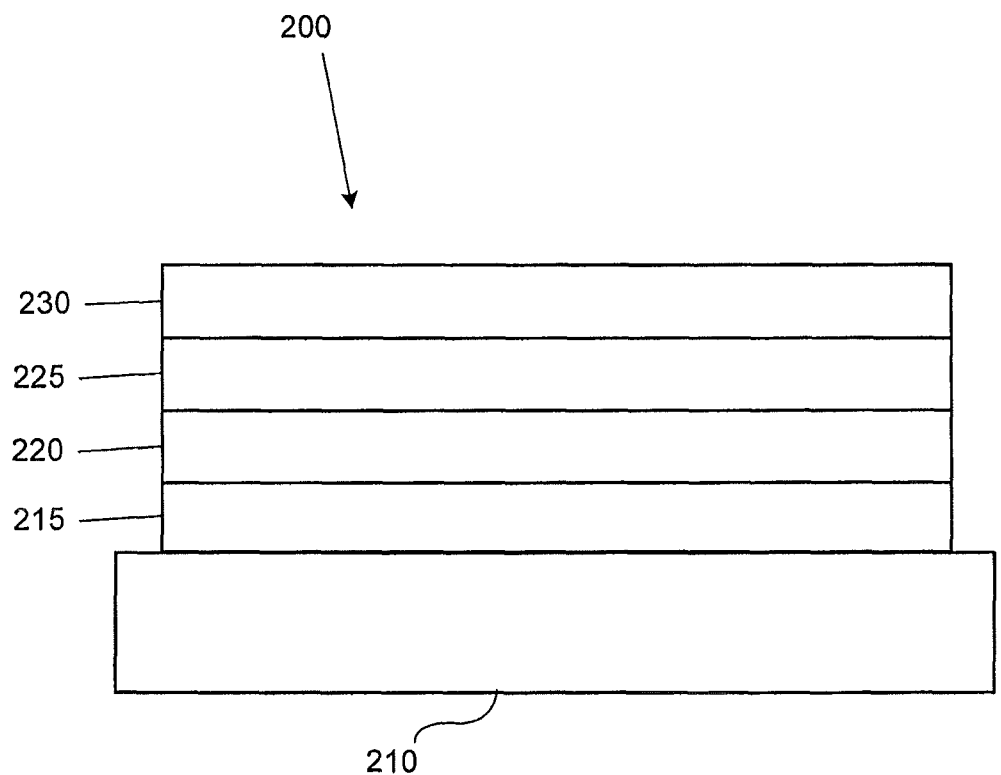
FIG. 2 shows an inverted organic light emitting device that does not have a separate electron transport layer.
Figure 3:
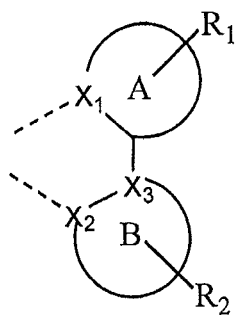
FIG. 3 shows the general structure of a ligand containing a boron-nitrogen heterocycle.
Figure 4:
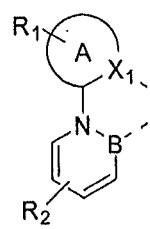
FIG. 4 shows exemplary ligands containing a boron-nitrogen heterocycle.
Figure 4:
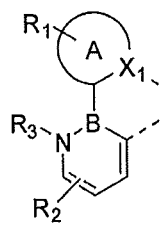
Figure 4:
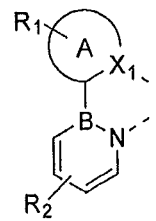
Figure 4:
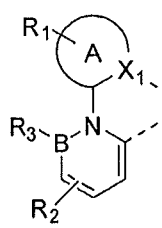
Figure 4:
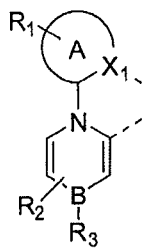
Figure 4:
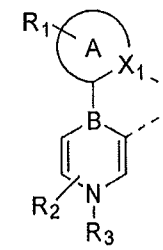

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos.

6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

There are reports of azaborine compounds in the literature (see, e.g., Kranz et al., Chem. Commun. 1247 (1992); Agou et al., Chem. Commun. 3204 (2007); Marwitz et al., Angew. Chem. Int. Ed. 48, 973 (2009); Pan et al., Organometallics 23, 5626 (2004); Pan et al., Organometallics 25, 197 (2006); Ashe et al., Organometallics 20, 5413 (2001); Ashe and Fang., Org. Lett. 2, 2089 (2000); Davies et al., J. Am. Chem. Soc. 89, 6294 (1967); Fiedler et al., Inorg. Chem. 35, 3039 (1996); Whire D. G., J. Am. Chem. Soc. 85, 3634 (1963); US2003/0157366; Blomberg et al., Tetrahedron 62, 10937 (2006); Fang et al., Organometallics 25, 513 (2006); Fang et al., Organometallics 27, 2892 (2008); Chen et al., Organometallics 23, 5088 (2004); Ashe et al., Organometallics 21, 4578 (2002); Abbey et al., Amer. Chem. Soc. 130, 7250 (2008)). However, the compounds containing a boron-nitrogen heterocycle provided herein have a novel structure. These organometallic compounds comprise a ligand containing a boron-nitrogen heterocycle. Such compounds may include ligands comprising a boron-nitrogen heterocycle and a carbocyclic ring, such as phenyl, wherein the ligand is coordinated to a metal. Compounds may also include ligands comprising a boron-nitrogen heterocycle and a N-containing ring, such as pyridine. In addition, these compounds may be advantageously used in OLEDs.

Inorganic/organic hybrids of benzene include 1,2-azaborine, 1,3-azaborine, and 1,4-azaborine. Table 1 below shows the structure of several exemplary boron-nitrogen heterocycles.

TABLE 1

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

It should be noted that each boron-nitrogen heterocycle provided can be drawn in various resonance structures. The resonance structures provided in Table 1 for 1,2-azaborine and 1,4-azaborine are exemplary resonance structures. Without being bound by theory, it is believed that compound containing 1,2-azaborine and 1,4-azaborine may be particularly beneficial. The resonance structures for these compounds show that conjugation may be disrupted by the presence of heteroatoms (i.e., nitrogen and/or boron) in the ring. The broken conjugation may provide high triplet energy for the compounds, which may be a beneficial property.

Using 1,2-azaborine, 1,3-azaborine, 1,4-azaborine, borazine or modifications of these organic/inorganic benzene to replace the regular aromatic moiety in the ligand used in a metal complex, such as Ir(2-phenylpyridine)$_3$, offers a new use for semi-aromatic, semi-conjugated compounds. The organic/inorganic benzene compounds provided herein include boron-nitrogen containing heterocycles with boron and nitrogen atoms in multiple positions within the ring including a ring having multiple boron atoms and multiple nitrogen atoms (i.e., 2N, 2B heterocycles). In particular, heterocycles containing two nitrogen atoms and two boron atoms (i.e., 2N, 2B) within the ring are believed to be a novel azaborine structure and may be particularly useful. In addition, the boron-nitrogen heterocycle may be further substituted by a variety of substituents.

In addition, the compounds including 1,2-azaborine, 1,3-azaborine, 1,4-azaborine may be advantageously used in organic electronics. 1,2-azaborine, 1,3-azaborine, 1,4-azaborine, borazine or modifications of these organic/inorganic benzene compounds can be used to replace the benzene ring found in many organic compounds. In particular, the semi-aromatic nature of azaborine may be useful to tune the electronic and photophysical properties of phenylpyridine-based compounds such as Ir(2-phenylpyridine)$_3$. Table 2 includes exemplary 2-azaborinepyridine complexes with iridium(III). For each of the compounds provided in Table 2, the calculated energy levels and the singlet and triplet energies (DFT, Gaussian/B3lyp/cep-31g) are also provided.

TABLE 2

| Compound | Structure | HOMO (eV) | LUMO (eV) | Gap (eV) | Dipole (Debye) | S1 (nm) | T1 (nm) |
|---|---|---|---|---|---|---|---|
| Ir(ppy)$_3$ | 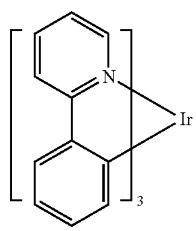 | −4.93 | −1.43 | 3.5 | 6.53 | 452 | 505 |
| ppy | 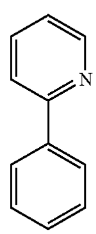 [SMILES: c1ccc(-c2ccccn2)cc1] | −6.23 | −1.41 | 4.82 | 2.07 | 315 | 454 |
| A | 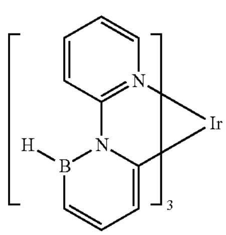 | −5.07 | −1.72 | 3.35 | 9.45 | 457 | 537 |
| B | 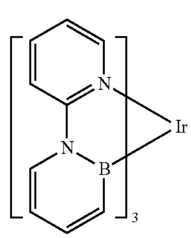 | −4.7 | −1.26 | 3.45 | 6.78 | 483 | 569 |

TABLE 2-continued

| Compound | Structure | HOMO (eV) | LUMO (eV) | Gap (eV) | Dipole (Debye) | S1 (nm) | T1 (nm) |
|---|---|---|---|---|---|---|---|
| C | 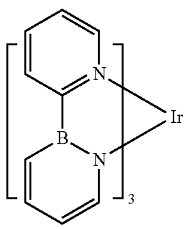 | −5.17 | −1.56 | 3.61 | 7.27 | 427 | 511 |
| D | 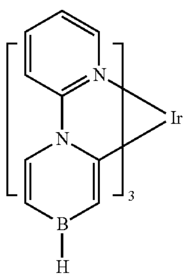 | −5.46 | −1.83 | 3.63 | 14.82 | 437 | 460 |
| D-Ligand | 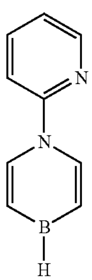 | −6.25 | −1.56 | −4.69 | 5.79 | 319 | 393 |
| E | 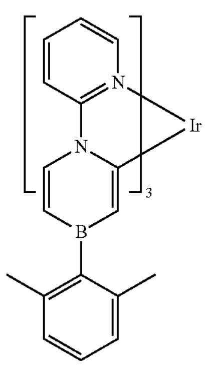 | −5.47 | −1.94 | 3.53 | 16.72 | 431 | 454 |
| F | 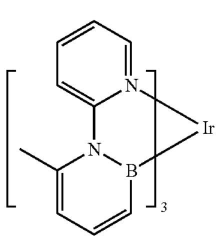 | −4.53 | −1.25 | 3.28 | 6.7 | 514 | 597 |

TABLE 2-continued

| Compound | Structure | HOMO (eV) | LUMO (eV) | Gap (eV) | Dipole (Debye) | S1 (nm) | T1 (nm) |
|---|---|---|---|---|---|---|---|
| G | 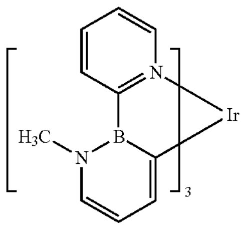 | −4.06 | −1.15 | 2.91 | 5.16 | 562 | 627 |
| H | 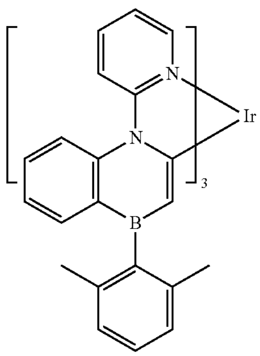 | −5.46 | −1.78 | 3.67 | 14.34 | 422 | 468 |
| I | 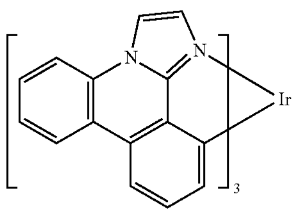 | −4.73 | −1.17 | 3.57 | 4.72 | 446 | 475 |
| I-Ligand | 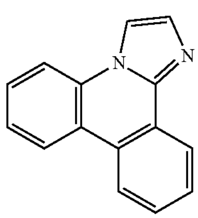 [SMILES: c1ccc2c(c1)c1ccccc1n1ccnc21] | −5.91 | −1.46 | 4.44 | 3.65 | 344 | 470 |

From the calculations in Table 2, it can be seen that depending on the position of the boron atom and the nitrogen atom in the azaborine, a wide range of triplet energies (phosphorescence color) can be achieved. Most notably, Compounds D and E have phosphorescence in the deep blue region (≤460 nm) with very low LUMO levels (<1.8 eV). Such features may render the compounds more stable towards reduction which is believed to be desirable for long OLED device operation lifetime.

Another desirable feature is the triplet energy difference between the ligand and the corresponding metal complex. It is believed that a large triplet energy difference indicates a metal complex with a strong MLCT excited state character. It may also be viewed as a result of strong metal-organic bonding, in this case, Ir—N bond in the top ring and Ir—C/N/B bond in the lower ring. Strong metal-organic bonding is believed to be desirable to obtaining a stable complex for device operation. In Ir(ppy)$_3$, the most fundamental Ir tris C—N cyclometallating complex, the triplet energies of the complex and the ligand (ppy) are 505 nm (2.48 eV) and 454 nm (2.75 eV) respectively. The difference is 0.27 eV. Ir(ppy)$_3$ has a strong MLCT excited state character. In Compound D, the triplet energies of the complex D and the ligand (D-Ligand) are 460 nm (2.72 eV) and 393 nm (3.18 eV) respectively. The difference is 0.46 eV which is even higher than that of Ir(ppy)$_3$, suggesting Compound D has a very strong MLCT excited state character. In Compound I, a blue emitting Ir complex described in US 20080297033, the triplet energies of the complex and the ligand (1-Ligand) are 475 nm (2.63 eV) and 470 nm (2.66 eV) respectively. The difference is only 0.03 eV, suggesting a very weak MLCT excited state character. In fact, the emission profile of Compound I suggests a predominant ligand π to π* or LLCT transition.

As discussed above, the compounds may be further substituted thereby allowing additional tuning of the compound's properties, such as color and energy levels. In particular, Compound B and Compound F both contain a boron-nitrogen heterocycle ligand having 1,2-azaborine yet the two compounds have different properties which may be due to the methyl substitution of the 1,2-azaborine moiety in the ligand of Compound F.

Additionally, the orientation of the boron-nitrogen ligand with respect to the metal may also influence properties of the compound. In particular, Compound A and Compound B have the same ligand structure but differ in the coordination of the ligand to Ir and thus display different properties.

Moreover, the linkage between the boron-nitrogen containing heterocycle and the metal may also influence the compound's properties. In particular, Compound B and Compound C both contain 1,2-azaborine as the boron-nitrogen heterocycle moiety in the ligand. However, Compound B is coordinated to the Ir via a boron atom whereas Compound C is coordinated to the Ir via a nitrogen atom. The different heteroatomic linkage to the metal of the compound may provide altered electronic and photophysical properties.

Novel compounds are provided, the compounds comprising a ligand containing a boron-nitrogen heterocycle. These compounds may be particularly useful as phosphorescent emitters in OLEDs. The compounds contain a boron-nitrogen heterocycle in place of the aromatic moiety (e.g. phenyl) or heteroaromatic moiety typically present in a ligand. Phenylpyridine is a ligand commonly used in metal complexes. In particular, Ir(ppy) type complexes contain a phenylpyridine ligand comprising a pyridine ring and a phenyl ring. The compounds provided herein differ structurally from traditional compounds by the rings present in the ligands. The compounds herein may comprise, for example, a ligand containing a pyridine ring and a boron-nitrogen heterocycle.

B—N (or $B^-=N^+$) bonds and the C=C bonds are isoelectronic and isostructural. When coordinated to a metal, a boron-nitrogen heterocycle ligand has a charge such that the top ring (i.e., A ring) is a neutral donor and the bottom ring (i.e., B ring) is a monoanionic donor. Compounds comprising a boron-nitrogen heterocycle containing ligand are analogous and isoelectronic to the corresponding Ir(ppy) type complexes due to the similarities between the B—N bond and the C=C bond. Preferably, compounds comprising the novel ligand structure provided herein (i.e., ligand comprising an azaborine moiety and a carbocyclic or N-containing ring) may be isoelectronic and isostructural to corresponding Ir(ppy) type complexes. In particular, compounds having B—N bonds have equivalent valence electrons and equivalent structure (i.e., atom connectivity) as compared to Ir(ppy) type compounds.

In addition, metal complexes comprising a boron-nitrogen heterocycle containing ligand may have stronger bonds than Ir(ppy) type complex.

Ligands containing a boron-nitrogen heterocycle provide a novel ring system useful for tuning the photophysical (e.g., color) and electrochemical (e.g., energy levels) properties of metal compounds. As such, compounds comprising a boron-nitrogen heterocycle containing ligand may be useful in red, green, and blue devices. In particular, boron-nitrogen heterocycles may be especially useful in blue devices. Specifically, ligands consisting of 1,2-azaborine or 1,4-azaborine may be especially desirable for use in blue devices. A disruption in conjugation between the two rings of the ligand (i.e., the A ring and the B ring) may provide high triplet energy. The 1,2-azaborine containing ligand may have some conjugation between the two rings in the ligand (i.e., A and B), but the conjugation is less than that of a common ligand such as phenylpyridine. The 1,4-azaborine ligand is believed to have even less conjugation between the two rings. In particular, Compound D (Table 2) is a 1,4-azaborine containing compound and has little conjugation between the pyridine and the azaborine. Thus, the 1,4-azaborine ligand may be the most preferred organic/inorganic benzene hybrid provided herein for use in blue devices because it may provide the highest triplet energy.

Additionally, the atomic connection between the boron-nitrogen containing ring (i.e., B ring) and the other ring (i.e., A ring) of the ligand may contribute to triplet energy. In particular, a heteroatomic linkage between the two rings of the ligand may be especially beneficial. The presence of boron in the B ring at the 1 position provides a heteroatomic linkage between the two rings in the ligand. The presence of nitrogen at the 1 position in a ring containing boron may also provide the heteroatomic linkage. The compounds having a heteroatomic linkage may be especially good compounds for phosphorescent blue devices.

While the use of compounds containing a boron-nitrogen heterocycle as blue emitters is a preferred use, such compounds may be used for other purposes as well, including the emission of other colors, as well as non-emissive uses.

The compounds provided herein comprise a ligand L having the structure:

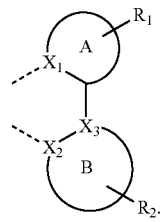

FORMULA I

A and B may represent a 5-membered or 6-membered carbocycle or heterocycle. $X_1$ is selected from the group consisting of carbon and nitrogen. Preferably, $X_1$ is nitrogen.

More preferably, A is:

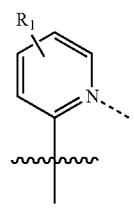

In certain aspects, it may be preferred that $R_1$ is hydrogen. $X_2$ and $X_3$ are independently selected from the group consisting of carbon, nitrogen, and boron. B is a boron-nitrogen heterocycle. In one aspect, A may be selected from the group consisting of:

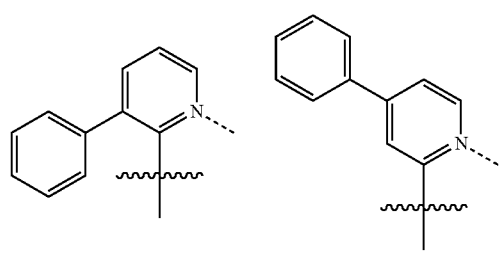

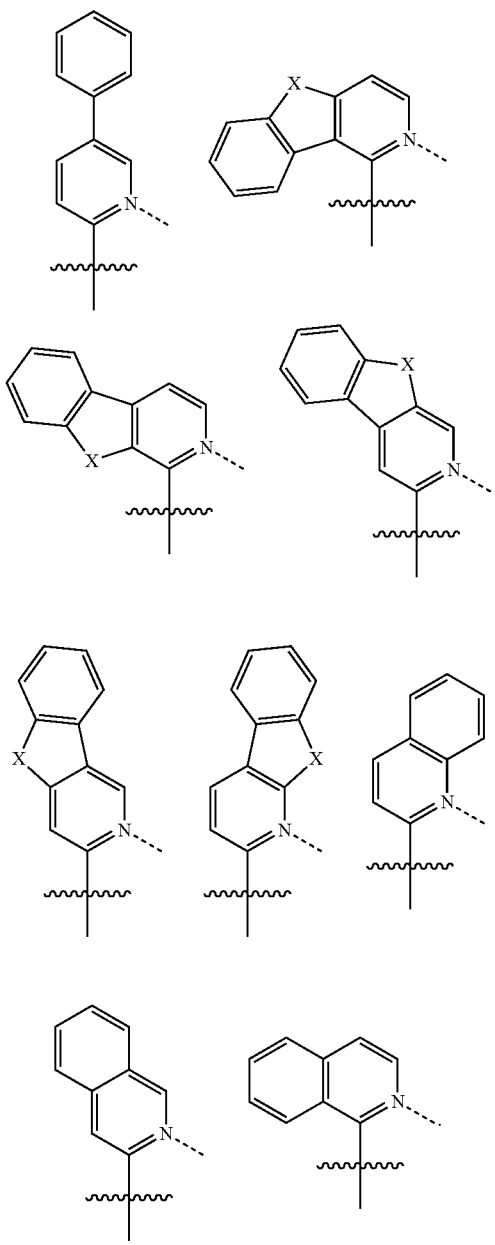

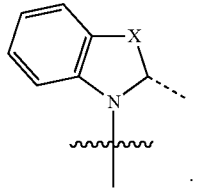

X is selected from the group consisting of S, NZ, O, Se, BZ, CZZ', and C=O. Z and Z' are independently selected from the group consisting of hydrogen, alkyl, and aryl.

R₁ and R₂ represent mono, di, tri, or tetra substitutions. $R_1$ and $R_2$ are independently selected from the group consisting of hydrogen, alkyl, alkoxy, amino, alkenyl, alkynyl, arylkyl, aryl, and heteroaryl.

The ligand L is coordinated to a metal M having an atomic number greater than 40. Preferably, the metal M is Ir.

In one aspect, compounds are provided wherein the compound includes a ligand L having the structure:

FORMULA II

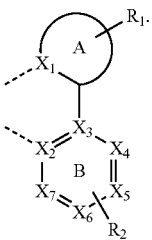

$X_4$, $X_5$, $X_6$, and $X_7$ are independently selected from the group consisting of carbon, nitrogen, and boron.

In another aspect, compounds are provided wherein the compound includes a ligand L having the structure:

FORMULA III

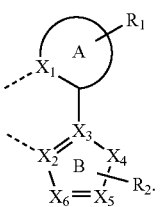

$X_4$, $X_5$, and $X_6$ are independently selected from the group consisting of carbon, nitrogen, and boron.

Specific examples of the ligand L are provided, and include:

Compound 1

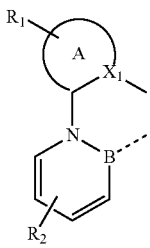

X is selected from the group consisting of S, NZ, O, Se, BZ, CZZ', and C=O. Z and Z' are independently selected from the group consisting of hydrogen, alkyl, and aryl.

Additionally, A may be selected from the group consisting of:

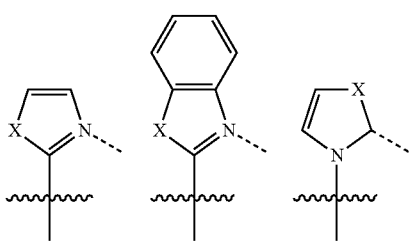

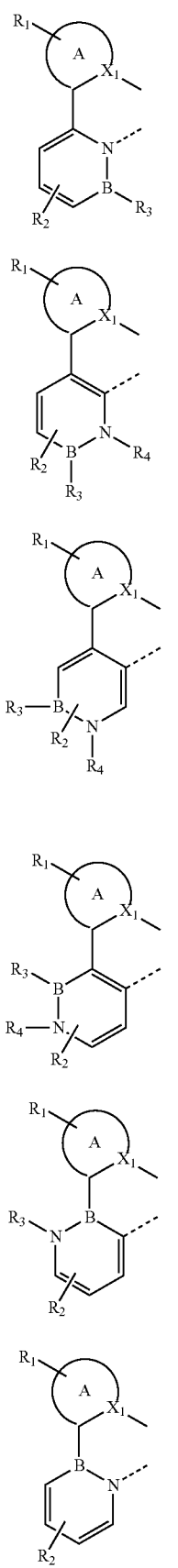
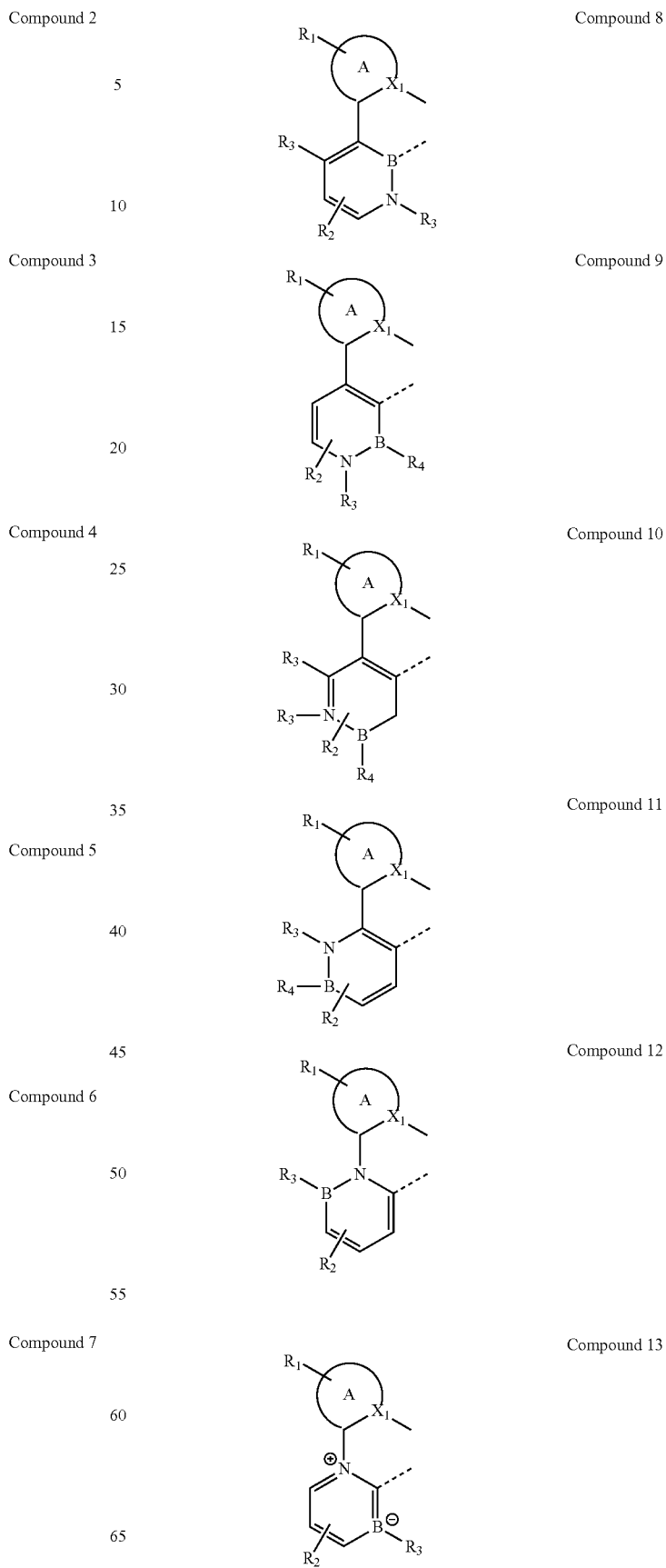

25
-continued
Compound 14
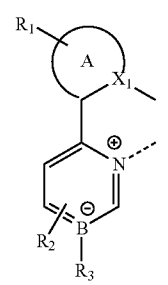
Compound 15
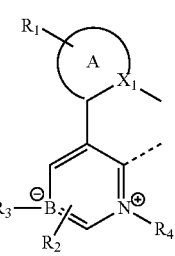
Compound 16
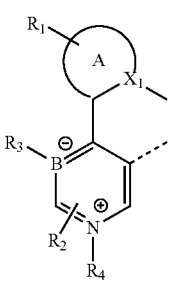
Compound 17
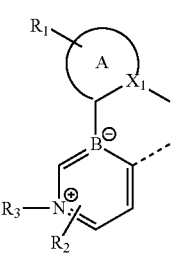
Compound 18
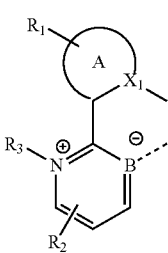
Compound 19
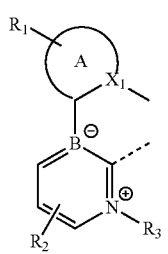
26
-continued
Compound 20
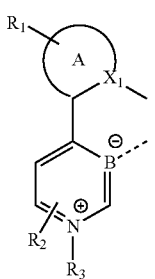
Compound 21
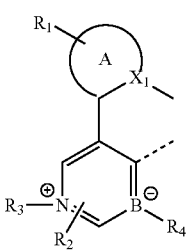
Compound 22
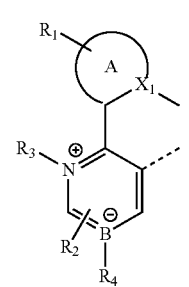
Compound 23
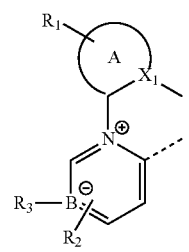
Compound 24
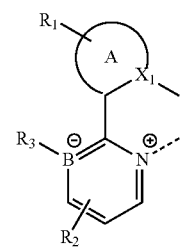
Compound 25
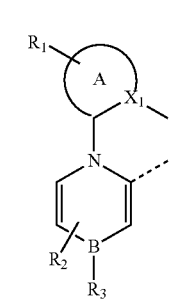

-continued
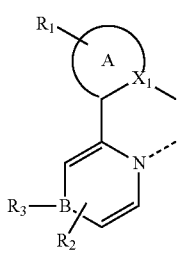
Compound 26
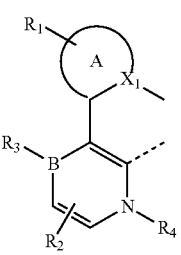
Compound 27
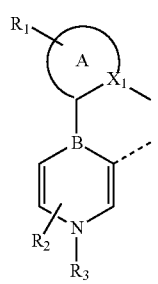
Compound 28
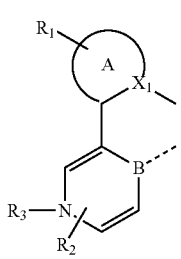
Compound 29
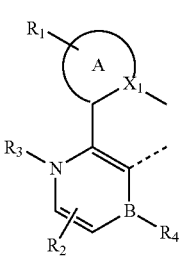
Compound 30
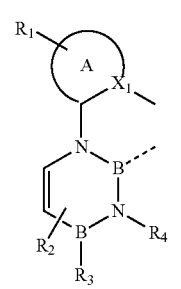
Compound 31
-continued
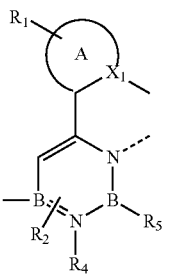
Compound 32
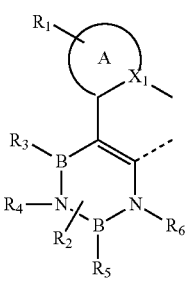
Compound 33
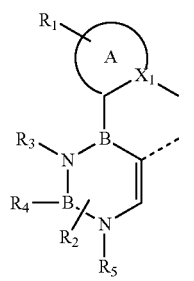
Compound 34
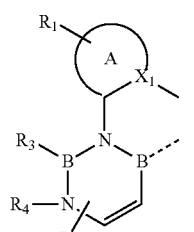
Compound 35
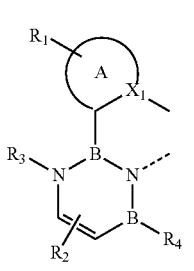
Compound 36
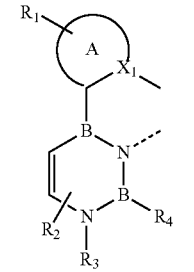
Compound 37

Compound 38
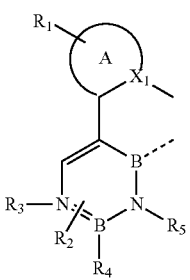
Compound 39
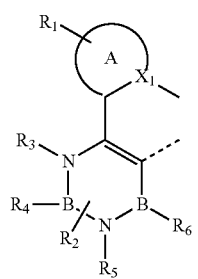
Compound 40
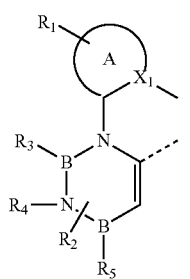
Compound 41
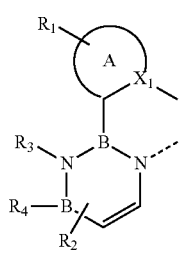
Compound 42
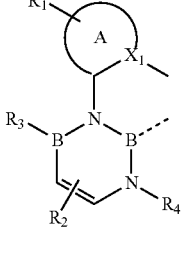
Compound 43
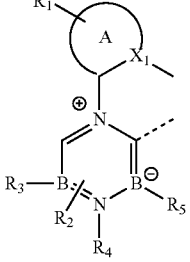
Compound 44
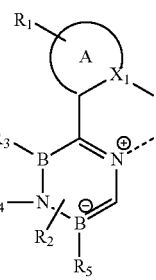
Compound 45
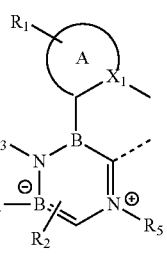
Compound 46
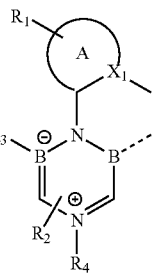
Compound 47
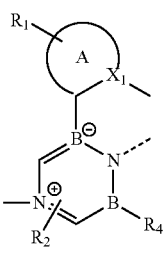
Compound 48
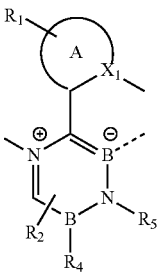
Compound 49
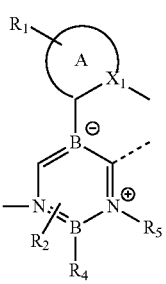

-continued
Compound 50
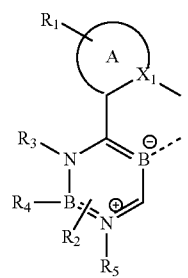
Compound 51
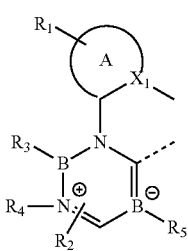
Compound 52
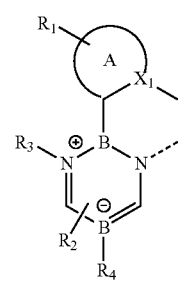
Compound 53
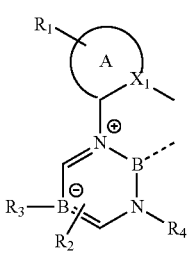
Compound 54
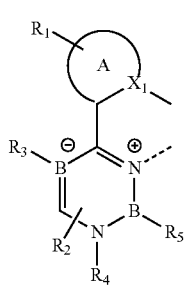
Compound 55
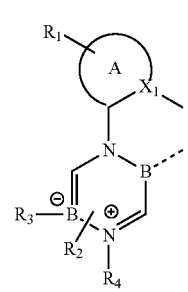
-continued
Compound 56
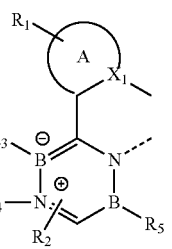
Compound 57
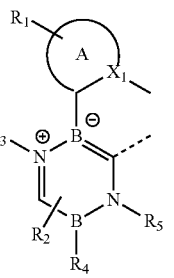
Compound 58
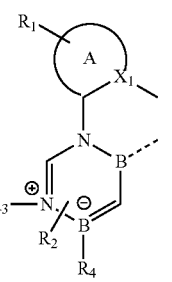
Compound 59
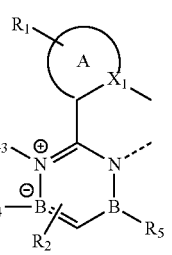
Compound 60
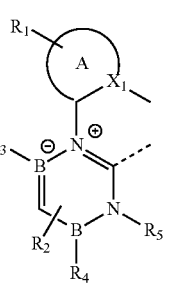
Compound 61
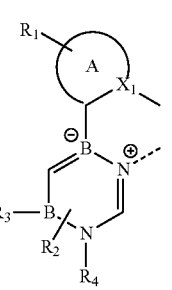

-continued
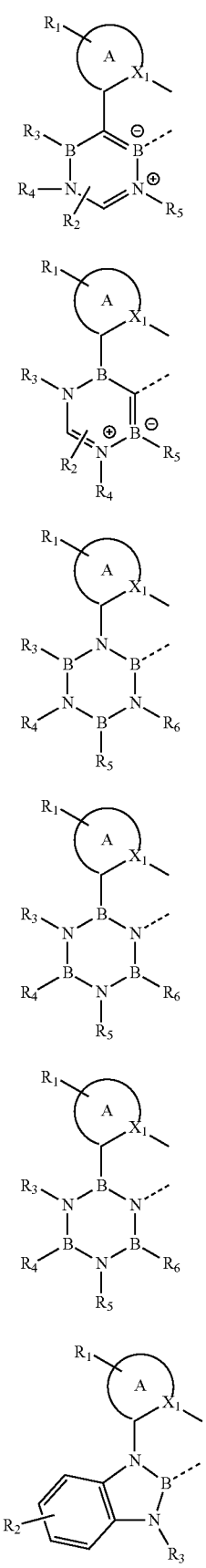
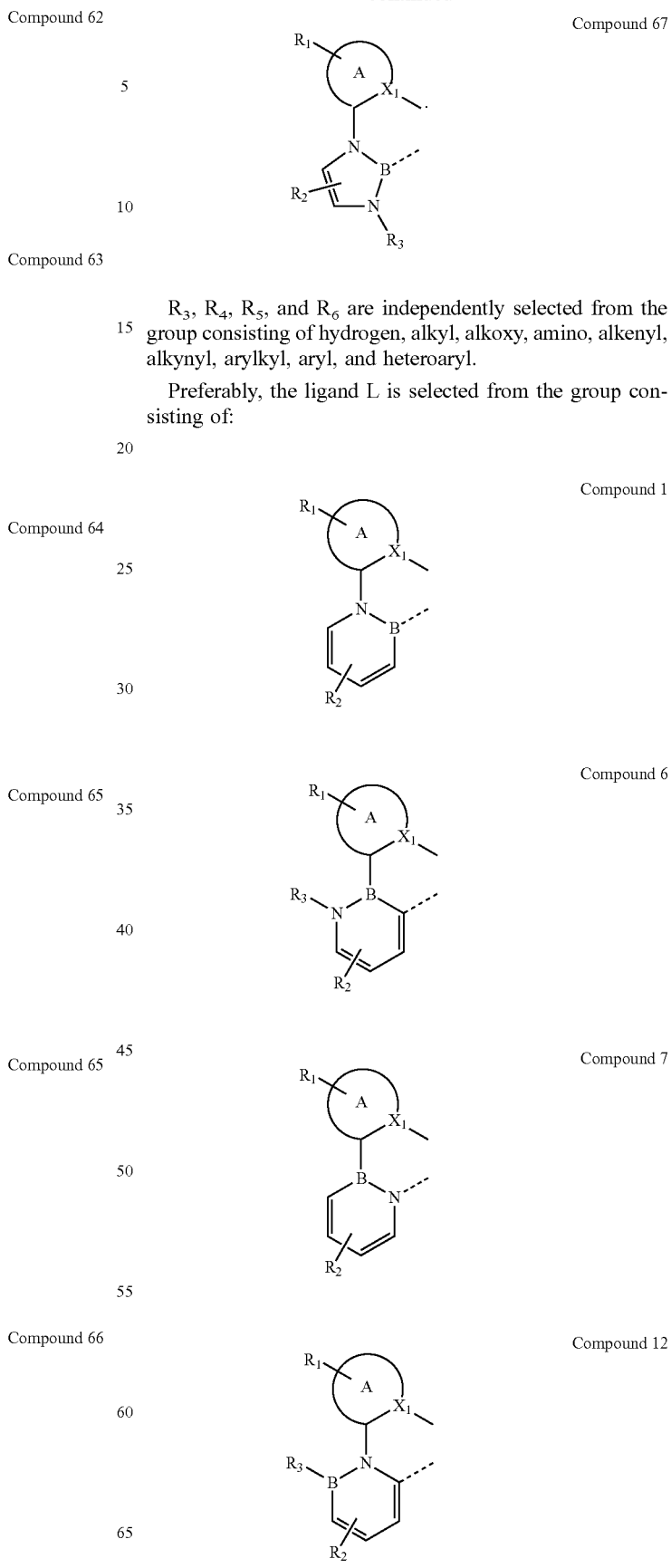
$R_3$, $R_4$, $R_5$, and $R_6$ are independently selected from the group consisting of hydrogen, alkyl, alkoxy, amino, alkenyl, alkynyl, arylkyl, aryl, and heteroaryl.
Preferably, the ligand L is selected from the group consisting of:

-continued

Compound 25

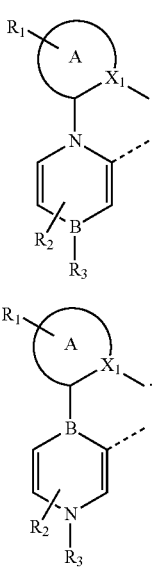

Compound 28

More preferably, the ligand L is:

Compound 25

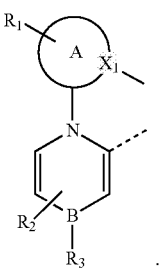

In one aspect, $R_2$ is hydrogen. Preferably, $R_3$ is selected from the group consisting of alkyl, alkoxy, amino, alkenyl, alkynyl, arylkyl, aryl, and heteroaryl. In particular, compounds containing minimal NH and BH groups on the ring may be preferred. Without being bound by theory, it is believed that NH and BH groups are very reactive. Therefore, compounds lacking or containing a minimal number of these groups on the ring may be more stable and thus preferred.

In one aspect, the ligand L is included in a homoleptic compound. In another aspect, the ligand L is included in a heteroleptic compound.

In a particular aspect, compounds having the formula $M^n(L)_a(U)_b(L'')_c$ are provided. n is the oxidation state of the metal M. The ligands may be combined in a variety of ways. In one aspect, the ligands may all be the same structure. In another aspect, the can all have a different structure. In yet another aspect, 2 of the ligands may be the same and one of the ligands may be different. In particular, the ligands L' and L'' can be phenylpyridine or phenylpyridine derivatives (i.e, FORMULA IV), boron-nitrogen containing heterocycles (i.e., FORMULA I), or other ligands.

In one aspect, n is 3. a is 1, 2, or 3. b is 0, 1, or 2. c is 0, 1, or 2. a+b+c is n. In one aspect, preferably a is 1. In another aspect, preferably a is 2. In compounds having the formula $M^n(L)_a(L')_b(L'')_c$ wherein a is 1 or 2, the compound is a heteroleptic compound. In yet another aspect, preferably a is 3. In compounds having the formula $M^n(L)_a(L')_b(L'')_c$ wherein a is 3, the compound is a homoleptic compound.

L' and L'' are independently selected from the group consisting of:

FORMULA I

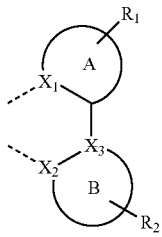

FORMULA IV

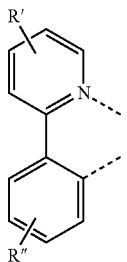

FORMULA V

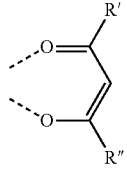

FORMULA VI

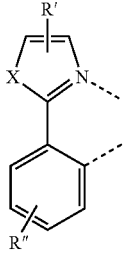

FORMULA VII

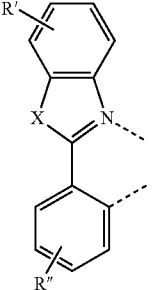

FORMULA VIII

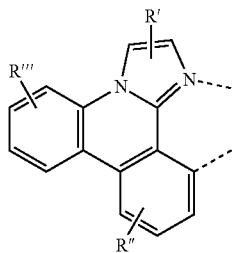

FORMULA IX

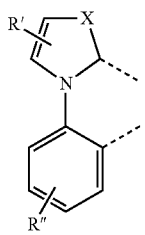

FORMULA X

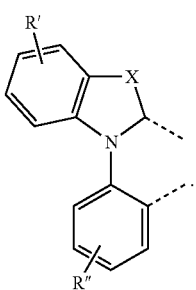

R', R" and R'" are independently selected from the group consisting of hydrogen, alkyl, alkoxy, amino, alkenyl, alkynyl, arylkyl, aryl, and heteroaryl. X is selected from the group consisting of S, NZ, O, Se, BZ, CZZ', and C=O. Z and Z' are independently selected from the group consisting of hydrogen, alkyl, and aryl.

Heteroleptic compounds comprising a phenylpyridine ligand, optionally substituted with a wide variety of substituents and/or heteroatoms, may be particularly useful. Thus, heteroleptic compounds having L' and/or L" which comprise a ligand structure having FORMULA IV may be beneficial. Preferably, L' and L" are independently selected from the group consisting of:

Compound 68

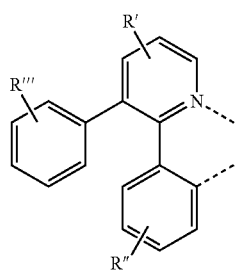

Compound 69

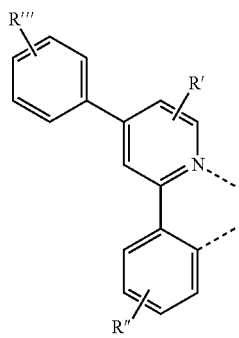

Compound 70

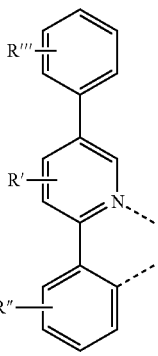

Compound 71

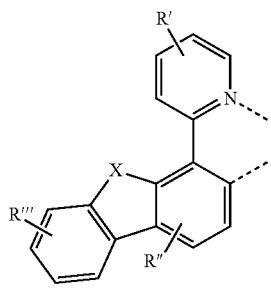

Compound 72

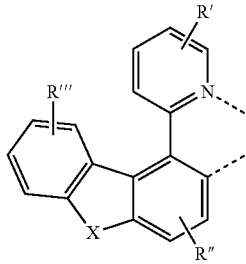

Compound 73

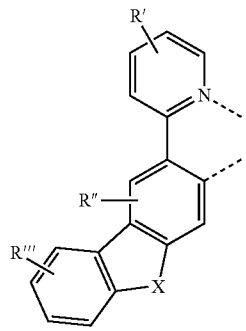

Compound 74

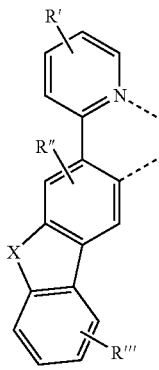

Compound 75
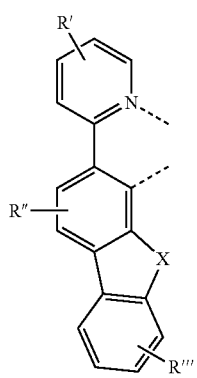
Compound 76
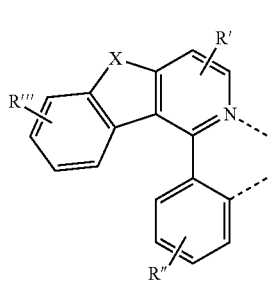
Compound 77
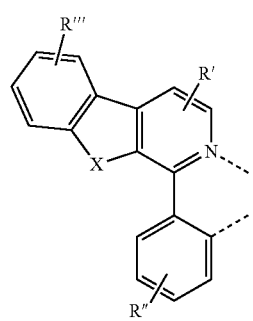
Compound 78
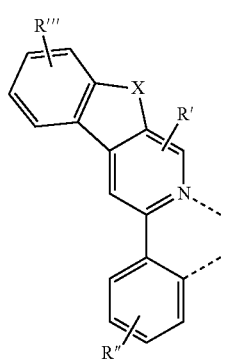
Compound 79
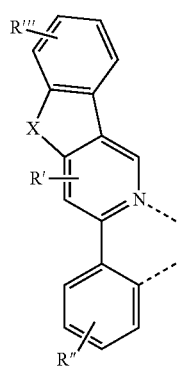
Compound 80
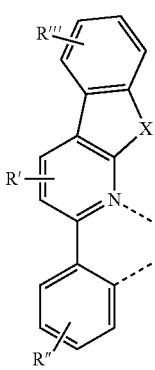
Compound 81
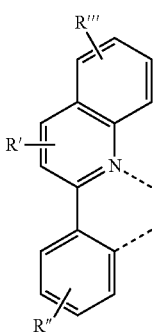
Compound 82
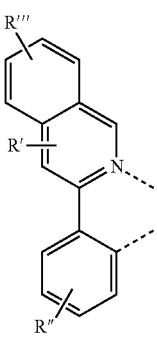

-continued

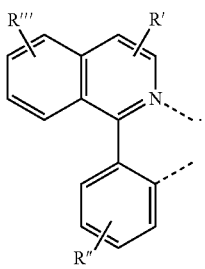
Compound 83

Ligands having the structure of Compound 68-Compound 83 may be further substituted, as described above. For some applications, compounds wherein substituents R', R", and R'" are hydrogen may be preferred.

The heteroleptic compounds and homoleptic compounds provided herein may be used in red, green and blue devices. In particular, the ligands L' and L" of heteroleptic compounds may influence the emissive properties of the compound and therefore the ligands L' and L" which are included in the compound may differ depending on the device in which the compound may be used (i.e., red, green, or blue). In particular, a heteroleptic compound having phenylimidazole as the ligand L' and/or L" may be especially useful in a blue device. A heteroleptic compound having phenylpyridine as the ligand L' and/or L" may be especially useful in a green device. A heteroleptic compound having phenylquinoline as the ligand L' and/or L" may be especially useful in a red device.

In one aspect, the compound is selected from the group consisting of:

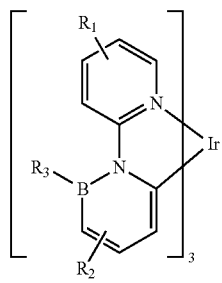
Compound 84G

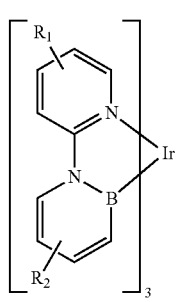
Compound 85G

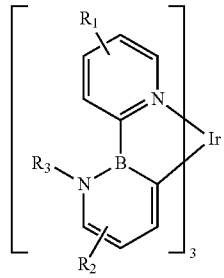
Compound 86G

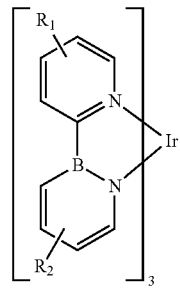
Compound 87G

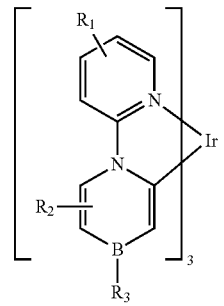
Compound 88G

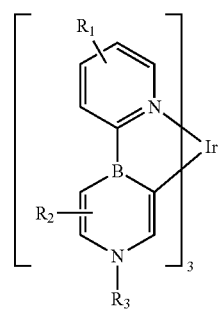
Compound 89G

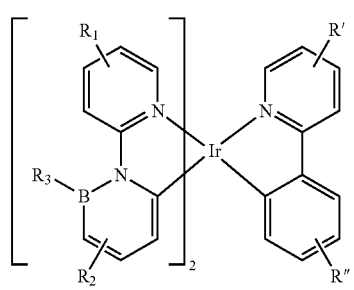
Compound 90G

-continued
Compound 91G
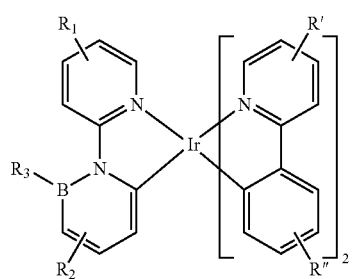
Compound 92G
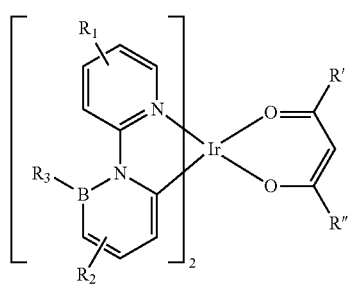
Compound 93G
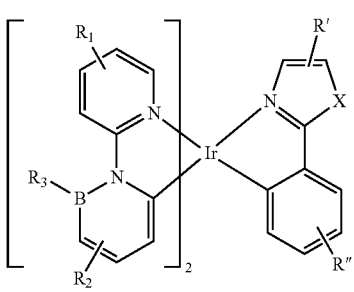
Compound 94G
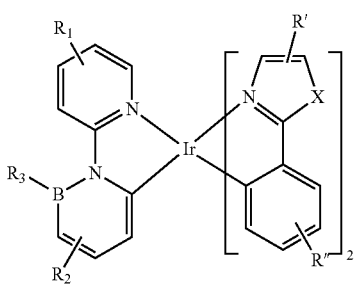
Compound 95G
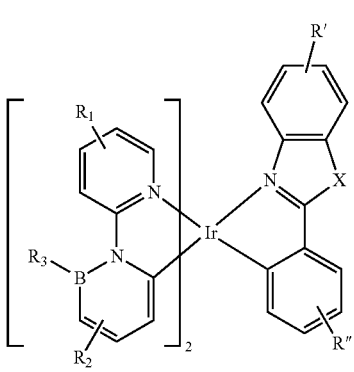
-continued
Compound 96G
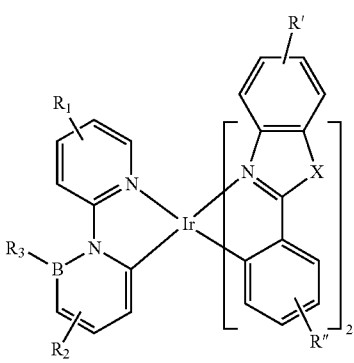
Compound 97G
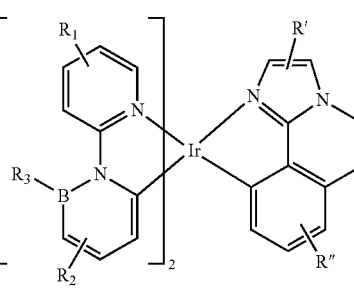
Compound 98G
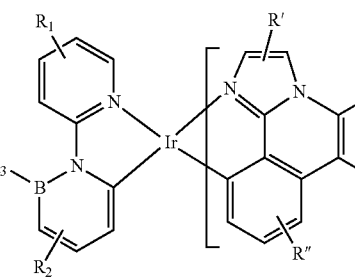
Compound 99G
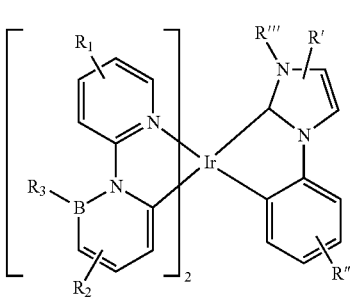
Compound 100G
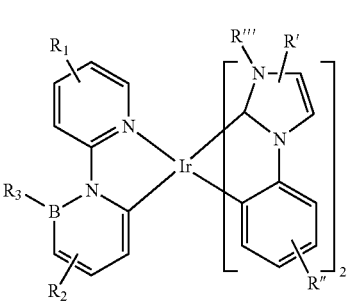

-continued
Compound 101G
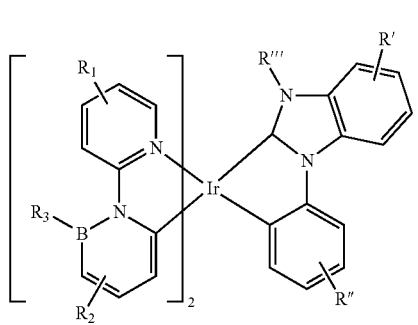
Compound 102G
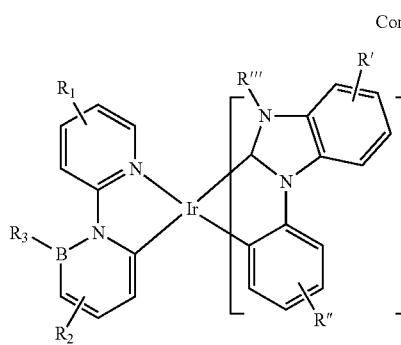
Compound 103G
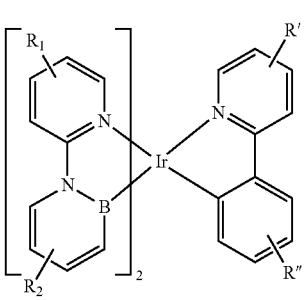
Compound 104G
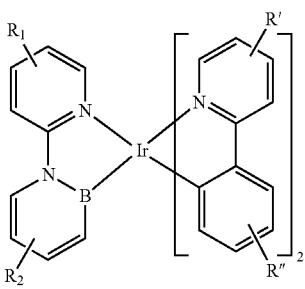
Compound 105G
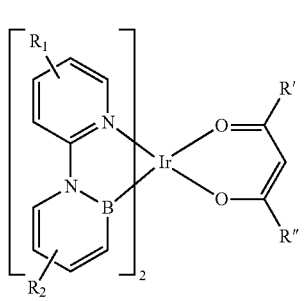
-continued
Compound 106G
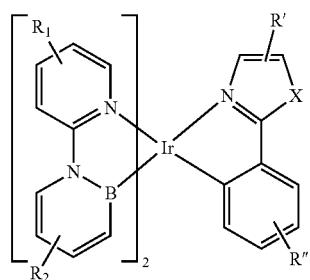
Compound 107G
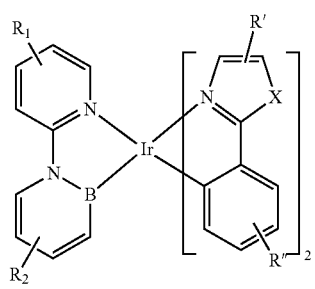
Compound 108G
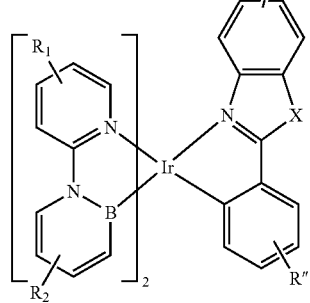
Compound 109G
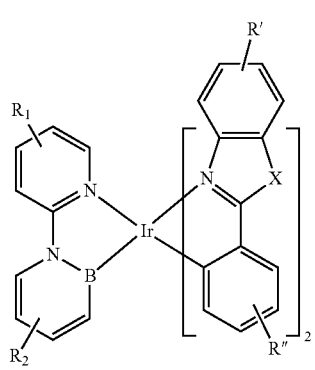
Compound 110G
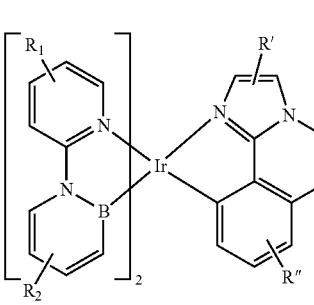

Compound 111G
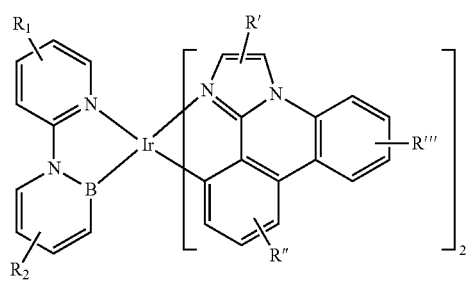
Compound 112G
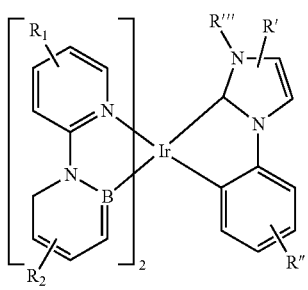
Compound 113G
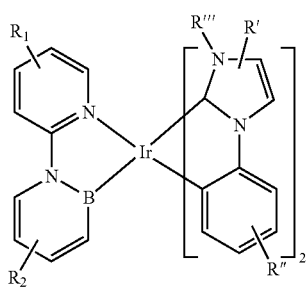
Compound 114G
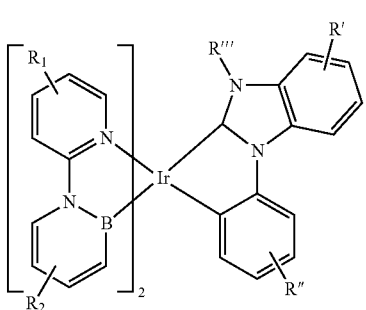
Compound 115G
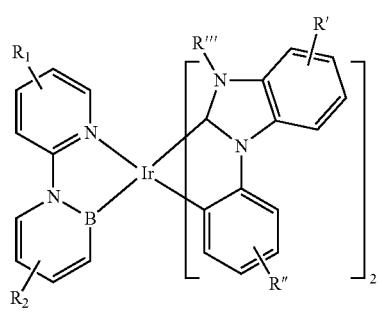
Compound 116G
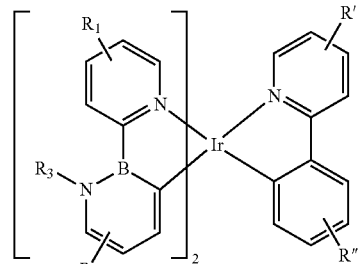
Compound 117G
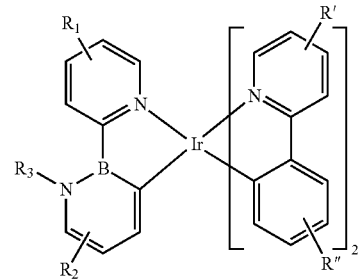
Compound 118G
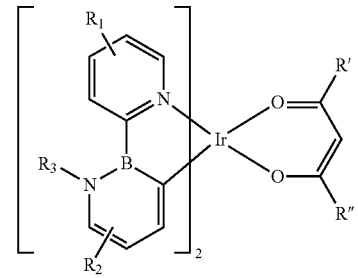
Compound 119G
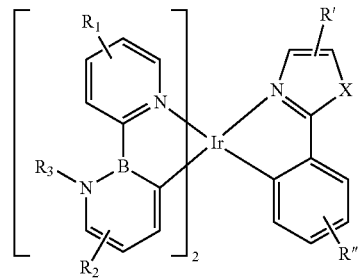
Compound 120G
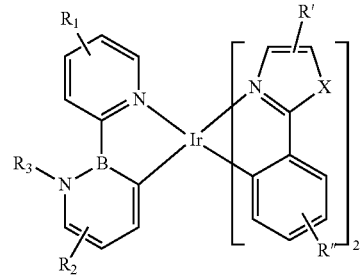

Compound 121G
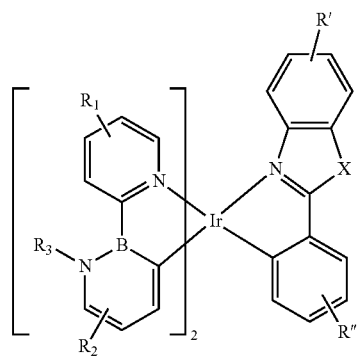
Compound 122G
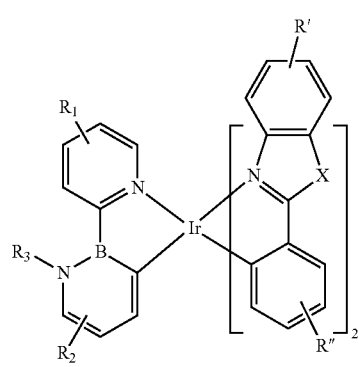
Compound 123G
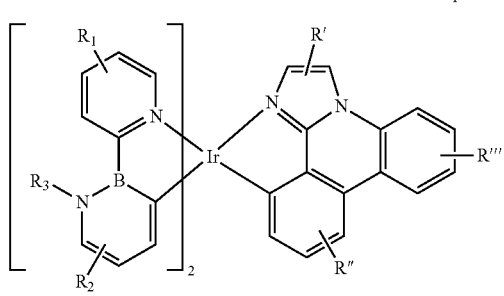
Compound 124G
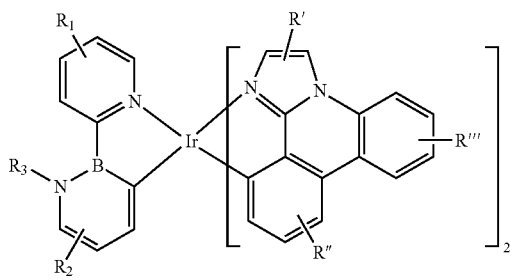
Compound 125G
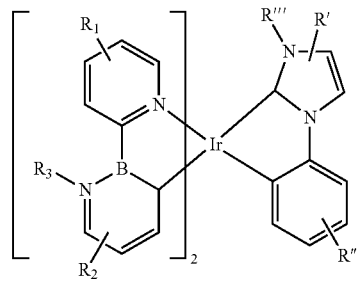
Compound 126G
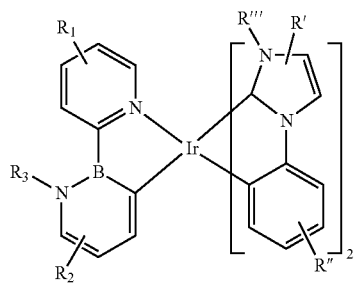
Compound 127G
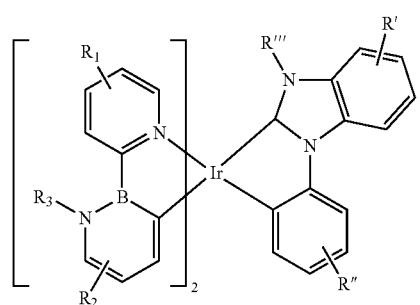
Compound 128G
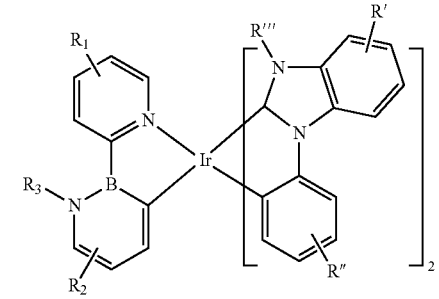
Compound 129G
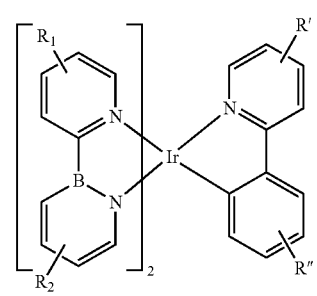
Compound 130G
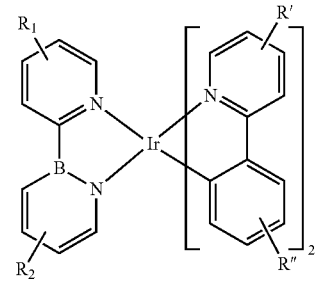

-continued
Compound 131G
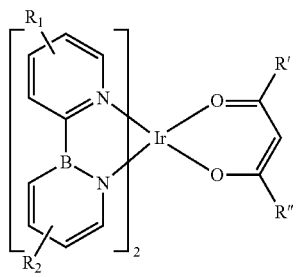
Compound 132G
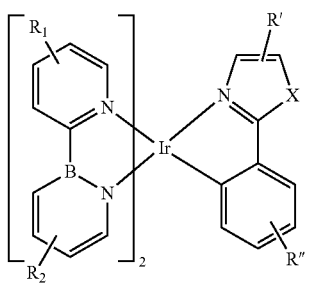
Compound 133G
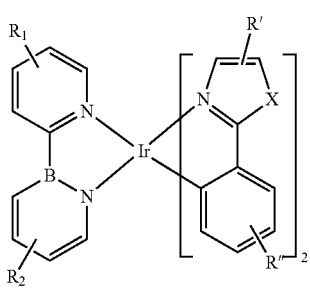
Compound 134G
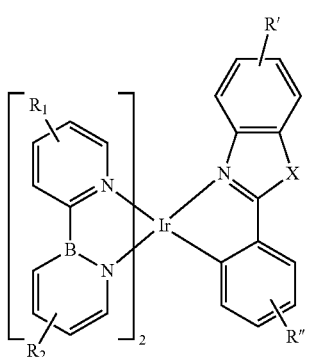
Compound 135G
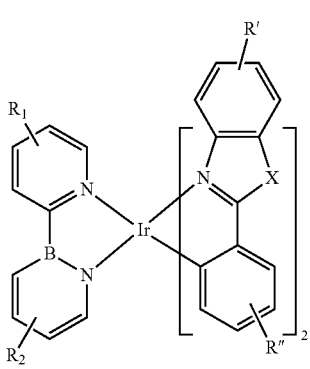
-continued
Compound 136G
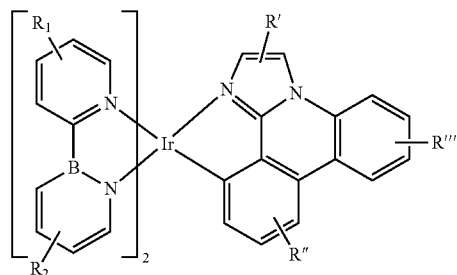
Compound 137G
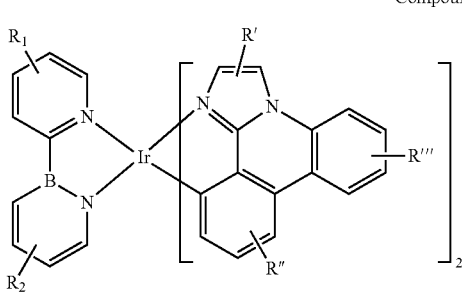
Compound 138G
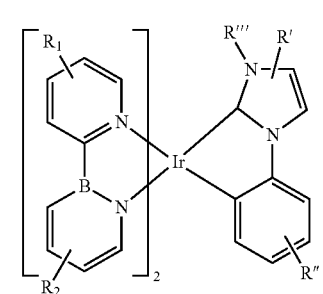
Compound 139G
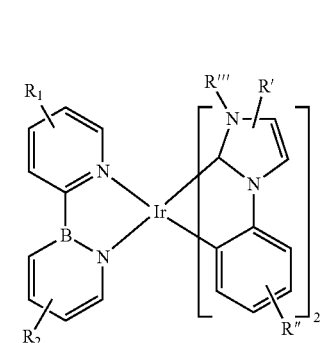
Compound 140G
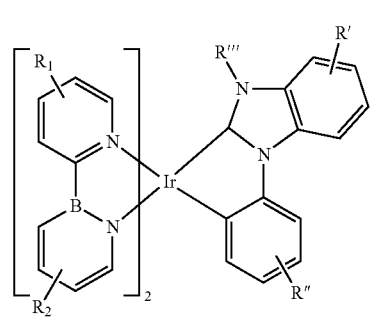

Compound 141G
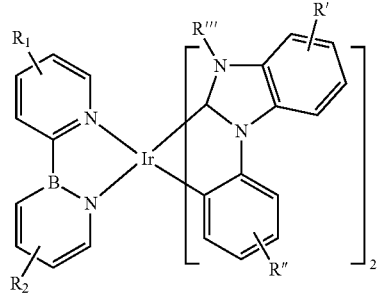
Compound 142G
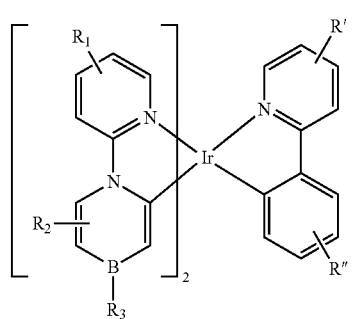
Compound 143G
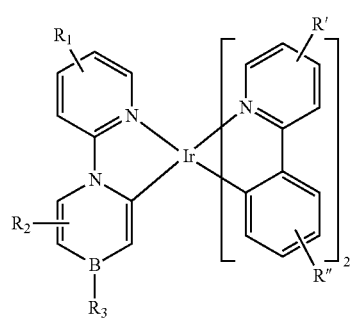
Compound 144G
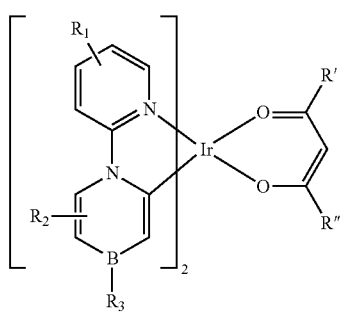
Compound 145G
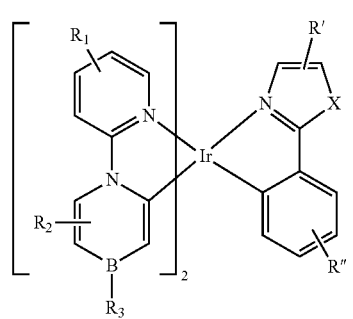
Compound 146G
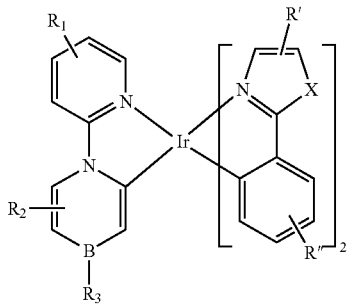
Compound 147G
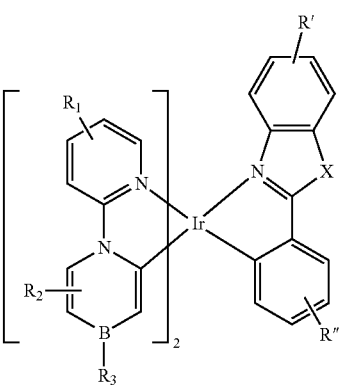
Compound 148G
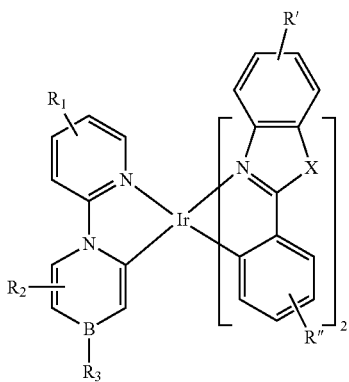
Compound 149G
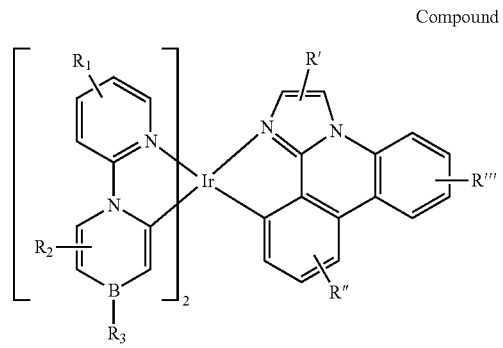

-continued
Compound 150G
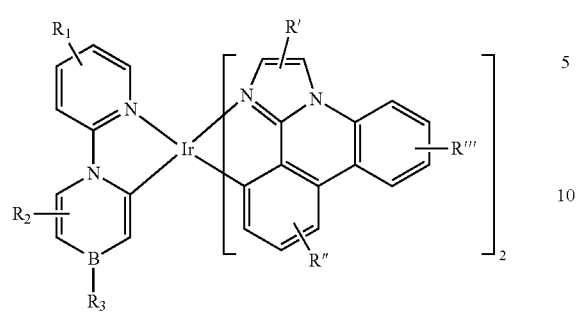
Compound 151G
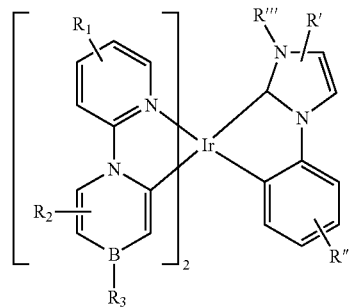
Compound 152G
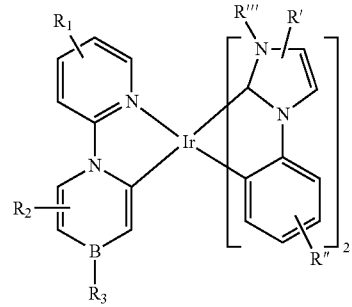
Compound 153G
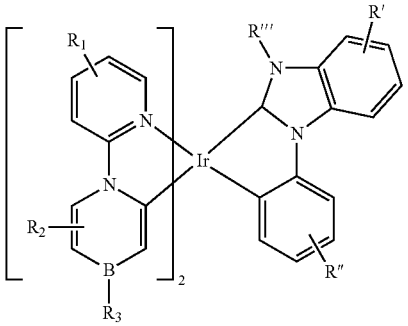
Compound 154G
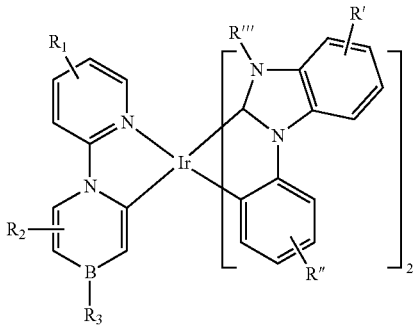
-continued
Compound 155G
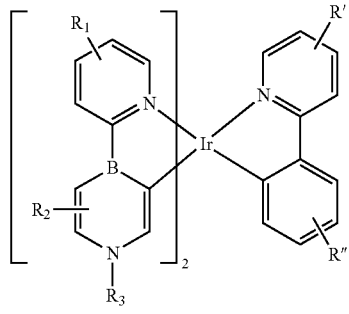
Compound 156G
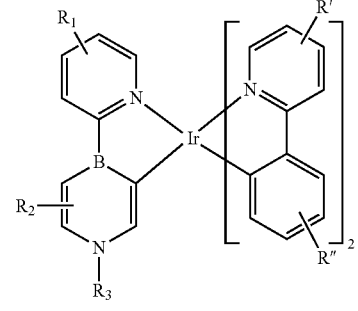
Compound 157G
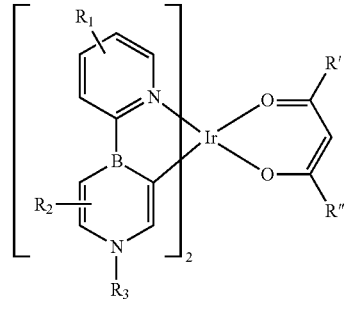
Compound 158G
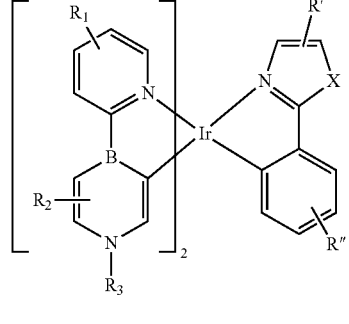
Compound 159G
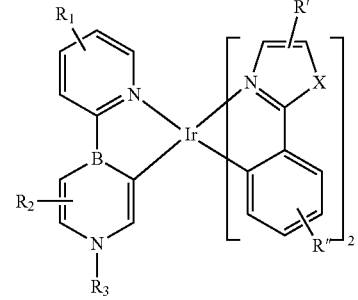

Compound 160G
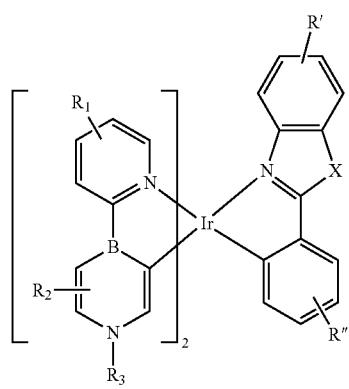
Compound 161G
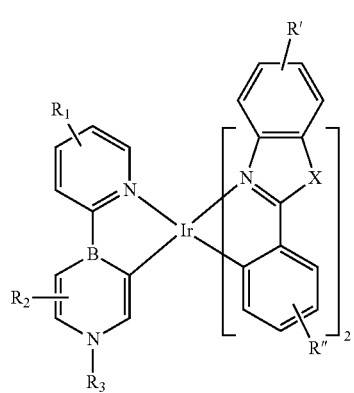
Compound 162G
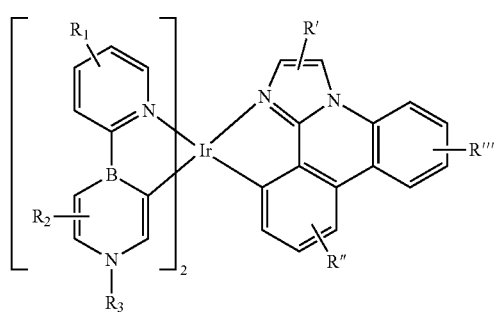
Compound 163G
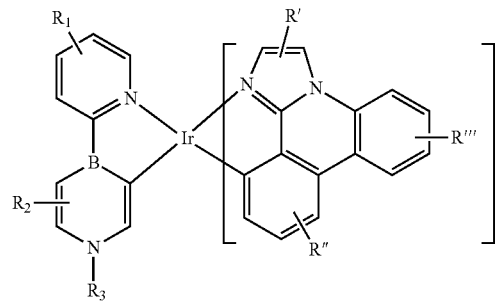
Compound 164G
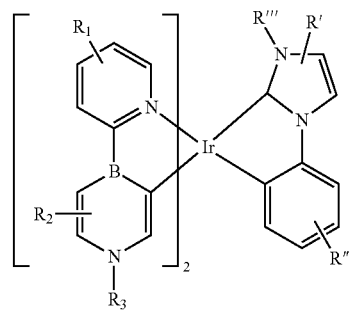
Compound 165G
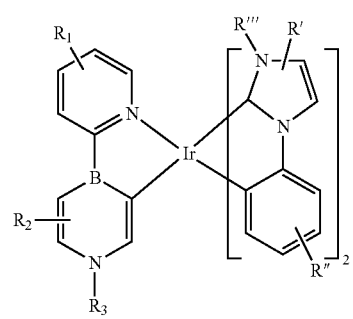
Compound 166G
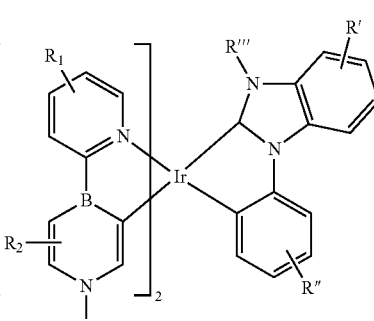
Compound 167G
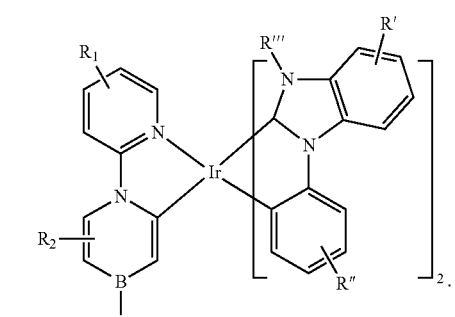
More particularly, the compound may be selected from the group consisting of:

Compound 84
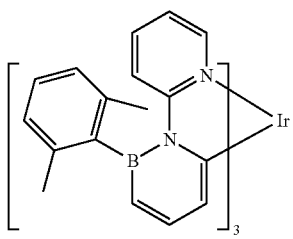
Compound 85
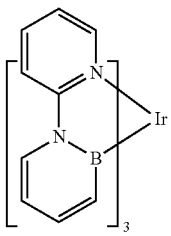
Compound 86
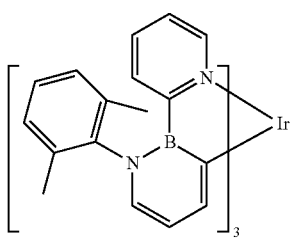
Compound 87
Compound 88
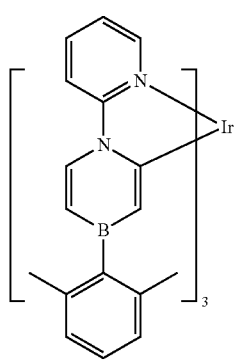
Compound 89
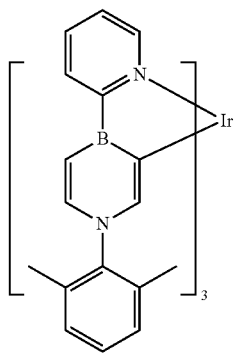
Compound 90
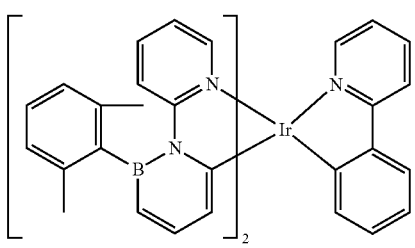
Compound 91
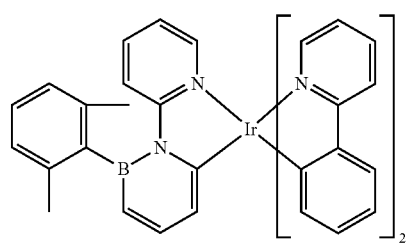
Compound 92
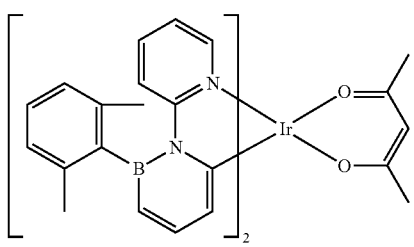
Compound 93
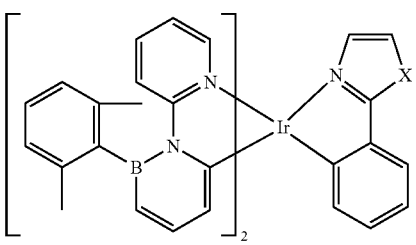
Compound 94
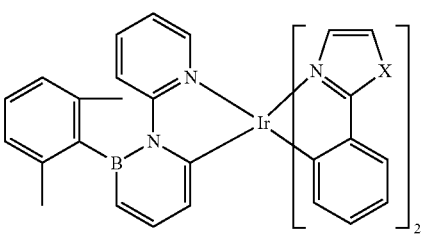

-continued
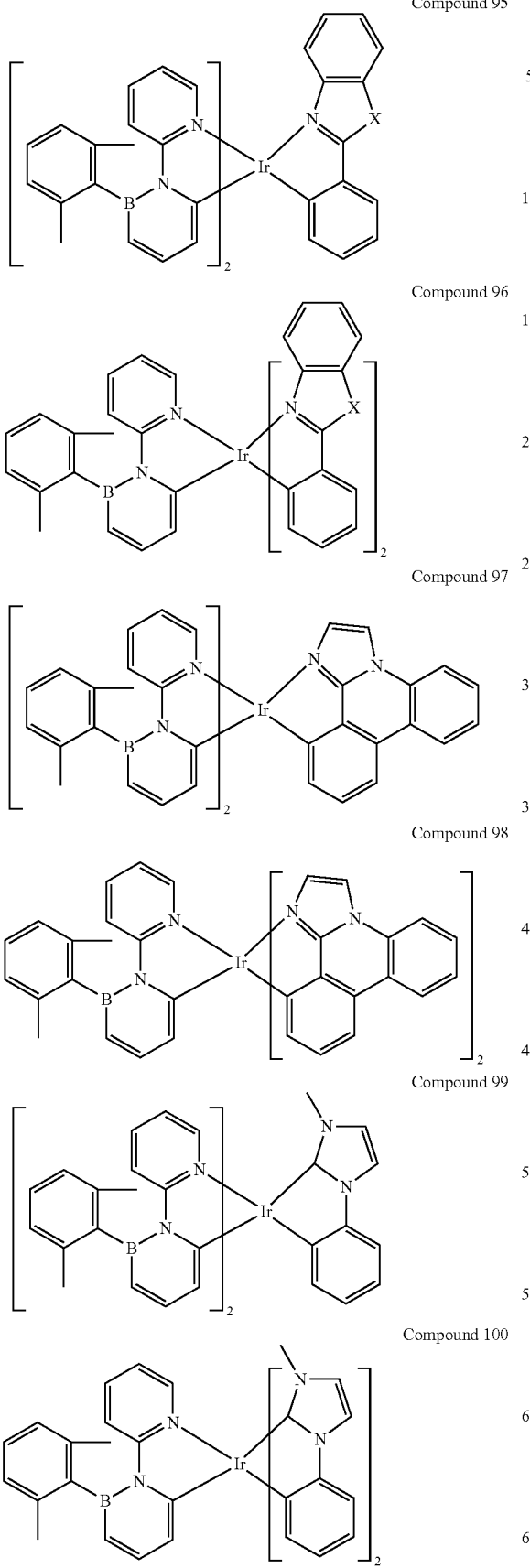
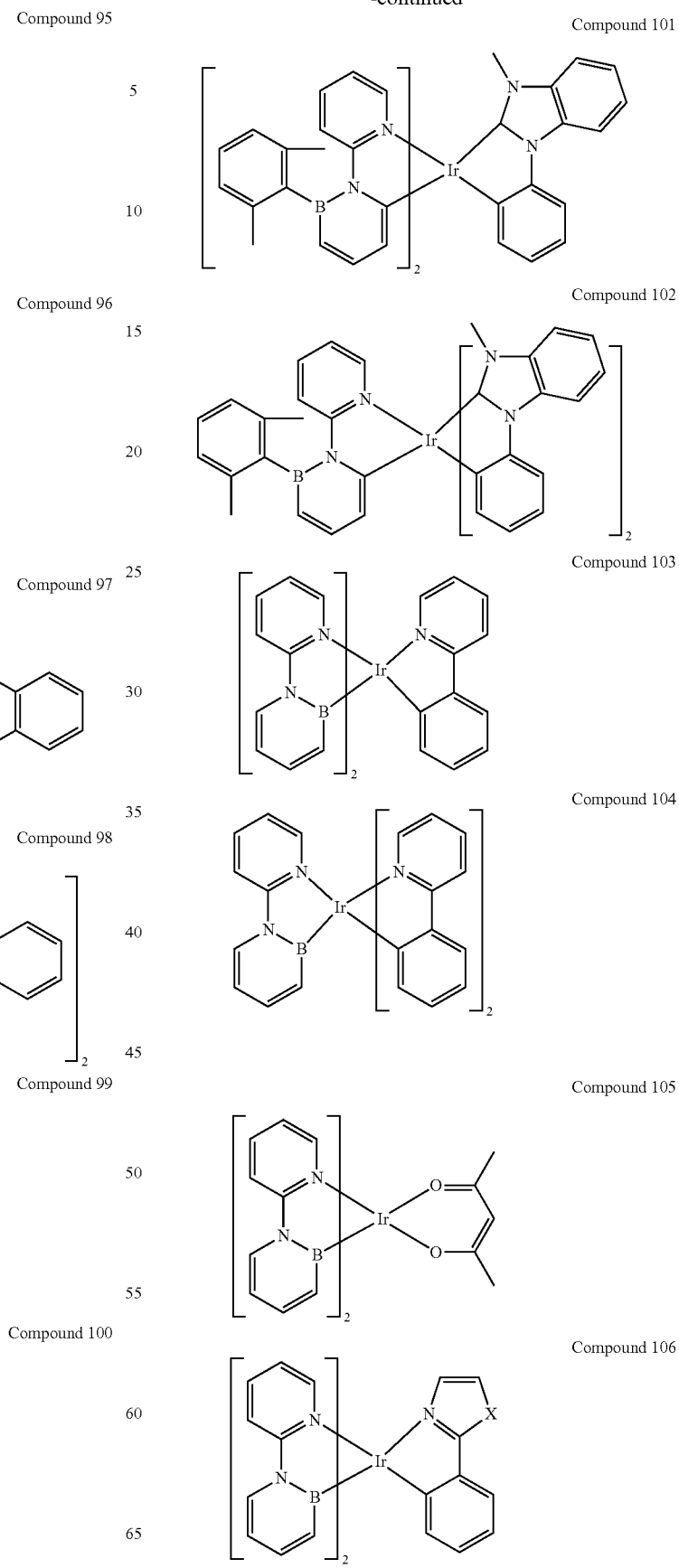

Compound 107
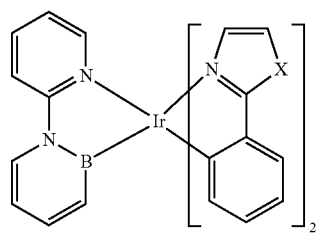
Compound 108
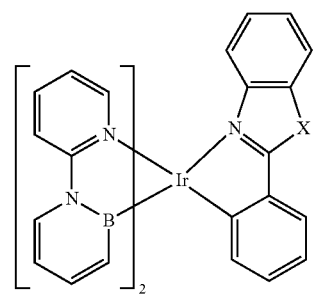
Compound 109
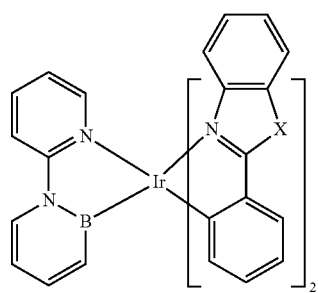
Compound 110
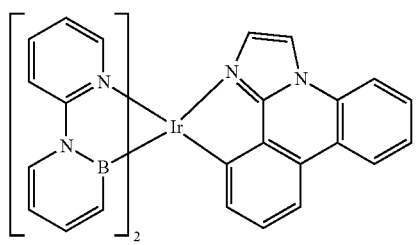
Compound 111
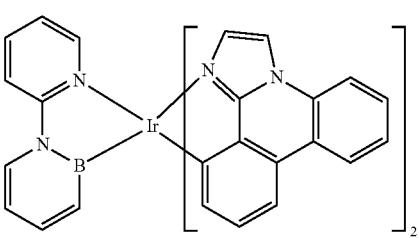
Compound 112
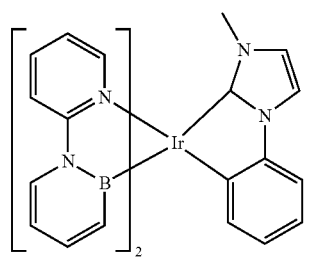
Compound 113
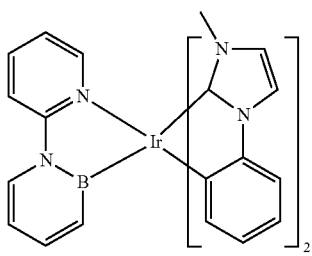
Compound 114
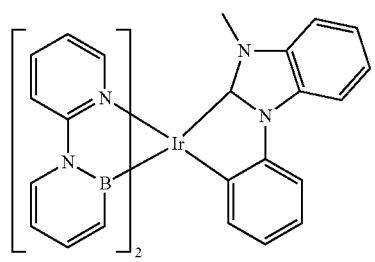
Compound 115
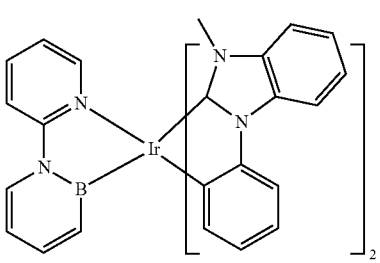
Compound 116
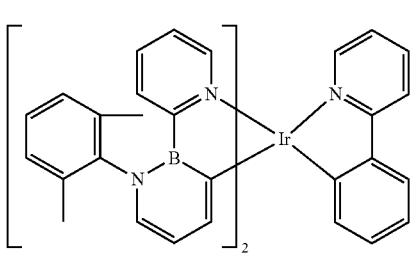
Compound 117
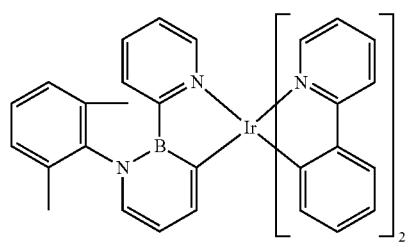
Compound 118
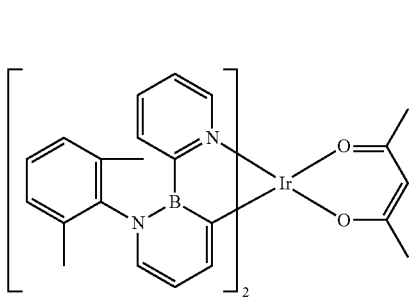

Compound 119
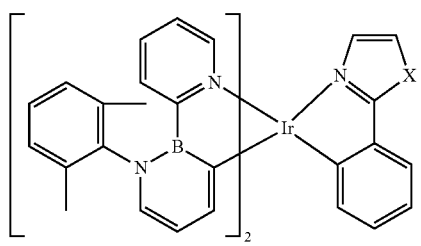
Compound 120
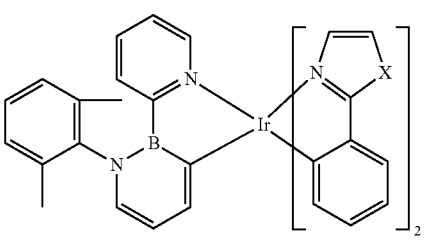
Compound 121
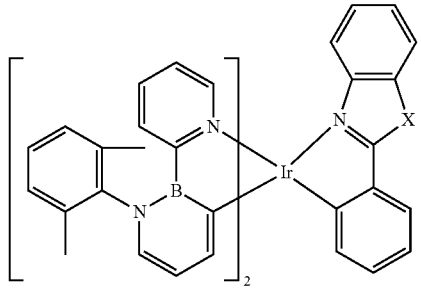
Compound 122
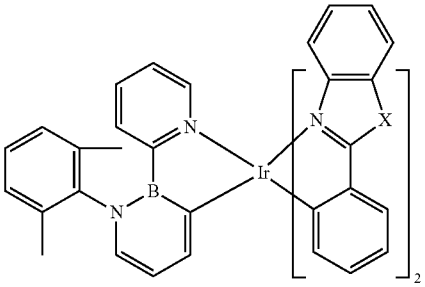
Compound 123
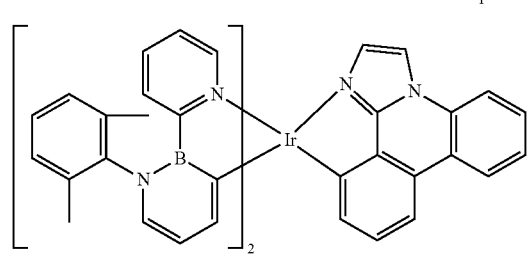
Compound 124
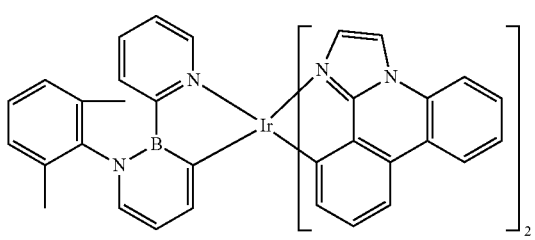
Compound 125
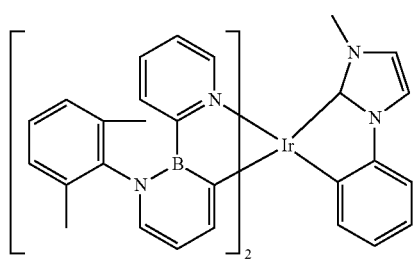
Compound 126
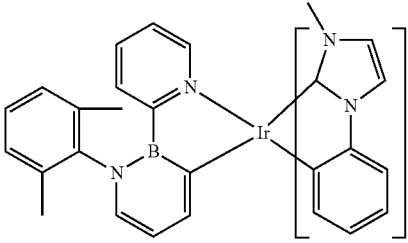
Compound 127
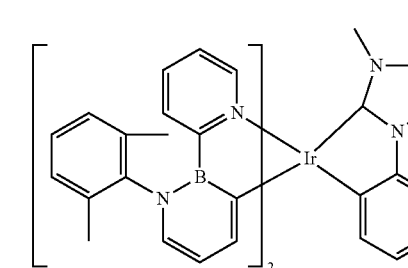
Compound 128
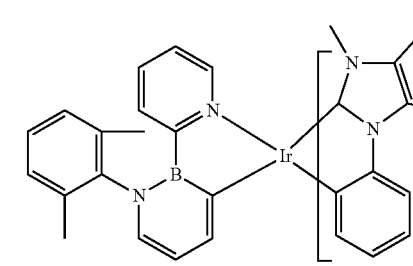
Compound 129
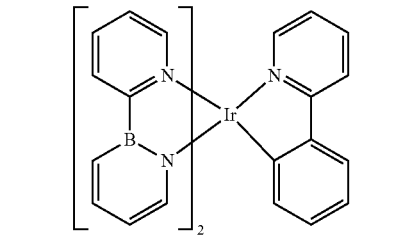
Compound 130

Compound 131 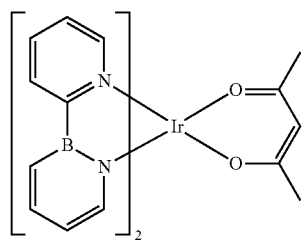
Compound 132 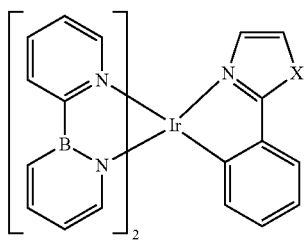
Compound 133 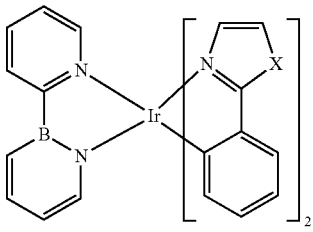
Compound 134 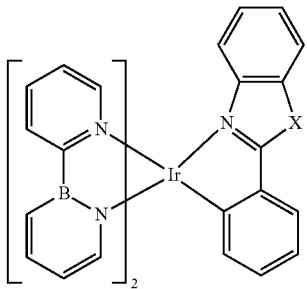
Compound 135 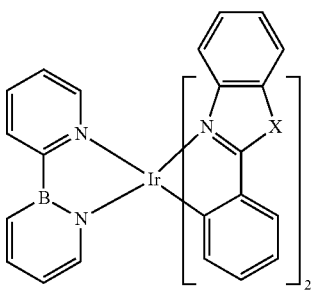
Compound 136 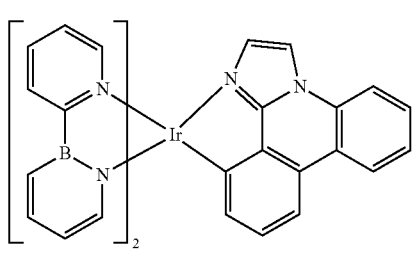
Compound 137 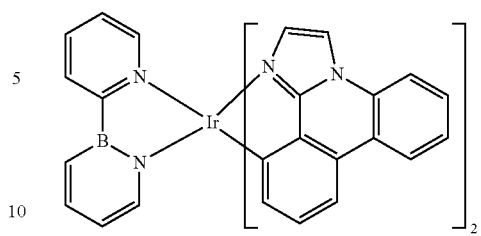
Compound 138 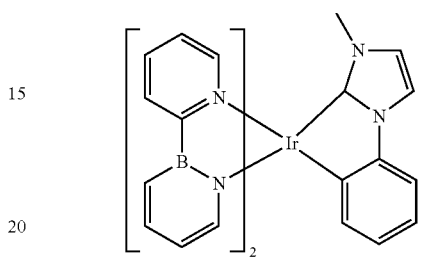
Compound 139 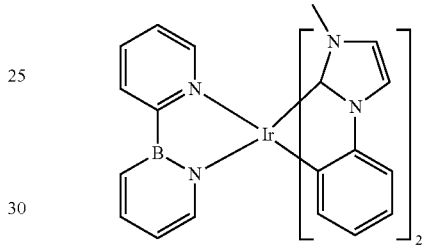
Compound 140 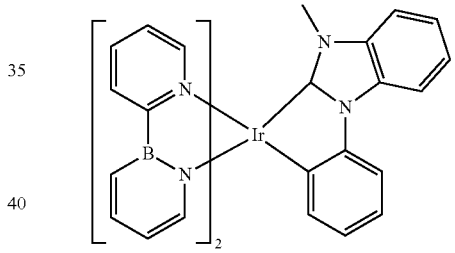
Compound 141 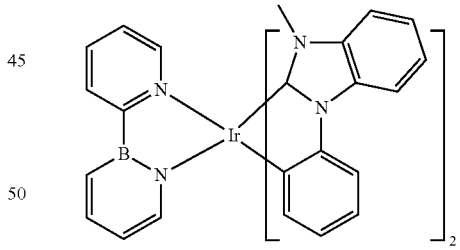
Compound 142 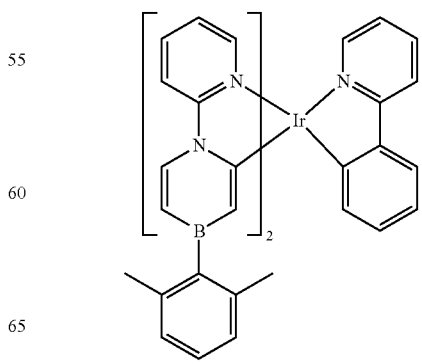

-continued
Compound 143
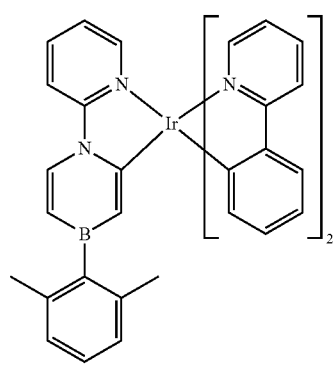
Compound 144
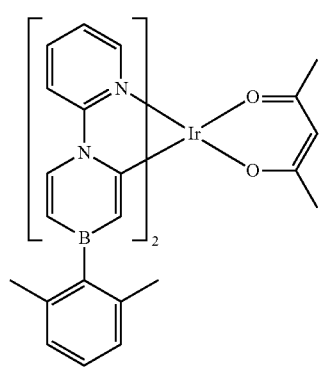
Compound 145
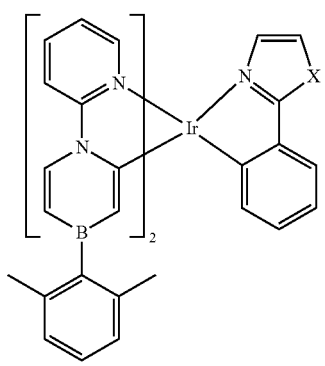
Compound 146
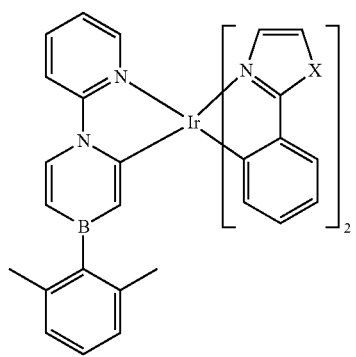
-continued
Compound 147
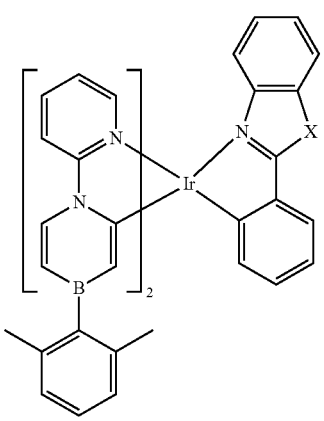
Compound 148
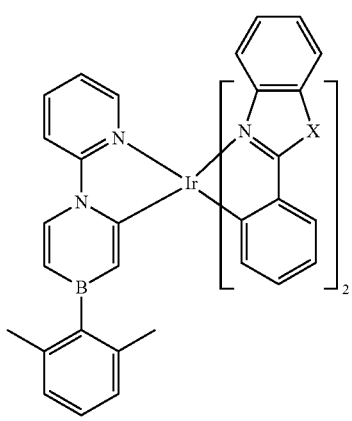
Compound 149
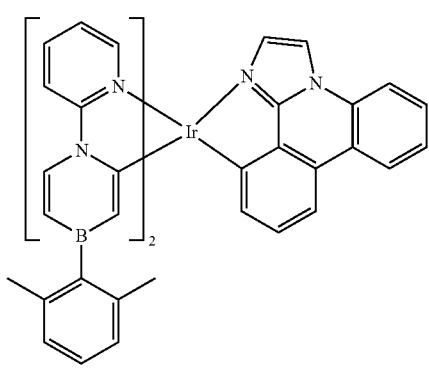
Compound 150
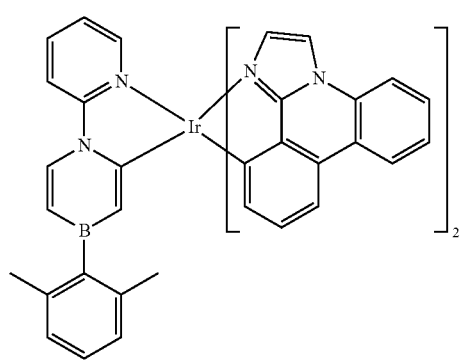

Compound 151
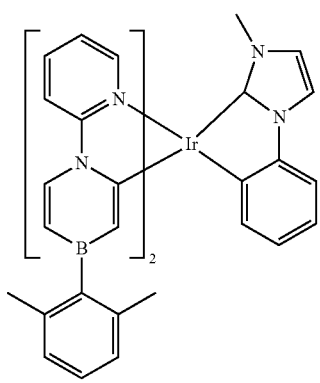
Compound 152
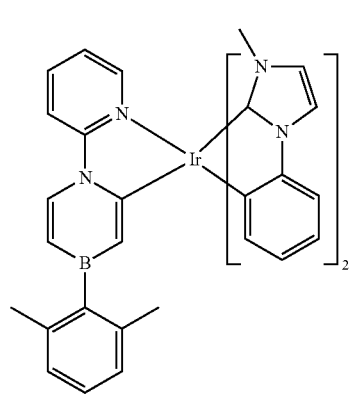
Compound 153
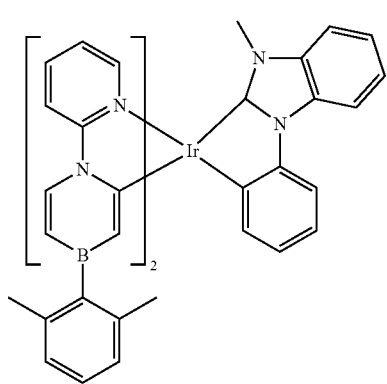
Compound 154
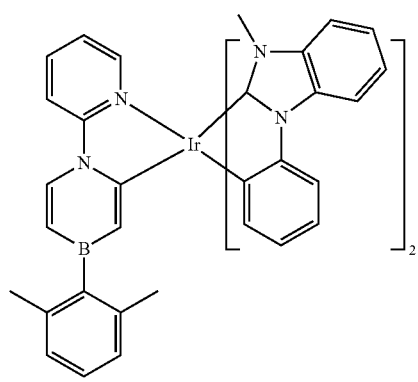
Compound 155
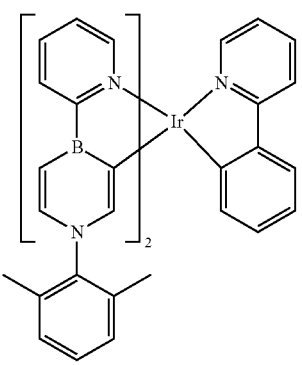
Compound 156
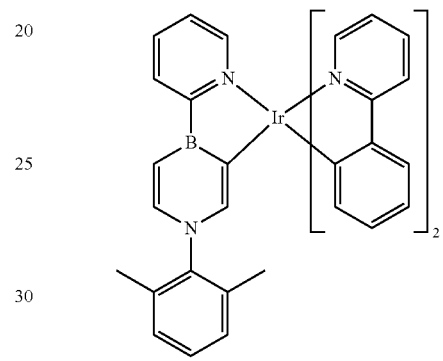
Compound 157
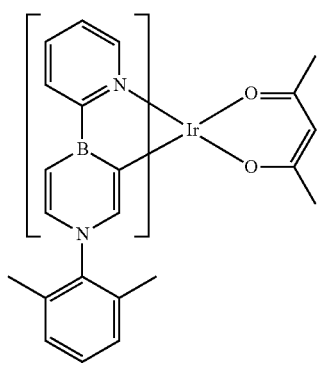
Compound 158
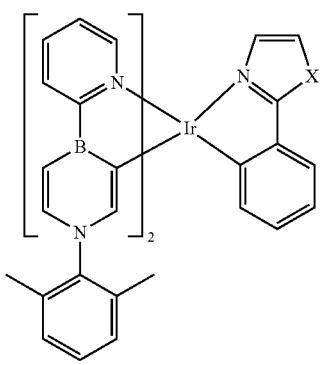

-continued
Compound 159
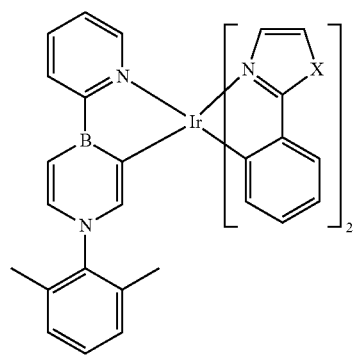
Compound 160
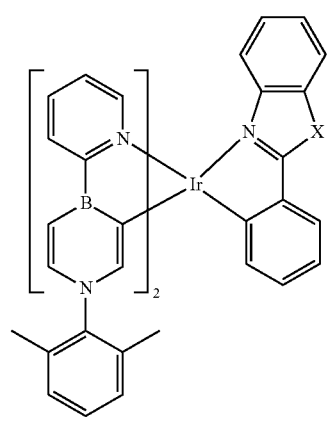
Compound 161
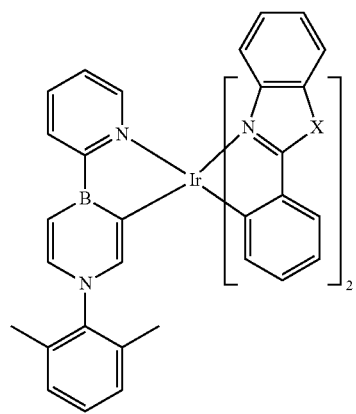
Compound 162
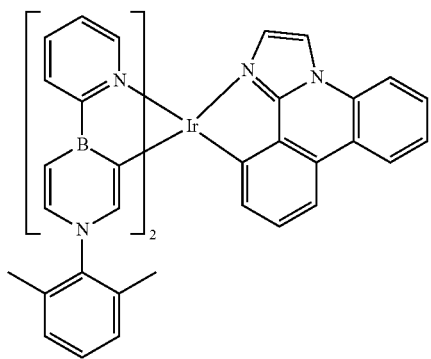
-continued
Compound 163
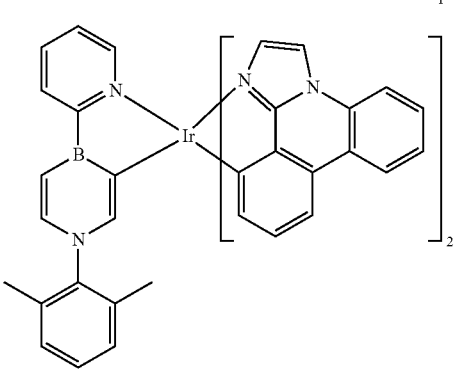
Compound 164
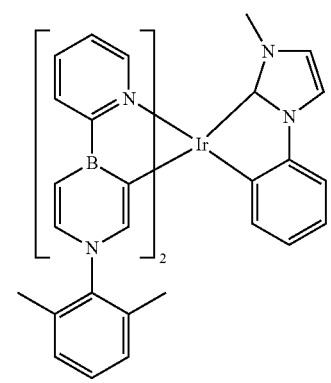
Compound 165
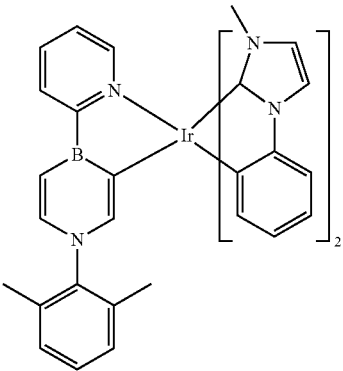
Compound 166
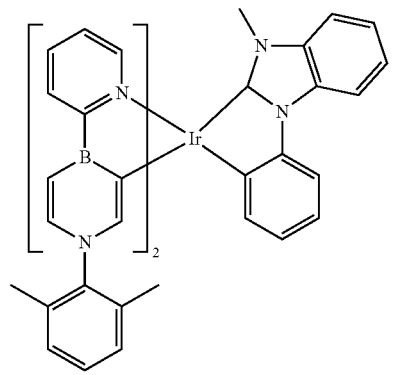

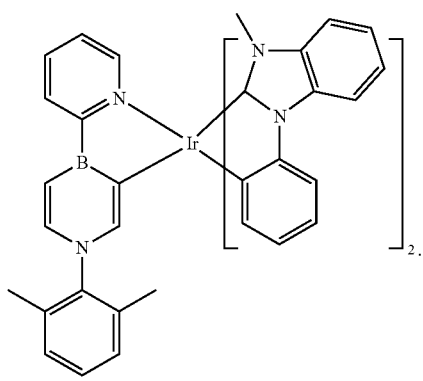

Compound 167

In one particular aspect, the compound is:

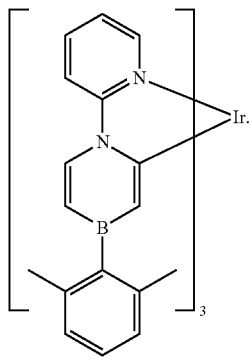

Compound 88

In another particular aspect, the compound is:

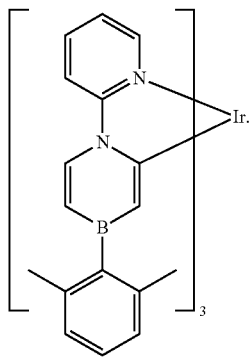

Compound 89

Additional compounds comprising a boron-nitrogen heterocycle are provided, such compounds having the formula:

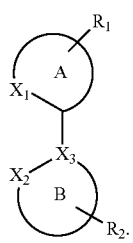

FORMULA XI

A and B may represent a 5-membered or 6-membered carbocycle or heterocycle. $X_1$ is N or NR. $X_2$ and $X_3$ are independently selected from the group consisting of carbon, nitrogen, and boron. B is a boron-nitrogen heterocycle. R, $R_1$ and $R_2$ represent mono, di, tri, or tetra substitutions. R, $R_1$ and $R_2$ are independently selected from the group consisting of hydrogen, alkyl, alkoxy, amino, alkenyl, alkynyl, arylkyl, aryl, and heteroaryl.

Additionally, an organic light emitting device is provided. The device comprises an anode, a cathode, and an organic layer disposed between the anode and the cathode. The organic layer further comprises a compound comprising a ligand L having the structure FORMULA I, as discussed above.

Selections for the rings, metal, substituents, and ligands described as preferred for compounds comprising a ligand L having FORMULA I are also preferred for use in a device that contains a compound comprising a ligand L having FORMULA I. These selections include those for rings A and B, the metal M, the substituents $X_1$-$X_3$, the substituents $R_1$-$R_6$, R', R", R''', and the combination and/or incorporation of ligands L' and L" into an organometallic complex.

Specific examples of the ligand having FORMULA I are provided, and include a ligand L selected from the group consisting of Compound 1-Compound 67. Preferably, the ligand L is selected from the group consisting of Compound 1, Compound 6, Compound 7, Compound 12, Compound 25, and Compound 28. More preferably, the ligand L is Compound 25. In particular, the substituent $R_2$ of Compound 25 may be hydrogen.

In a particular aspect, devices are provided wherein the device containing a compound having the formula $M''(L)_a(U)_b(L'')_c$. n is the oxidation state of the metal M. a is 1, 2, or 3. b is 0, 1, or 2. c is 0, 1, or 2. a+b+c is n. In one aspect, preferably a is 1. In another aspect, preferably a is 2. In yet another aspect, preferably a is 3. L' and L" are independently selected from the group consisting of FORMULA I, FORMULA IV, FORMULA V, FORMULA VI, FORMULA VII, FORMULA VIII, FORMULA IX, and FORMULA X, as discussed above. In particular, the ligands L' and L" are independently selected from the group consisting of Compound 68-Compound 83.

Devices containing particular boron-nitrogen heterocyclic compounds are also provided. Examples of the particular compounds include compounds selected from the group consisting of Compound 84G-Compound 167G. Additionally, devices are provided which contain a compound comprising a specific boron-nitrogen containing heterocycle, the compound is selected from the group consisting of Compound 84-Compound 167.

Devices having certain structures are also provided. In particular, devices are provided wherein the organic layer is an emissive layer and the compound comprising the ligand L having FORMULA I is an emitting dopant. Preferably, the organic layer further comprises a host containing a benzene, carbazole, dibenzofuran, dibenzothiophene, dibenzoselenophene, naphthalene, triphenylene, or biphenyl moiety.

A consumer product comprising a device is also provided. The device comprises an anode, a cathode, and an organic layer, disposed between the anode and the cathode. The organic layer comprises a compound comprising a ligand L having the formula of FORMULA I, Selections for the rings, metal, substituents, and ligands described as preferred for compounds comprising a ligand L having FORMULA I are also preferred for use in a consumer product comprising a device that contains a compound comprising a ligand L having FORMULA I. These selections include those for rings A and B, the metal M, the substituents $X_1$-$X_3$, the substituents $R_1$-$R_6$, R', R", R''', and the combination and/or incorporation of ligands L' and L" into an organometallic complex.

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 3 below. Table 3 lists non-limiting classes of materials, non-limiting examples of compounds for each class, and references that disclose the materials.

HIL/HTL:

A hole injecting/transporting material to be used in the present invention is not particularly limited, and any compound may be used as long as the compound is typically used as a hole injecting/transporting material. Examples of the material include, but not limit to: a phthalocyanine or porphryin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and sliane derivatives; a metal oxide derivative, such as MoO$_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

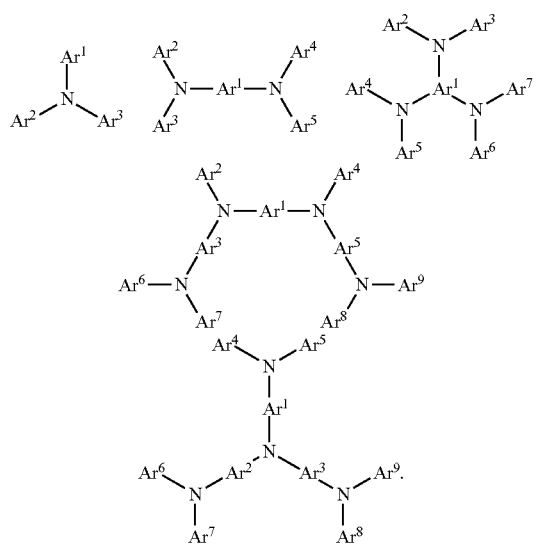

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atome, sulfur atom, silicon atom, phosphorus atom, boron atom, chain structural unit and the aliphatic cyclic group. Wherein each Ar is further substituted by a substituent selected from the group consisting of hydrogen, alkyl, alkoxy, amino, alkenyl, alkynyl, arylalkyl, heteroalkyl, aryl and heteroaryl.

In one aspect, $Ar^1$ to $Ar^9$ is independently selected from the group consisting of:

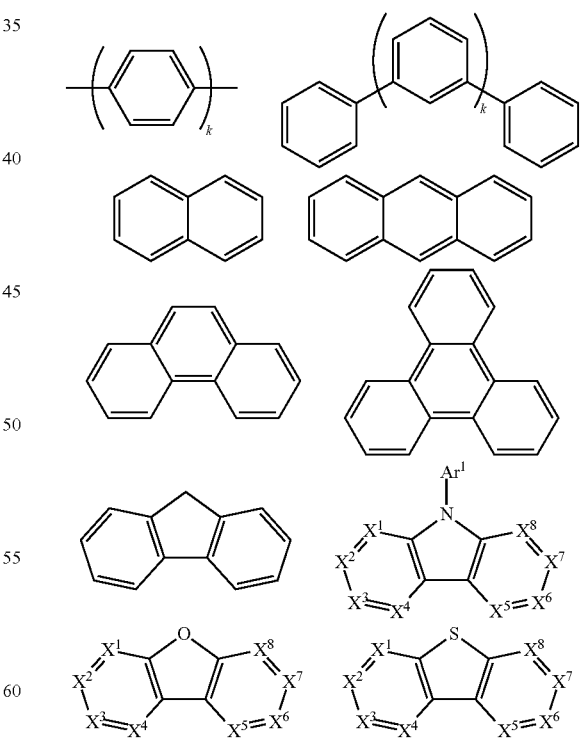

k is an integer from 1 to 20; $X^1$ to $X^8$ is CH or N; $Ar^1$ has the same group defined above.

Examples of metal complexes used in HIL or HTL include, but not limit to the following general formula:

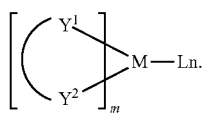

M is a metal, having an atomic weight greater than 40; ($Y^1$-$Y^2$) is a bindentate ligand, $Y^1$ and $Y^2$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, ($Y^1$-$Y^2$) is a 2-phenylpyridine derivative.

In another aspect, ($Y^1$-$Y^2$) is a carbene ligand.

In another aspect, M is selected from Ir, Pt, Os, and Zn.

In a further aspect, the metal complex has a smallest oxidation potential in solution vs. Fc$^+$/Fc couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant.

Examples of metal complexes used as host are preferred to have the following general formula:

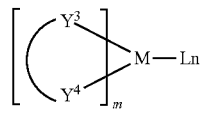

M is a metal; ($Y^3$-$Y^4$) is a bindentate ligand, $Y^3$ and $Y^4$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, the metal complexes are:

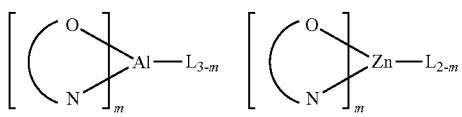

(O—N) is a bidentate ligand, having metal coordinated to atoms O and N.

In another aspect, M is selected from Ir and Pt.

In a further aspect, ($Y^3$-$Y^4$) is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atome, sulfur atom, silicon atom, phosphorus atom, boron atom, chain structural unit and the aliphatic cyclic group. Wherein each group is further substituted by a substituent selected from the group consisting of hydrogen, alkyl, alkoxy, amino, alkenyl, alkynyl, arylalkyl, heteroalkyl, aryl and heteroaryl.

In one aspect, host compound contains at least one of the following groups in the molecule:

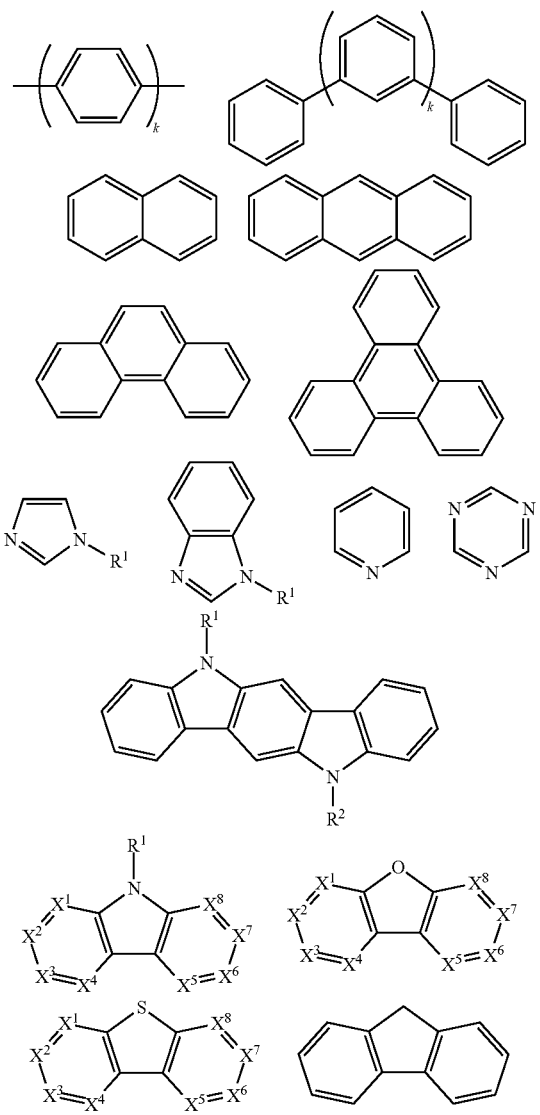

-continued

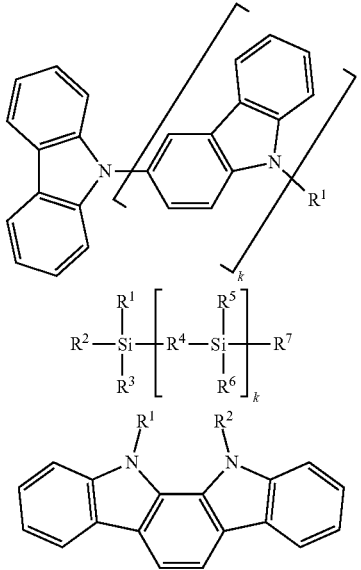

R¹ to R⁷ is independently selected from the group consisting of hydrogen, alkyl, alkoxy, amino, alkenyl, alkynyl, arylalkyl, heteroalkyl, aryl and heteroaryl, when it is aryl or heteroaryl, it has the similar definition as Ar's mentioned above;

k is an integer from 0 to 20;

X¹ to X⁸ is selected from CH or N.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule used as host described above.

In another aspect, compound used in HBL contains at least one of the following groups in the molecule:

k is an integer from 0 to 20; L is an ancillary ligand, m is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

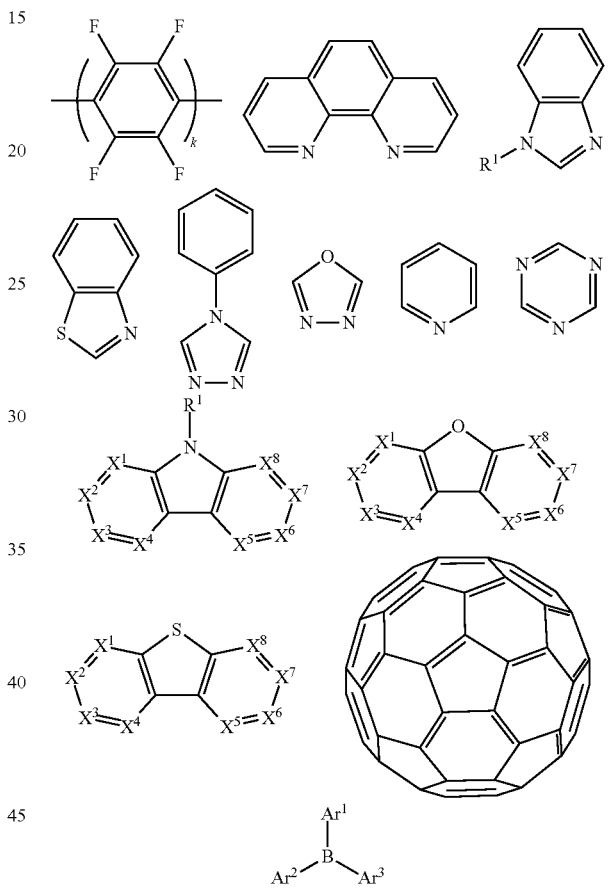

R¹ is selected from the group consisting of hydrogen, alkyl, alkoxy, amino, alkenyl, alkynyl, arylalkyl, heteroalkyl, aryl and heteroaryl, when it is aryl or heteroaryl, it has the similar definition as Ar's mentioned above;

Ar¹ to Ar⁹ has the similar definition as Ar's mentioned above;

k is an integer from 0 to 20;

X¹ to X⁸ is selected from CH or N.

In another aspect, the metal complexes used in ETL contains, but not limit to the following general formula:

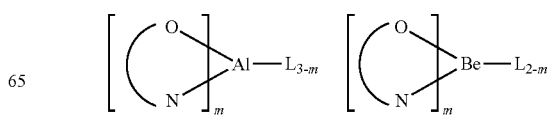

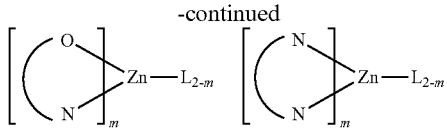

(O—N) or (N—N) is a bidentate ligand, having metal coordinated to atoms O, N or N, N; L is an ancillary ligand; m is an integer value from 1 to the maximum number of ligands that may be attached to the metal.

EXPERIMENTAL

Compound Examples

Example 1. Synthesis of Ligand in Compound 88

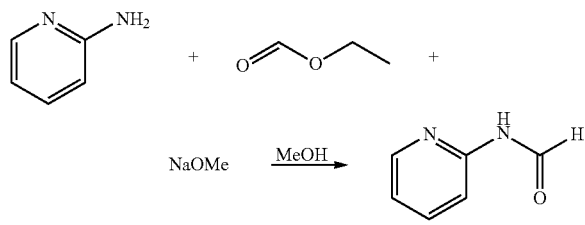

Synthesis of N-(pyridin-2-yl)formamide

To a solution of sodium methoxide (176 mL, 25 wt %, 0.81 mol) in 500 mL of methanol was added 2-aminopyridine (30.0 g, 0.32 mol) and the resulting solution was stirred at 40° C. for 30 minutes. Ethyl formate (220 mL, 2.76 mol) was then added dropwise and the reaction mixture was stirred overnight at 40° C. After cooling to room temperature, 250 mL of $H_2O$ and 250 mL of $CH_2Cl_2$ were added and conc. HCl (~40 mL) was added dropwise until pH ~5. Most of the methanol was evaporated and the resulting mixture was extracted with 3×150 mL of $CH_2Cl_2$. The combined organic portions were washed with 250 mL of $H_2O$ and 150 mL of brine and dried over $Na_2SO_4$. After evaporation of the solvent, 20.2 g of crude solid was obtained and distilled on a Kugelrohr at an oven temperature of 140° C. to yield 18.98 g of a white solid as the product.

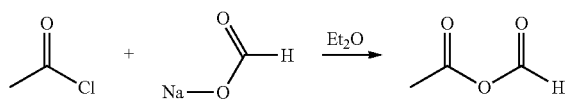

Synthesis of Acetic Formic Anhydride

Acetyl chloride (41 mL, 0.577 mol) was added rapidly through an addition funnel to a mixture of sodium formate (59 g, 0.86 mol) in 50 mL of ether in an ice/salt bath. The reaction mixture was stirred overnight and the resulting acetic formic anhydride ethereal solution was used without further purification.

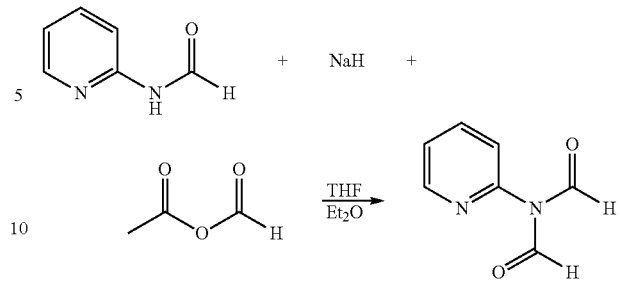

Synthesis of N-formyl-N-(pyridin-2-yl)formamide

To a suspension of sodium hydride (10.8 g, 60 wt %, 0.27 mol) in 50 mL of THF was added dropwise a solution of N-(pyridine-2-yl)formamide (22.4 g, 0.18 mol) in 250 mL of THF. When the addition was complete, the reaction was stirred at room temperature for 30 minutes and then cooled in an ice/salt bath. The acetic formic anhydride ethereal solution from the previous step was added in one portion. The resulting mixture was stirred in the ice bath for 30 minutes and then overnight at room temperature. The mixture was poured into 1 L of ice/water and extracted with 3×250 mL of $CH_2Cl_2$. The combined organic extracts were washed with 2×250 mL of $H_2O$, dried and evaporated to give 33.2 g of solid. The crude product was column chromatographed (silica gel) eluting with 100% $CH_2Cl_2$ followed by 90:10 $CH_2Cl_2$:EtOAc. 14.2 g of product was isolated as a white solid.

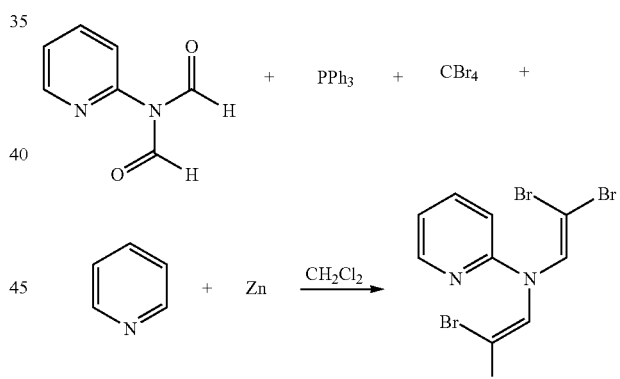

Synthesis of N,N-bis(2,2-dibromovinyl)pyridin-2-amine

In a 2 L, 3-neck flask with magnetic stirrer, thermocouple, condenser, nitorgen inlet and addition funnel triphenylphosphine (82.5 g, 0.31 mol) and tetrabromomethane (103.5 g, 0.31 mol) was dissolved in 750 mL of $CH_2Cl_2$. Zinc (20.27 g, 0.31 mol) was added giving an orange mixture. The reaction mixture was cooled to ~10° C. in an ice bath and stirred for 10 minutes. A solution of N-formyl-N-(pyridine-2-yl)formamide (5.9 g, 0.04 mol) in 100 mL of $CH_2Cl_2$ was added in a slow stream through the addition funnel. Pyridine (32.7 mL, 0.41 mol) was then added through the addition funnel. The reaction temperature rises from 10° C. to 24° C. and turns dark brown in color. The reaction mixture was stirred overnight, slowly warming to room temperature, and filtered through celite. The filtrate was washed with 2×250 mL of water and 250 mL of brine, dried and evaporated leaving ~200 g of a black gummy solid. The crude material was chromatographed on a flash silica column eluted with 75:25 hexane:$CH_2Cl_2$ followed by 50:50 hexane:$CH_2Cl_2$ and finally 25:75 hexane:$CH_2Cl_2$, yielding 14.9 g of product.

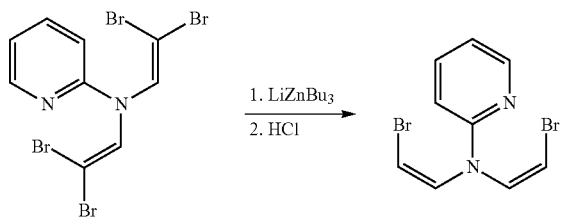 [SMILES: BrC(Br)=CN(C=C(Br)Br)c1ccccn1 ; Br/C=C\N(/C=C\Br)c1ccccn1]

Synthesis of N,N-bis((Z)-2-bromovinyl)pyridin-2-amine

An oven-dried 500 mL, 3-neck flask with magnetic stirrer, addition funnel, thermocouple and nitrogen inlet was charged with anhydrous zinc chloride (15.0 g, 0.11 mol) and cooled in an ice/salt bath. 100 mL of THF was then added dropwise. Butyllithium (134 mL, 2.5 M in hexanes, 0.34 mol) was then added dropwise such that the temperature was maintained below 0° C., giving a milky white solution that was stirred at 0° C. for 30 minutes. The ice/salt bath was replaced with a dry ice/acetone bath and the reaction cooled to −75° C. N,N-bis(2,2-dibromovinyl)pridin-2-amine (5.0 g, 0.011 mol) in 50 mL of THF was added dropwise and the reaction stirred at −75° C. for 20 h. While still at −75° C., 100 mL of 10% acetic acid in THF was added dropwise and the cold solution poured into 150 mL of 1 N HCl. The reaction mixture was extracted with 3×100 mL of ether and the combined organics were washed with 2×100 mL of saturated $NaHCO_3$, dried and evaporated leaving 3.0 g of an colorless liquid as the product.

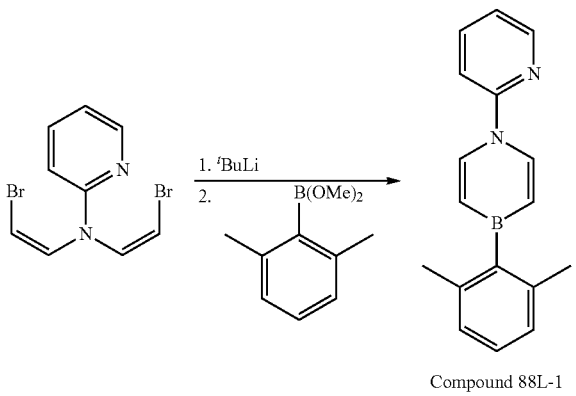

Compound 88L-1

Synthesis of Ligand in Compound 88

$^t$BuLi (4.9 mL, 1.7 M in pentane, 8.3 mmol) was added dropwise to a solution of N,N-bis((Z)-2-bromovinyl)pyridin-2-amine (500 mg, 1.650 mmol) in 50 mL of $Et_2O$ at −70° C. A precipitate was formed and the solution turned slightly darker to a pale orange mixture. The reaction mixture was stirred for 3 h at −70° C. during which time the precipitate went into solution. Dimethyl (2,6-dimethylphenyl)boronate (322 mg, 2.14 mmol) in 10 mL of ether was then added dropwise to the reaction solution, which was then allowed to warm slowly to room temperature. The reaction was filtered through a plug of Celite and concentrated to give 200 mg of a solid. GC/MS confirmed product formation.

Example 2. Synthesis of Ligand in Compound 87

Synthesis of 2-vinylaniline

A mixture of 2-(2-aminophenyl)ethanol (5 g, 36.4 mmol) and KOH (2.0 g, 36.4 mmol) was heated to 200° C. for 4 h. After cooling, the mixture was distilled under vacuum to yield 2.1 g of product.

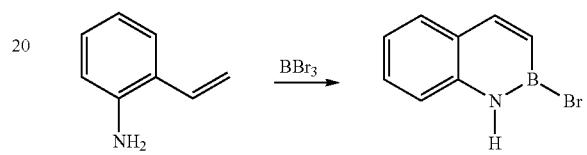

Synthesis of 2-chloro-1,2-dihydrobenzo[e][1,2]azaborine $BCl_3$ (67.8 mL, 1.0 M in hexanes) was added to a solution if 2-vinylaniline (5.3 g, 44.3 mmol) in 40 mL of anhydrous toluene at 0° C. The mixture was stirred at 0° C. for 1 h and then refluxed for 2 h. The mixture was then evaporated to dryness and used immediately for next step.

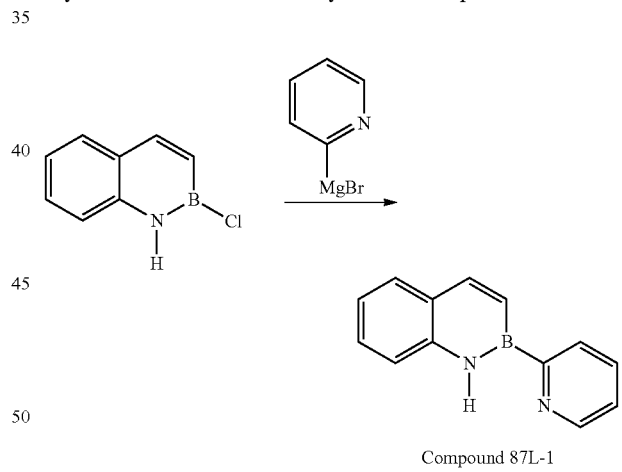

Compound 87L-1

Synthesis of Ligand in Compound 87

2-pyridylmagnesium bromide was generated by reacting isopropylmagnesium bromide (9.2 mL, 2.0 M in THF, 18.4 mmol) with 2-bromopyridine (2.9 g, 18.4 mmol) at room temperature for 2 h. This 2-pyridylmagnesium solution was then added to 2-chloro-1,2-dihydrobenzo[e][1,2]azaborine (1.0 g, 6.12 mmol) in anhydrous THF (30 mL) at −78° C. The mixture was stirred at −78° C. for 2 h and warm to room temperature. The mixture was poured into water and extracted with ethyl acetate. The organic extracts were dried and concentrated. The residue was column chromatographed (30% EtOAc in hexanes) to yield 0.5 g of product.

Example 3. Synthesis of Ligand in Compound 86

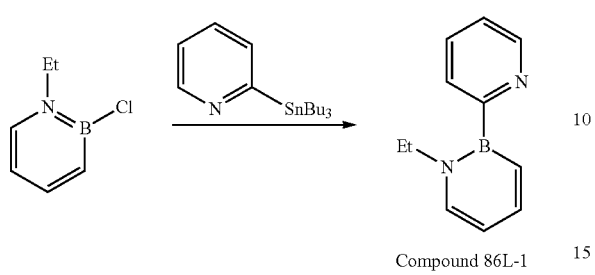

Compound 86L-1

2-chloro-1-ethyl-1,2-azaborine (0.14 g, 1.0 mmol) in THF (5 mL) was add to a mixture of 2-(tributylstannyl)pyridine (0.45 g, 1.1 mmol) in THF (20 mL). The mixture was stirred at room temperature for 72 h. The reaction mixture was then diluted with ethyl acetate (50 mL) and washed with brine (50 mL). The organic layer was dried over sodium sulfate and evaporated in vacuo. GCMS and NMR confirmed product formation.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore includes variations from the particular examples and preferred embodiments described herein, as will be apparent to one of skill in the art. It is understood that various theories as to why the invention works are not intended to be limiting.

The invention claimed is:

1. A compound having the formula:

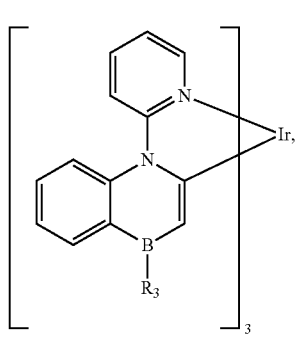

FORMULA XII wherein $R_3$ is selected from the group consisting of hydrogen, alkyl, alkoxy, amino, alkenyl, alkynyl, arylalkyl, aryl, and heteroaryl.

2. The compound according to claim 1, wherein the compound has the formula:

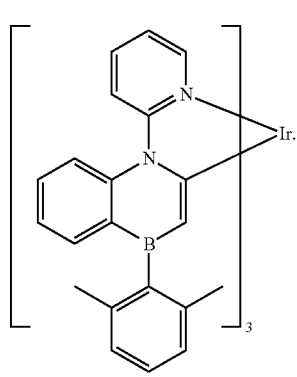

Compound H

* * * * *

UNITED STATES PATENT AND TRADEMARK OFFICE
CERTIFICATE OF CORRECTION

PATENT NO. : 9,673,406 B2
APPLICATION NO. : 14/052159
DATED : June 6, 2017
INVENTOR(S) : Raymond Kwong et al.

Page 1 of 26

It is certified that error appears in the above-identified patent and that said Letters Patent is hereby corrected as shown below:

In the Specification

Column 22, Lines 55-66, please delete

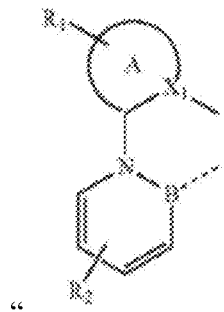

"

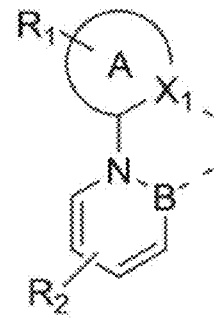

" and insert -- Compound 1 --

Column 23, Lines 1-12, please delete

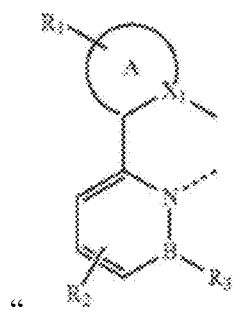

"

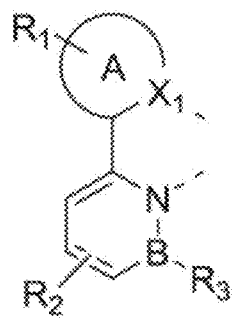

" and insert -- Compound 2 --

Signed and Sealed this
Sixth Day of February, 2018

Joseph Matal
*Performing the Functions and Duties of the
Under Secretary of Commerce for Intellectual Property and
Director of the United States Patent and Trademark Office*

CERTIFICATE OF CORRECTION (continued)
U.S. Pat. No. 9,673,406 B2

Column 23, Lines 13-22, please delete

" 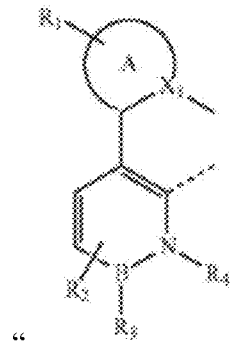 " and insert -- 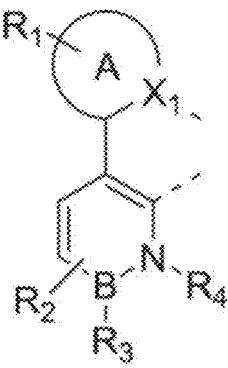 --

Column 23, Lines 23-26, please delete

" 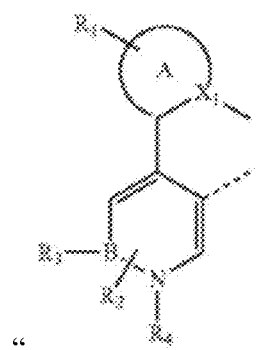 " and insert -- 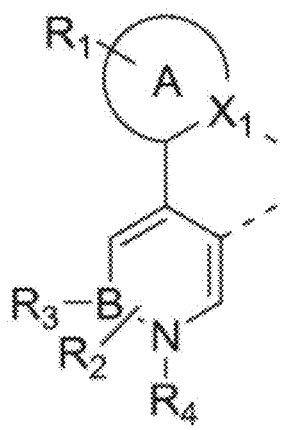 --

Column 23, Lines 37-46, please delete

" 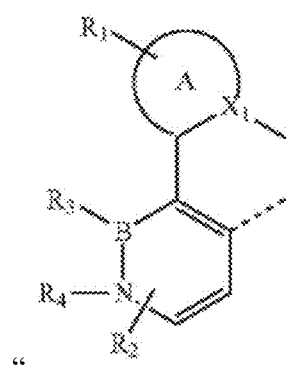 " and insert -- 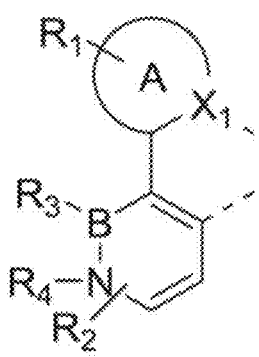 --

Column 23, Lines 47-56, please delete
"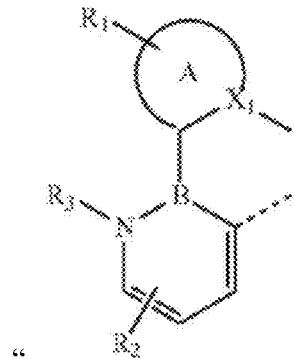 Compound 6" and insert -- 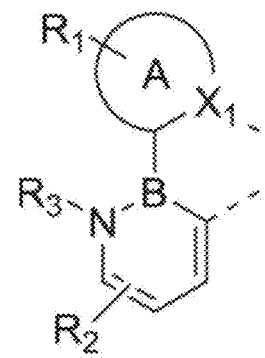 Compound 6 --
Column 23, Lines 57-66, please delete
"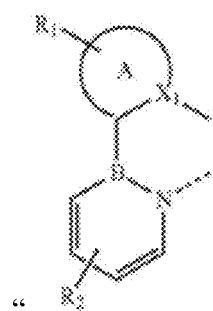 Compound 7" and insert -- 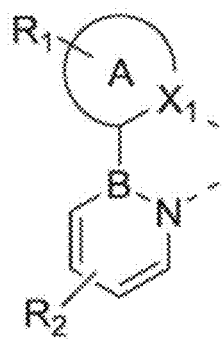 Compound 7 --
Column 24, Lines 1-12, please delete
"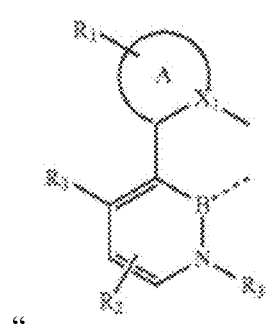 Compound 8" and insert -- 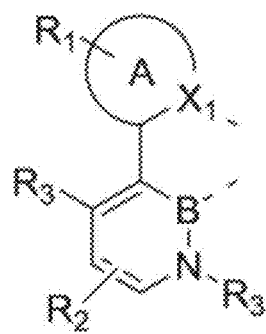 Compound 8 --

CERTIFICATE OF CORRECTION (continued)
U.S. Pat. No. 9,673,406 B2

Column 24, Lines 13-22, please delete

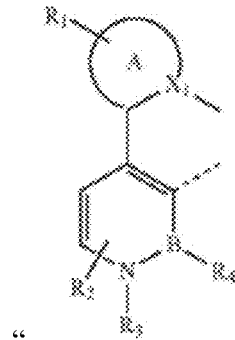
" and insert --
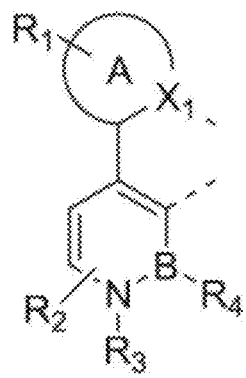
--

Column 24, Lines 23-34, please delete

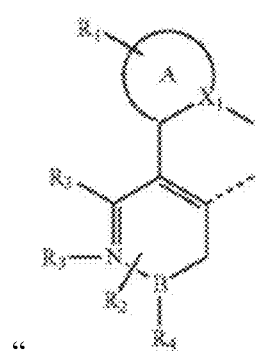
" and insert --
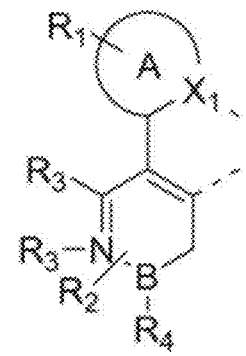
--

Column 24, Lines 35-44, please delete

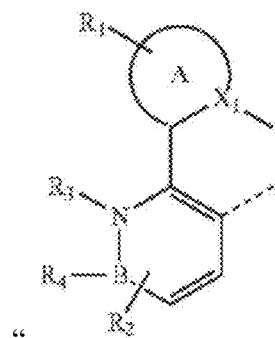
" and insert --
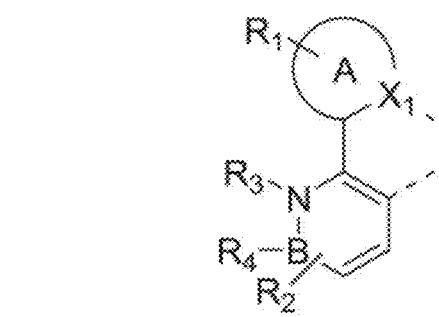
--

Column 24, Lines 45-56, please delete
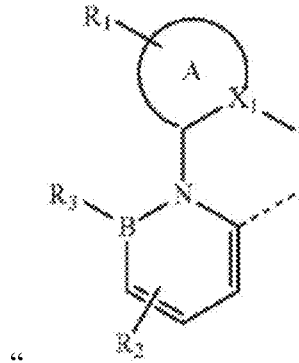 " and insert -- 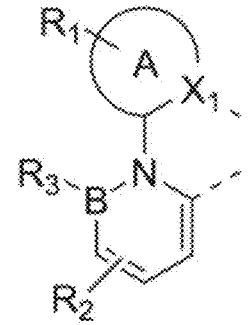 Compound 12 --
Column 24, Lines 57-66, please delete
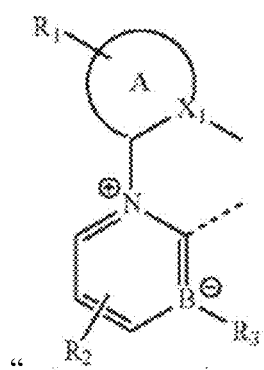 " and insert -- 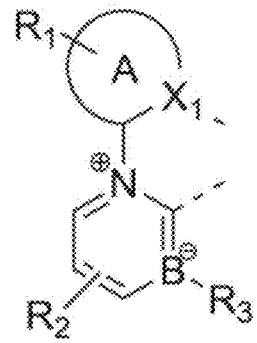 Compound 13 --
Column 25, Lines 1-13, please delete
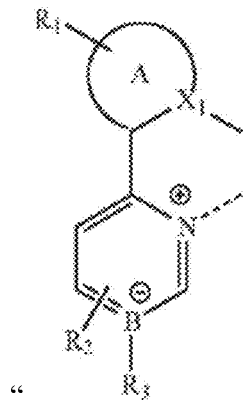 " and insert -- 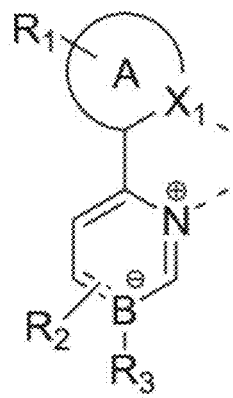 Compound 14 --

CERTIFICATE OF CORRECTION (continued)
U.S. Pat. No. 9,673,406 B2

Column 25, Lines 14-23, please delete

" 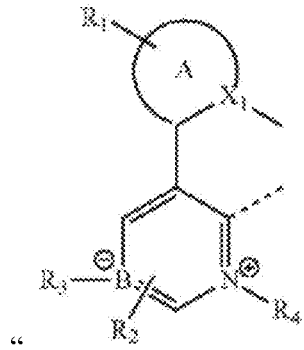 " and insert -- 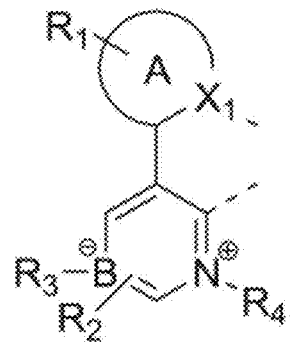 Compound 15 --

Column 25, Lines 24-34, please delete

" 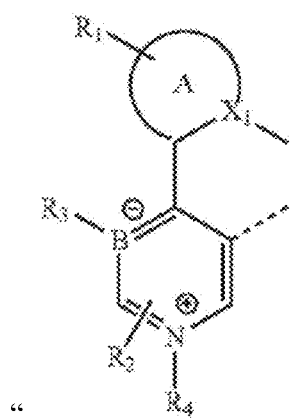 " and insert -- 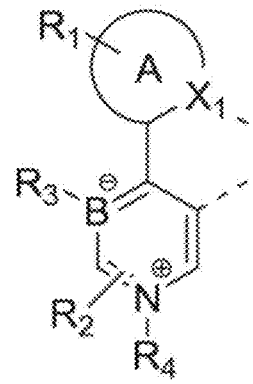 Compound 16 --

Column 25, Lines 35-45, please delete

" 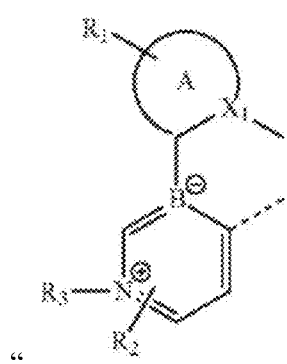 " and insert -- 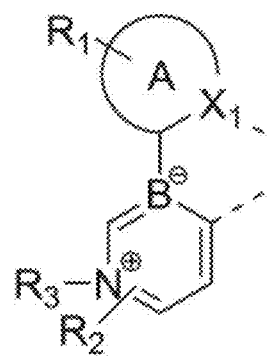 Compound 17 --

CERTIFICATE OF CORRECTION (continued)
U.S. Pat. No. 9,673,406 B2

Column 25, Lines 46-55, please delete

" 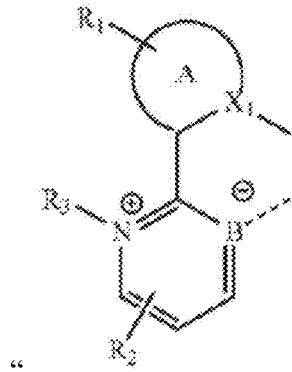 " and insert -- 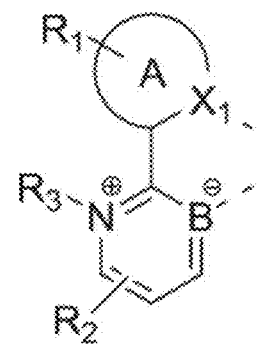 --

Column 25, Lines 56-66, please delete

" 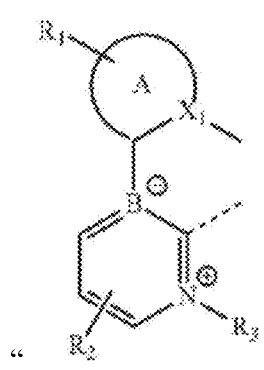 " and insert -- 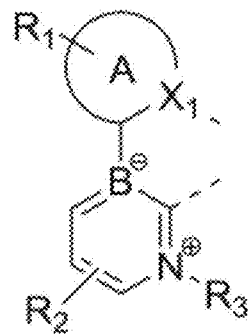 --

Column 26, Lines 1-13, please delete

" 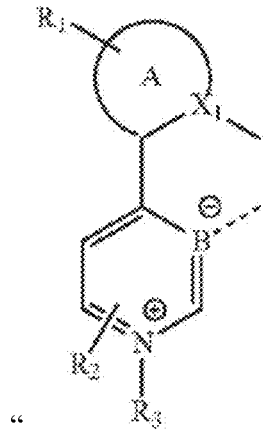 " and insert -- 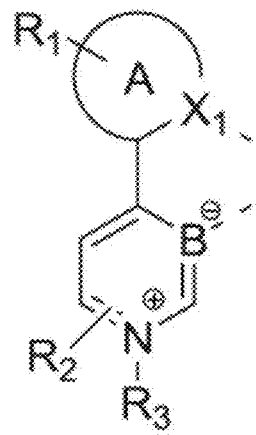 --

CERTIFICATE OF CORRECTION (continued)
U.S. Pat. No. 9,673,406 B2

Column 26, Lines 14-23, please delete

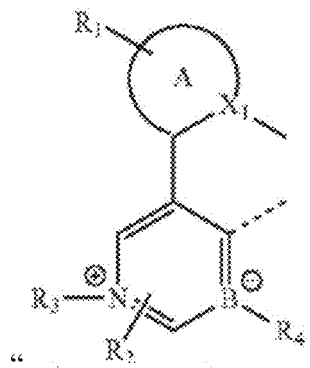

"  " and insert -- 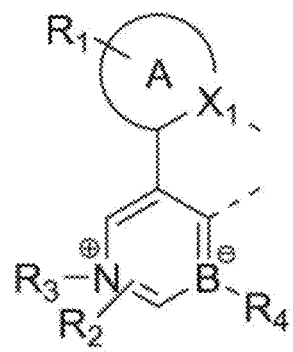 --

Column 26, Lines 24-34, please delete

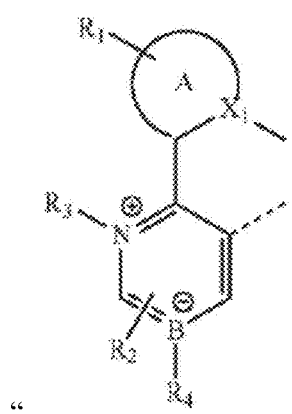

"  " and insert -- 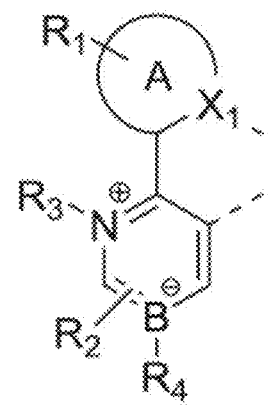 --

Column 26, Lines 35-45, please delete

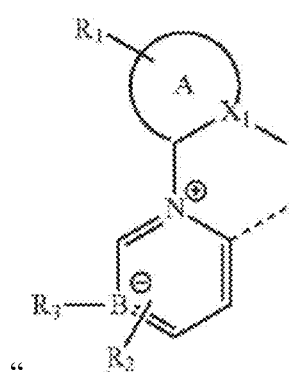

"  " and insert -- 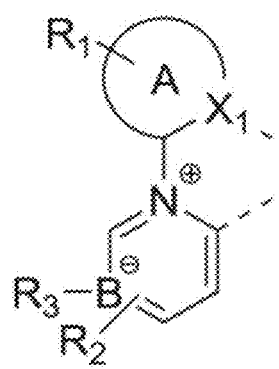 --

CERTIFICATE OF CORRECTION (continued)
U.S. Pat. No. 9,673,406 B2

Column 26, Lines 46-55, please delete

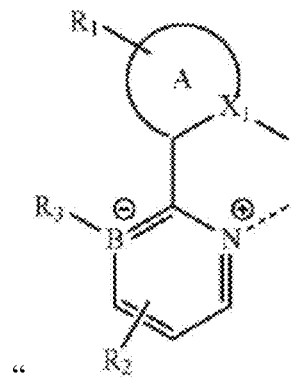 " and insert -- 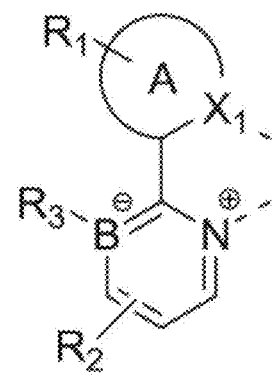 --

Column 26, Lines 57-66, please delete

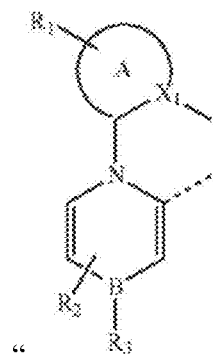 " and insert -- 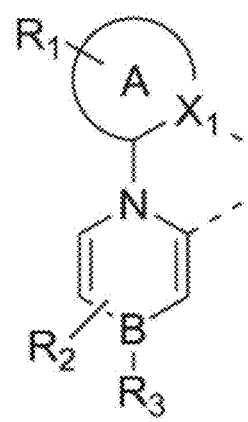 --

Column 27, Lines 1-13, please delete

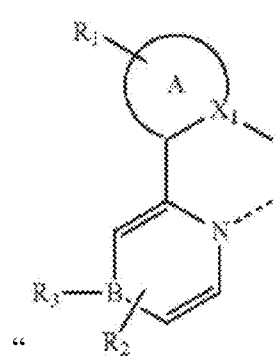 " and insert -- 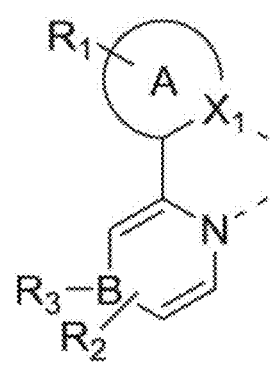 --

CERTIFICATE OF CORRECTION (continued)
U.S. Pat. No. 9,673,406 B2

Column 27, Lines 13-22, please delete

" 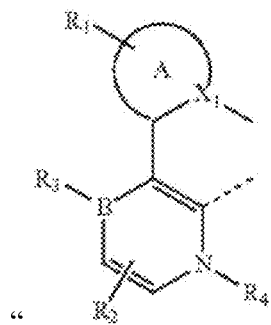 " and insert -- 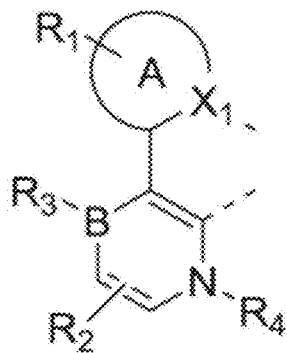 --

Column 27, Lines 23-33, please delete

" 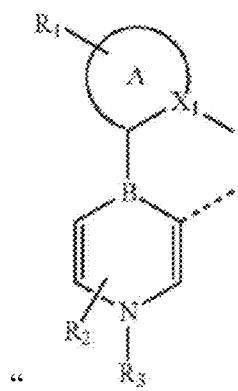 " and insert -- 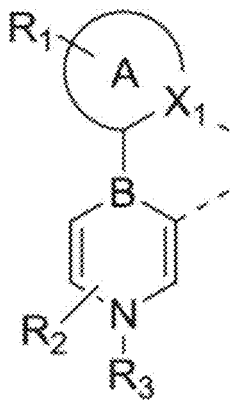 --

Column 27, Lines 34-43, please delete

" 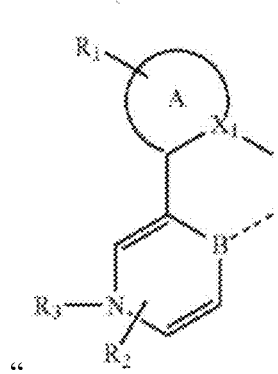 " and insert -- 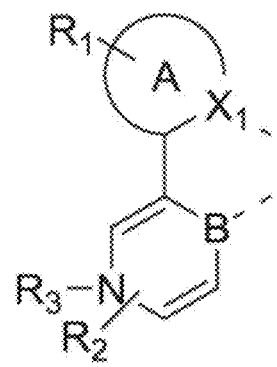 --

CERTIFICATE OF CORRECTION (continued)
U.S. Pat. No. 9,673,406 B2

Column 27, Lines 44-54, please delete

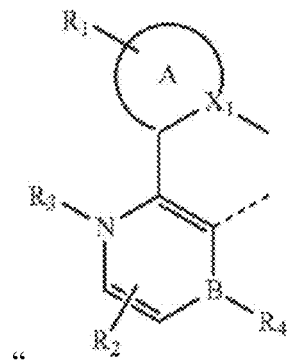 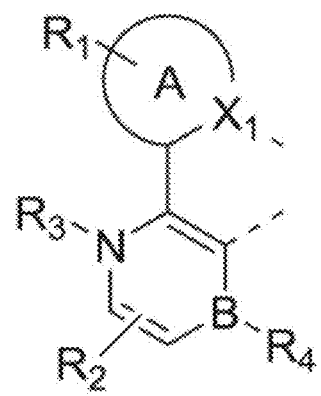

" and insert -- Compound 30 --

Column 27, Lines 55-66, please delete

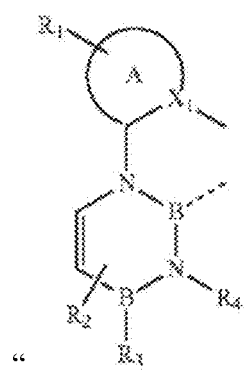 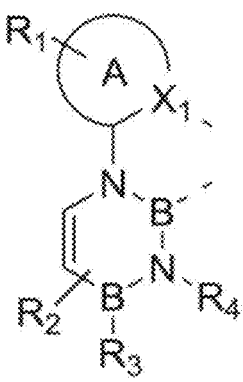

" and insert -- Compound 31 --

Column 28, Lines 1-13, please delete

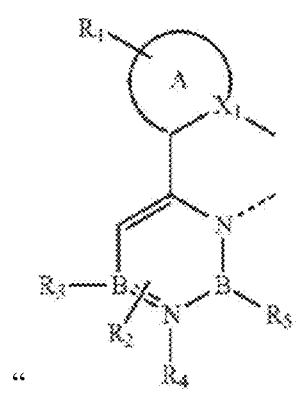 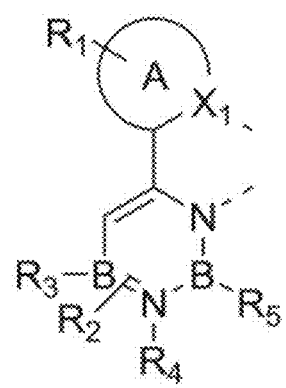

" and insert -- Compound 32 --

Column 28, Lines 14-23, please delete
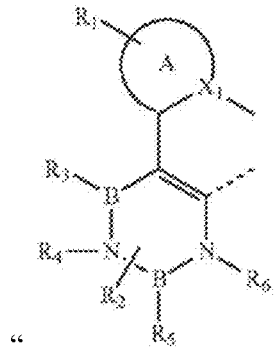
" and insert --
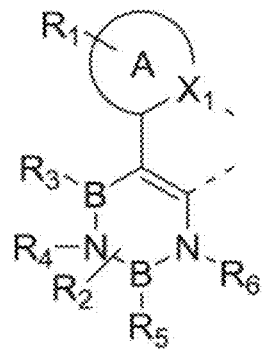
Compound 33 --
Column 28, Lines 24-34, please delete
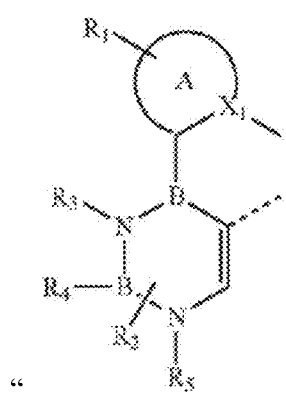
" and insert --
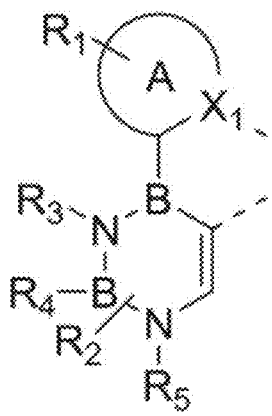
Compound 34 --
Column 28, Lines 35-44, please delete
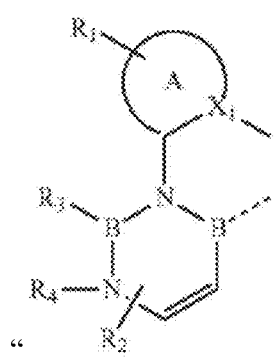
" and insert --
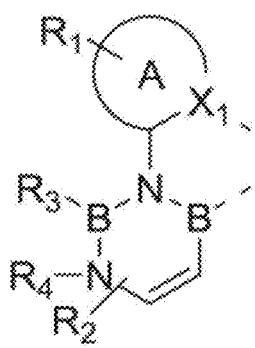
Compound 35 --

CERTIFICATE OF CORRECTION (continued)
U.S. Pat. No. 9,673,406 B2

Column 28, Lines 45-54, please delete

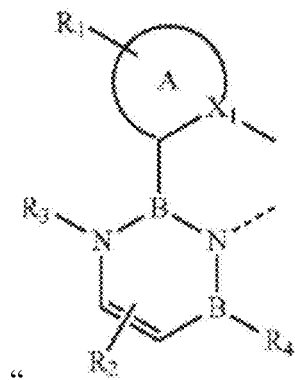
"
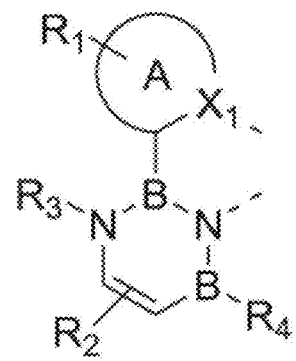
" and insert -- Compound 36 --

Column 28, Lines 55-66, please delete

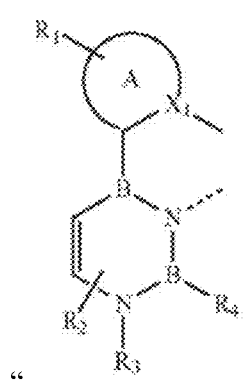
"
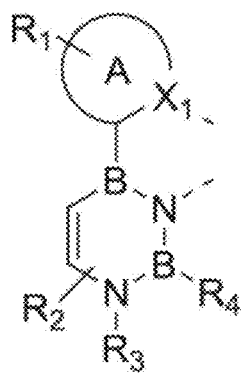
" and insert -- Compound 37 --

Column 29, Lines 1-13, please delete

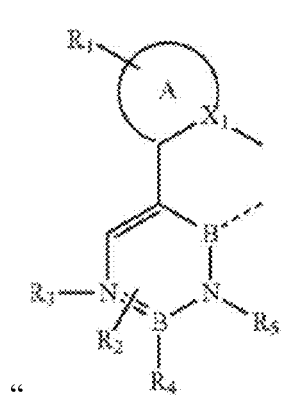
"
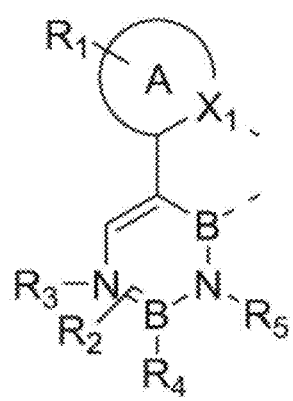
" and insert -- Compound 38 --

CERTIFICATE OF CORRECTION (continued)
U.S. Pat. No. 9,673,406 B2

Column 29, Lines 14-23, please delete

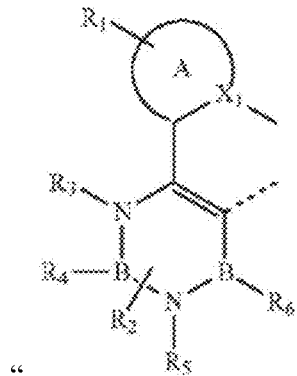

" 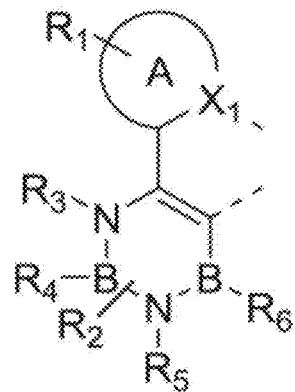 and insert -- Compound 39 --

Column 29, Lines 24-35, please delete

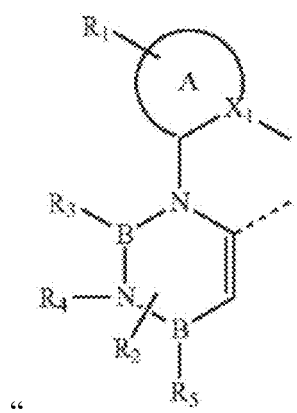

" 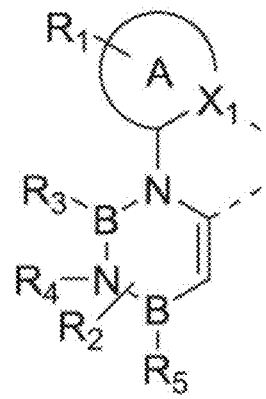 and insert -- Compound 40 --

Column 29, Lines 36-45, please delete

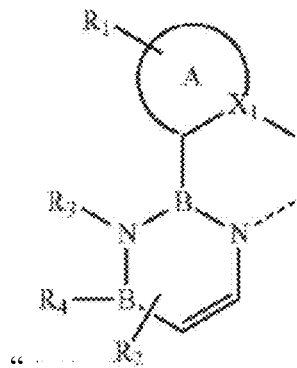

" 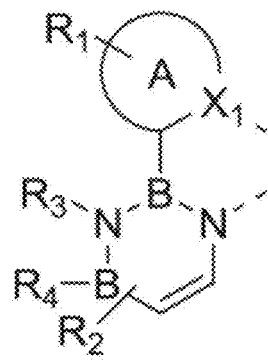 and insert -- Compound 41 --

CERTIFICATE OF CORRECTION (continued)
U.S. Pat. No. 9,673,406 B2

Column 29, Lines 46-55, please delete

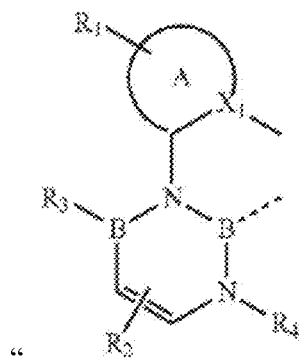

"       " and insert -- 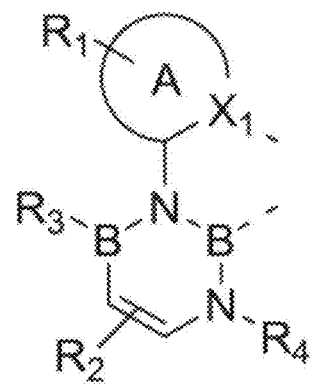 --

Column 29, Lines 56-66, please delete

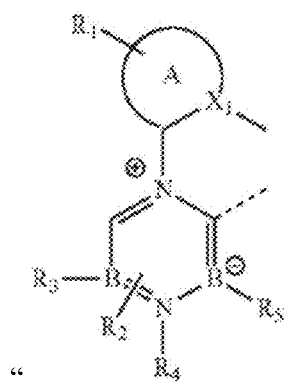

"       " and insert -- 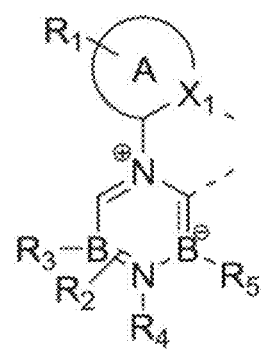 --

Column 30, Lines 1-12, please delete

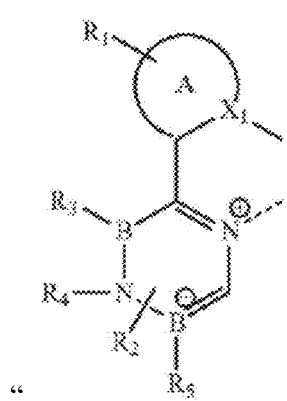

"       " and insert -- 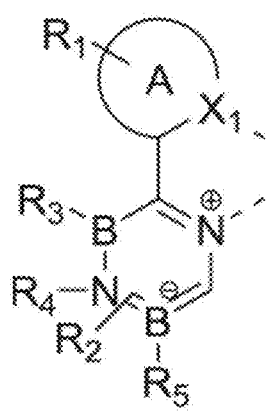 --

CERTIFICATE OF CORRECTION (continued)
U.S. Pat. No. 9,673,406 B2

Column 30, Lines 13-22, please delete

" 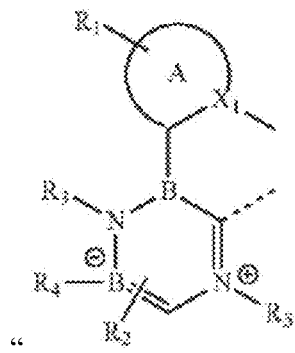 " and insert -- 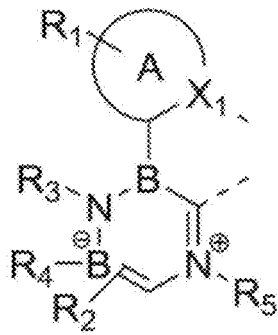 Compound 45 --

Column 30, Lines 23-33, please delete

" 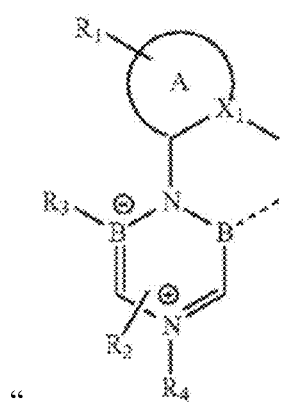 " and insert -- 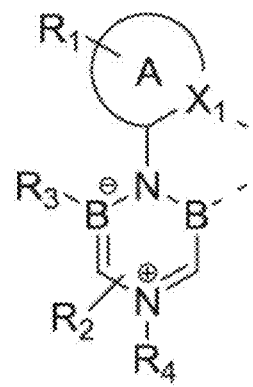 Compound 46 --

Column 30, Lines 34-44, please delete

" 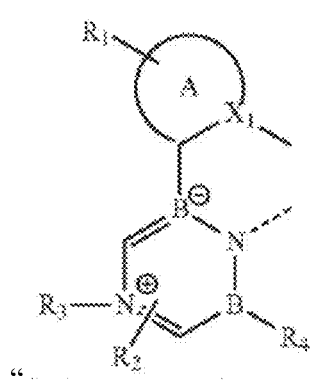 " and insert -- 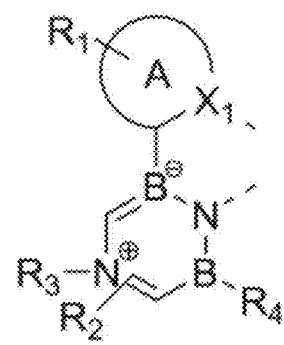 Compound 47 --

CERTIFICATE OF CORRECTION (continued)
U.S. Pat. No. 9,673,406 B2

Column 30, Lines 45-55, please delete

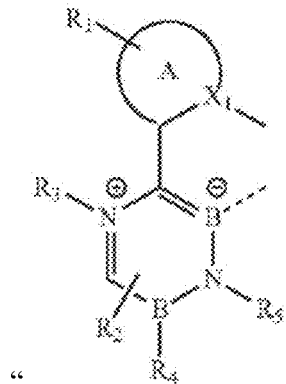 " and insert -- 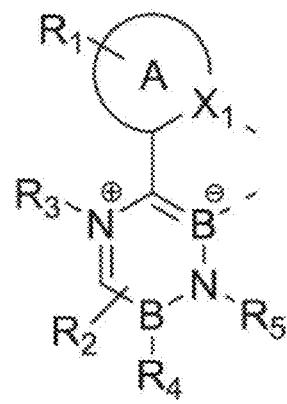 Compound 48 --

Column 30, Lines 56-66, please delete

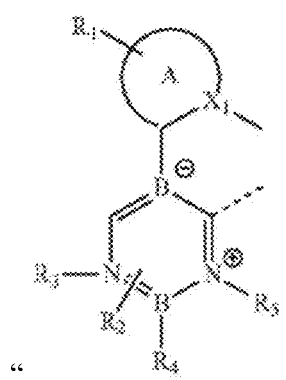 " and insert -- 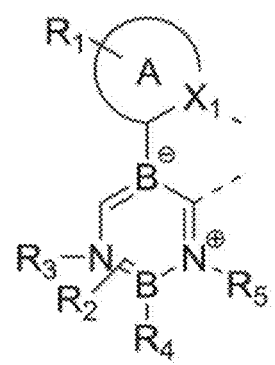 Compound 49 --

Column 31, Lines 1-12, please delete

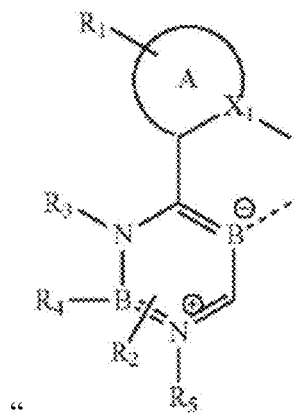 " and insert -- 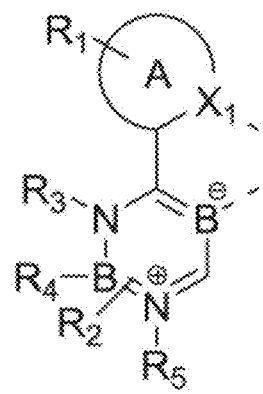 Compound 50 --

Column 31, Lines 13-22, please delete
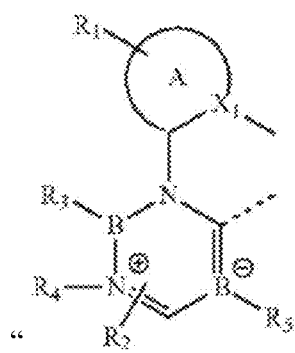
"  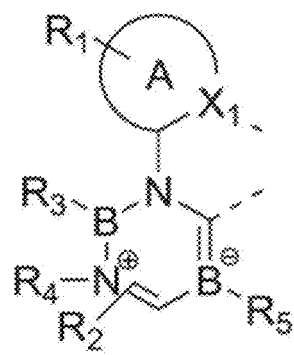 " and insert -- Compound 51 --
Column 31, Lines 23-33, please delete
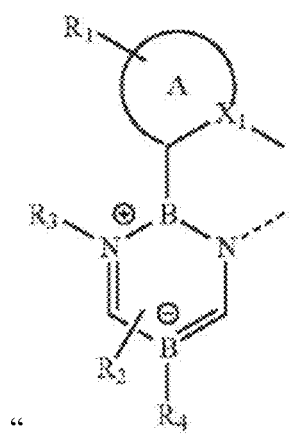
"  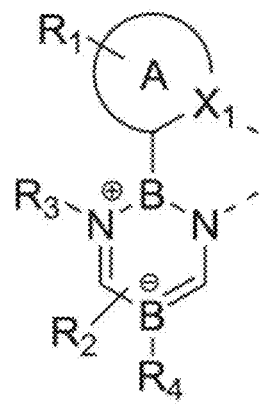 " and insert -- Compound 52 --
Column 31, Lines 34-43, please delete
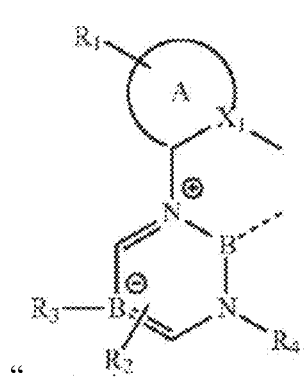
"  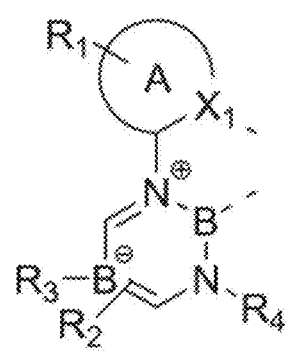 " and insert -- Compound 53 --

CERTIFICATE OF CORRECTION (continued)
U.S. Pat. No. 9,673,406 B2

Column 31, Lines 44-55, please delete

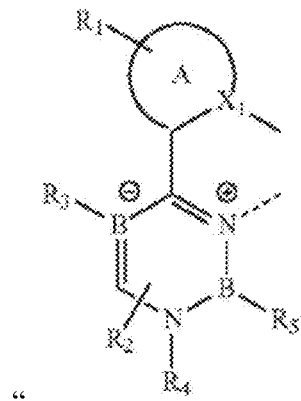 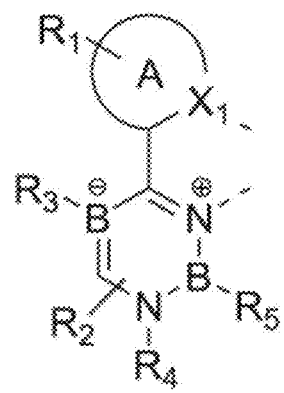

" and insert -- Compound 54 --

Column 31, Lines 56-66, please delete

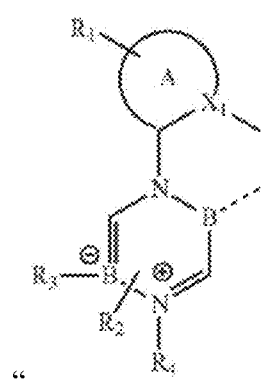 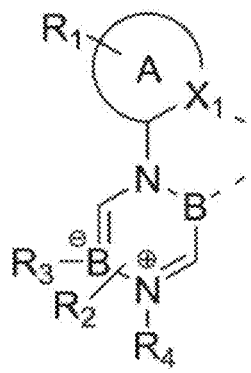

" and insert -- Compound 55 --

Column 32, Lines 1-12, please delete

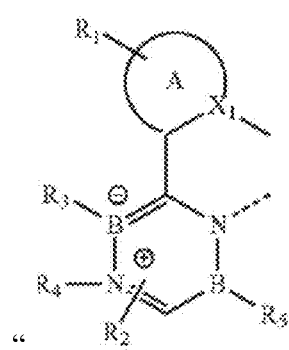 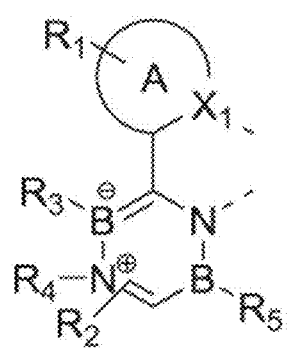

" and insert -- Compound 56 --

CERTIFICATE OF CORRECTION (continued)
U.S. Pat. No. 9,673,406 B2

Column 32, Lines 13-23, please delete

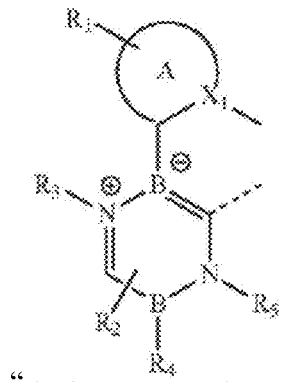

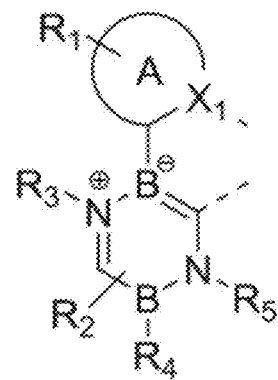

" and insert -- Compound 57 --

Column 32, Lines 24-33, please delete

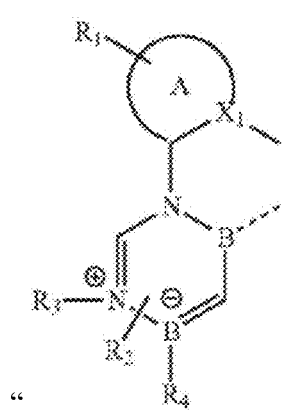

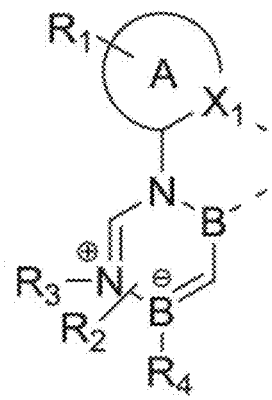

" and insert -- Compound 58 --

Column 32, Lines 34-44, please delete

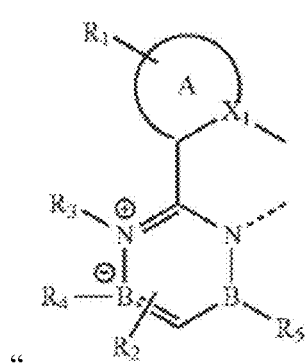

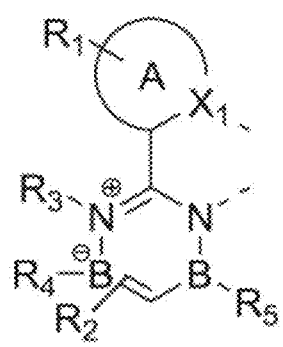

" and insert -- Compound 59 --

CERTIFICATE OF CORRECTION (continued)
U.S. Pat. No. 9,673,406 B2

Column 32, Lines 45-55, please delete

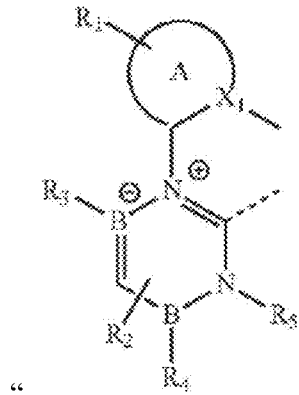 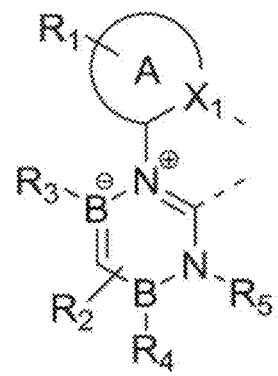

" and insert -- 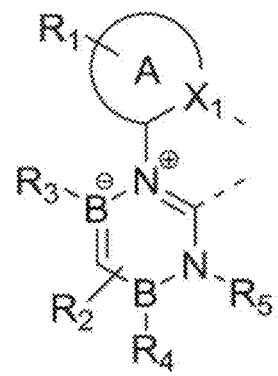 --

Column 32, Lines 56-66, please delete

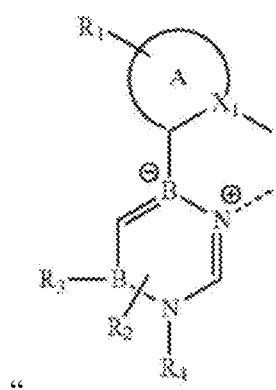 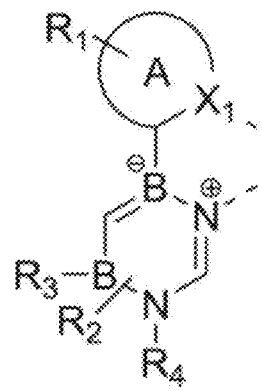

" and insert -- 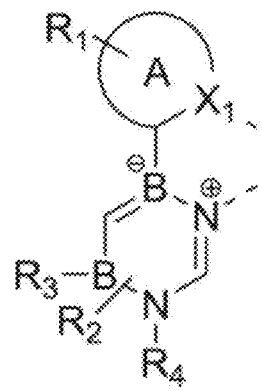 --

Column 33, Lines 1-12, please delete

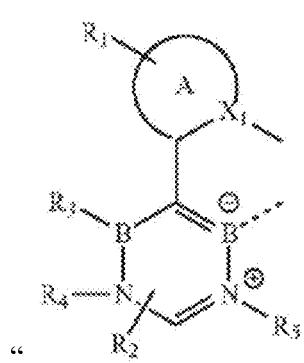 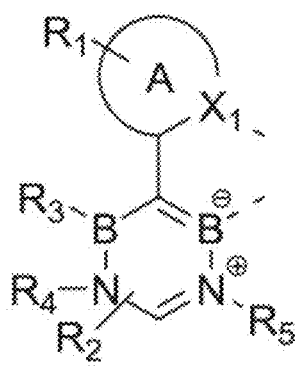

" and insert -- 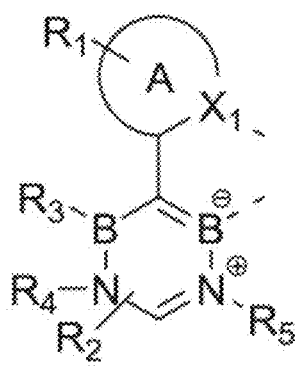 --

CERTIFICATE OF CORRECTION (continued)
U.S. Pat. No. 9,673,406 B2

Column 33, Lines 13-22, please delete

" 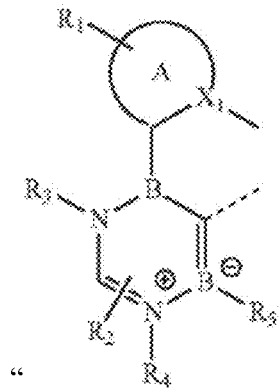 " and insert -- 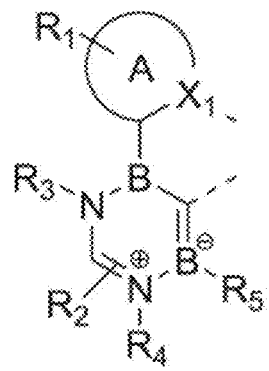 Compound 63 --

Column 33, Lines 23-33, please delete

" 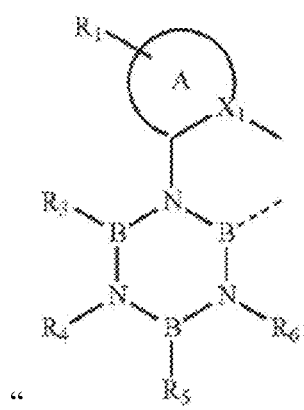 " and insert -- 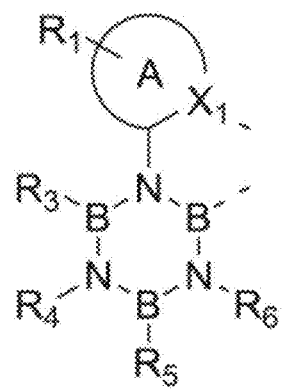 Compound 64 --

Column 33, Lines 34-45, please delete

" 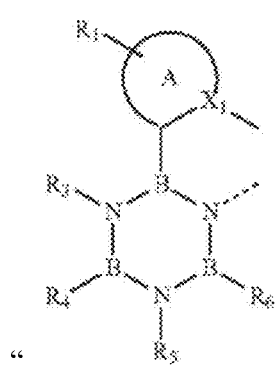 " and insert -- 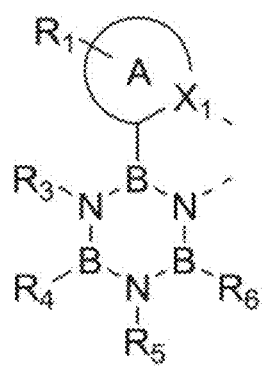 Compound 65 --

CERTIFICATE OF CORRECTION (continued)
U.S. Pat. No. 9,673,406 B2

Column 33, Lines 46-56, please delete

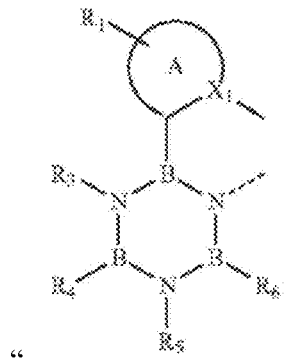

" and insert -- 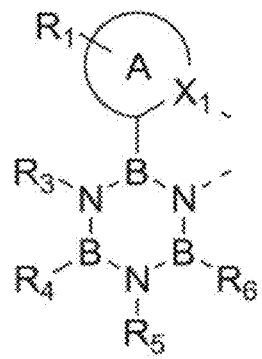 Compound 65 --

Column 33, Lines 57-66, please delete

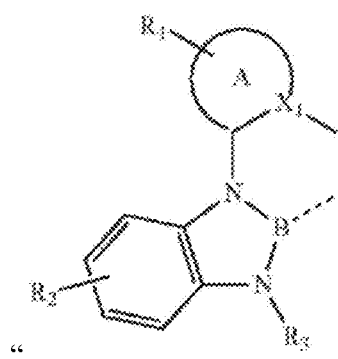

" and insert -- 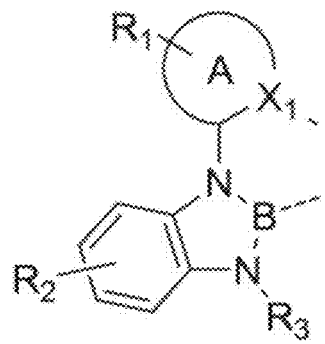 Compound 66 --

Column 34, Lines 1-13, please delete

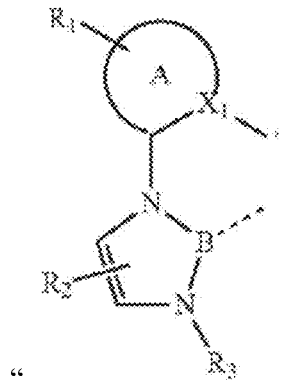

" and insert -- 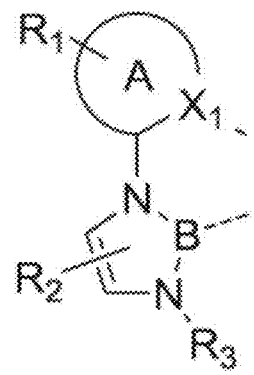 Compound 67 --

CERTIFICATE OF CORRECTION (continued)
U.S. Pat. No. 9,673,406 B2

Column 34, Lines 20-32, please delete

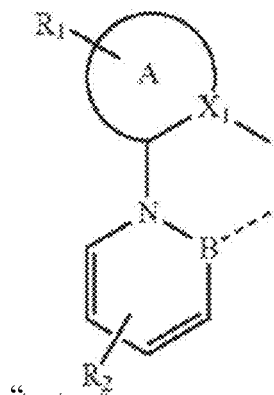

"

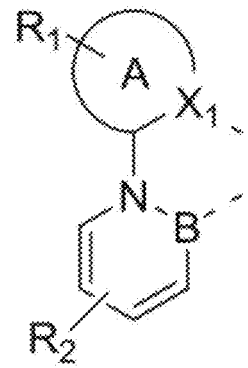

Compound 1

" and insert -- Compound 1 --

Column 34, Lines 33-44, please delete

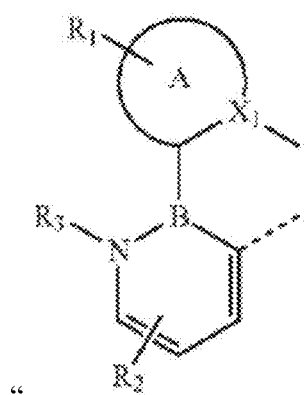

"

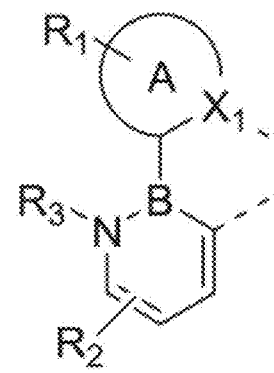

Compound 6

" and insert -- Compound 6 --

Column 34, Lines 45-55, please delete

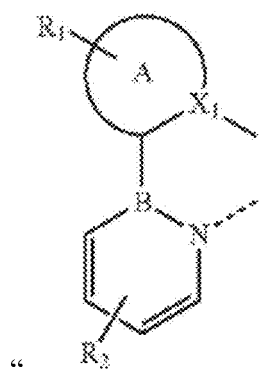

"

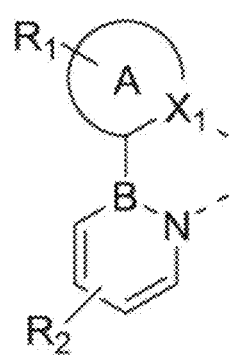

Compound 7

" and insert -- Compound 7 --

CERTIFICATE OF CORRECTION (continued)
U.S. Pat. No. 9,673,406 B2

Column 34, Lines 56-66, please delete

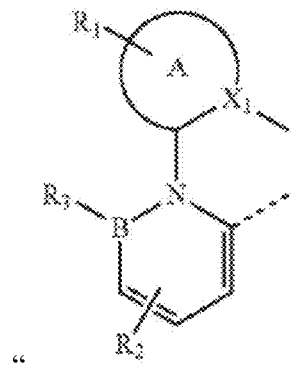

Compound 12

" and insert -- 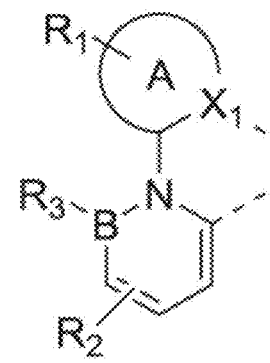 Compound 12 --

Column 35, Lines 1-12, please delete

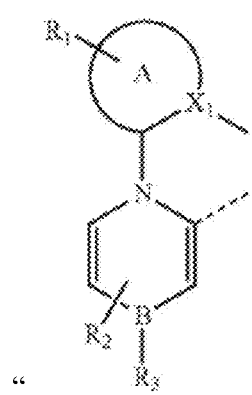

Compound 25

" and insert -- 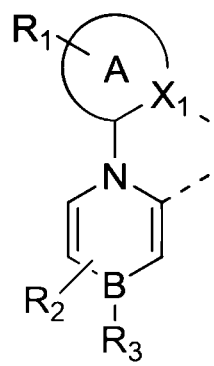 Compound 25 --

Column 35, Lines 13-24, please delete

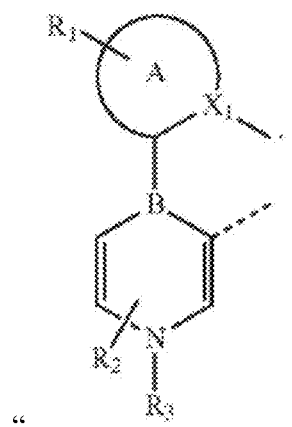

Compound 28

" and insert -- 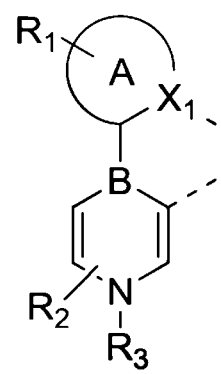 Compound 28 --

CERTIFICATE OF CORRECTION (continued)
U.S. Pat. No. 9,673,406 B2

Column 35, Lines 26-39, please delete

" 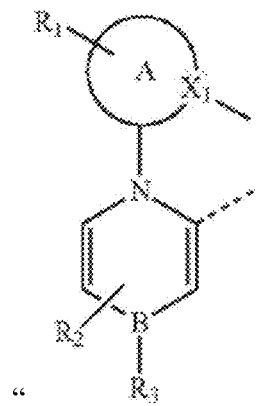 " and insert -- 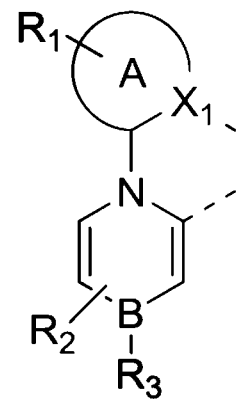 --